(12) United States Patent
Baraldi et al.

(10) Patent No.: US 7,335,655 B2
(45) Date of Patent: Feb. 26, 2008

(54) 8-HETEROARYL XANTHINE ADENOSINE $A_{2B}$ RECEPTOR ANTAGONISTS

(75) Inventors: Pier Giovanni Baraldi, Ferrara (IT); Pier A. Borea, Ferrara (IT)

(73) Assignee: King Pharmaceuticals Research and Development, Inc., Cary, NC (US)

( * ) Notice: Subject to any disclaimer, the term of this patent is extended or adjusted under 35 U.S.C. 154(b) by 0 days.

(21) Appl. No.: 11/359,661

(22) Filed: Feb. 22, 2006

(65) Prior Publication Data
US 2006/0142309 A1 Jun. 29, 2006

Related U.S. Application Data

(62) Division of application No. 10/357,865, filed on Feb. 3, 2003, now Pat. No. 7,205,403.

(60) Provisional application No. 60/353,317, filed on Feb. 1, 2002.

(51) Int. Cl.
C07D 473/06 (2006.01)
C07D 473/08 (2006.01)
A61K 31/522 (2006.01)
A61P 11/06 (2006.01)
A61P 19/02 (2006.01)

(52) U.S. Cl. .............. 514/234.2; 514/263.2; 514/263.21; 514/263.22

(58) Field of Classification Search ............ 514/234.2, 514/263.2, 263.21, 263.22
See application file for complete search history.

(56) References Cited

U.S. PATENT DOCUMENTS

| | | | | |
|---|---|---|---|---|
| 4,567,183 A | * | 1/1986 | Sunshine et al. | 514/263.31 |
| 4,593,095 A | * | 6/1986 | Snyder et al. | 544/272 |
| 5,424,297 A | * | 6/1995 | Rubio et al. | 544/272 |
| 5,935,964 A | | 8/1999 | Baraldi et al. | 514/267 |
| 6,117,878 A | | 9/2000 | Linden | 514/263 |
| 2007/0072843 A1 | * | 3/2007 | Wang et al. | 514/217.06 |

FOREIGN PATENT DOCUMENTS

| | | | |
|---|---|---|---|
| EP | 956855 A1 | * | 11/1999 |
| EP | 956855 B1 | | 3/2003 |

OTHER PUBLICATIONS

Mueller, J. Med. Chem 36(22) pp. 3341-3349.*
Baraldi et al., "Pyrazolo[4,3-e]-1,2,4-triazolo[1,5-c]-pyrimidine derivatives: potent and selective $A_{2A}$ adenosine antagonists", *J. Med. Chem.* 39: 1164-1171 (1996).
Baraldi et al., "Design, synthesis and biological evaluation of a second generation of pyrazolo[4,3-e]1,2,4-triazolo[1,5-c]-pyrimidines as potent and selective $A_{2A}$ adenosine receptor antagonists", *J. Med. Chem.* 41: 2126-2133 (1998).
Baraldi et al., "Pyrazolo[4,3-e]1,2,4-triazolo[1,5-c]-pyrimidine derivatives as highly potent and selective human $A_3$ adenosine receptor antagonists", *J. Med. Chem.* 42: 4473-4478 (1999).
Baraldi et al., "$A_3$ Adenosine receptor ligands; history and perspectives", *Med. Res. Rev.* 20: 103-128 (2000).
Baraldi et al., "Pyrazolo[4,3-e] 1,2,4-triazolo[1,5-c]-pyrimidine derivatives as adenosine receptor ligands: a search for $A_{2B}$ adenosine receptor", *Drug. Dev. Res.* 53: 225-235 (2001).
Boyle et al., "Inhibition of synoviocyte collagenase gene expression by adenosine receptor stimulation", *Arthritis Rheum.* 39: 923-930 (1996).
Bradford M. M., "A rapid and sensitive method for the quantification of microgram quantities of protein utilizing the pinciple of protein dye-binding", *Anal. Biochem.* 72: 248-254 (1976).
Cheng Y. C. and Prusoff W. H., "Relationships between the inhibition constant ($K_1$) and the concentration of inhibitor which causes 50 per cent inhibition ($IC_{50}$) of an enzymatic reaction", *Biochem. Pharmacol.* 22: 3099-3108 (1973).
Daly et al., "Subclasses of adenosine receptors in the central nervous system: interaction with caffeine and related methylxanthines", *Cell. Mol. Neurobiol.* 3: 69-80 (1983).
De Zwart et at., "Potent antagonist for the human adenosine $A_{2B}$ receptor. Derivatives of the triazolotriazine adenosine receptor antagonists ZM241385 with high affinity", *Drug Dev. Res.* 48: 95-103 (1999).
Dubey et al., "Adenosine inhibits growth of rat aortic smooth muscle cells: possible role of $A_{2B}$ receptors", *Hypertension* 27: 786-793 (1996).
Feoktisov I. and Biaggioni I., "Adenosine $A_{2B}$ receptors evoke interleukine-S secretion in human mast cells: an enprofylline-sensitive mechanism with implication for asthma", *J. Clin. Invest.* 96: 1979-1986 (1995).

(Continued)

*Primary Examiner*—Mark L. Berch
(74) *Attorney, Agent, or Firm*—Paivi Kukkola

(57) ABSTRACT

The present invention relates generally to compounds of formula (I):

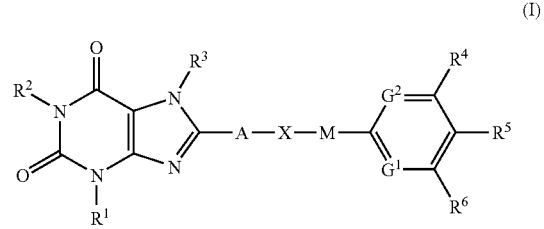

(I)

wherein
X is a five or six-membered heteroaromatic ring, containing one to four heteroatoms, selected from nitrogen, oxygen, or sulfur, provided that at least one heteroatom is nitrogen; and
$G^1$ and $G^2$ are independently CH or N.

The present invention also relates to the preparation of the compounds, pharmaceutical formulations thereof, and their use in medicine as potent or selective $A_{2B}$ adenosine receptor antagonists and their uses for treating asthma, autoimmune diseases and retinal vascular diseases.

10 Claims, 5 Drawing Sheets

OTHER PUBLICATIONS

Feoktistov I. and Biaggioni I., "Adenosine $A_{2B}$ receptors", *Pharmacol. Rev.* 49: 381-402 (1997).

Feokstistov I and Biaggioni I., "Pharmacological characterizatin of adenosine $A_{2B}$ receptors", *Biochem. Pharmacol.* 55: 627-633 (1998).

Feokstistov et al., "Adenosine $A_{2B}$ receptors as therapeutic targets", *Drug Dev. Res.* 45: 198-206 (1998).

Haynes et al., "Adenosine-induced vasodilation receptor characterization in pulmonary circulation", *Am. J. Physiol.* 26S: H1862-H1868 (1995).

Jacobson et al., "1,3-Dialkylxanthine derivatives having high potency as antagonists at human $A_{2B}$ adenosine receptors", *Drug Dev. Res.* 47: 45-53 (1999).

Ji X-D. and Jacobson K. A., "Use of triazolotriazine [$^3$H]-ZM241385 as a radioligand at recombinant human $A_{2B}$ adenosine receptors", *Drug Des. Discov.* 16: 217-226 (1999).

Ji et al., "[$^3$H]-MRS-1754, a selective antagonist radioligand for $A_{2B}$ adenosine receptors", *Biochem. Pharmacol.* 61: 657-663 (2001).

Kim et al, "Derivatives of the triazoloquinazoline adenosine antagonist (CGS 15943) having high potency at the human $A_{2B}$ and $A_3$ receptor subtypes", *J. Med. Chem.* 41: 2835-2845 (1998).

Kim et al., "Acyl-hydrazide derivatives of a xanthine carboxylic congener (XCC) as selective antagonists at human $A_{2B}$ adenosine receptors", *Drug Dev. Res.* 47: 178-188 (1999).

Kim et al., "Anilide derivatives of an 8-phenylxanthine carboxylic congener are highly potent and selective antagonists at human $A_{2B}$ adenosine receptors", *J. Med. Chem.* 43: 1165-1172 (2000).

Klotz et al., "Comparative pharmacology of human adenosine receptor subtypes characterization of stably transfected receptors in CHO cells", *Naunyn-Schmied. Arch. Pharm.* 357:1-9 (1998).

Londos et al., "Subclasses of external adenosine receptors", *Proc. Natl. Acad. Sci. USA* 77: 2551-2554 (1980).

Marquardt et al., "Cloning of two adenosine receptor subtypes from mouse bone marrow derived mast cells", *J. Immunol.* 152: 4508-4515 (1994).

Mateo et al., "5-(N-Ethylcarboxamido)-adenosine inhibits $Ca^{2=}$ influx and activates a protein phosphatase in bovine adrenal chromaffin cells", *J. Neurochem.* 64: 77-84 (1995).

Murthy et al., "Adenosine $A_1$ and $A_{2B}$ receptors coupled to distinct interactive signaling pathways in intestinal muscle cells", *J. Pharmacol. Exp. Ther.* 274: 243-2-46 (1995).

Munson et al., "Ligand: a versatile computerized approach for the characterization of ligand binding systems", *Anal. Biochem.* 107: 220-239 (1980).

Varani et al., "[$^3$H]-SCH58261 labelling of functional $A_{2A}$ adenosine receptors in human neutrophil membranes", *Br. J. Pharmacol.* 123: 1723-1731 (1998).

Varani et al., "[$^3$H]-MRE3008F20: a novel antagonist radioligand for the pharmacological and biochemical characterization of human $A_3$ adenosine receptors", *Mol. Pharmacol.* 57: 968-975 (2000).

Zocchi et al., "Binding of the radioligand [$^3$H]-SCH58261, a new non-xanthine $A_{2A}$ adenosine receptor antagonist, to rat striatal membranes", *Br. J. Pharmacol.* 117: 1381-1386 (1996).

Mueller et al., "Synthesis of paraxanthine analogs (1,7-disubstituted xanthines) and other xanthines unsubstituted at the 3-position: structure-activity relationships at adenosine receptors", *J. Med. Chem.* 36: 3341-3349 (1993).

\* cited by examiner

8-HETEROARYL XANTHINE ADENOSINE $A_{2B}$ RECEPTOR ANTAGONISTS

RELATED APPLICATION

This application is a division of U.S. application Ser. No. 10/357,865 filed Feb. 3, 2003, now U.S. Pat. No. 7,205,403, which claims the benefit of U.S. Provisional Application No. 60/353,317, filed Feb. 1, 2002.

BACKGROUND OF THE INVENTION

The present invention relates to compounds having antagonistic activity on adenosine $A_{2B}$ receptors. Such compounds are useful in medicaments for treating diseases responsive to reduced levels of $A_{2B}$ receptors as well as use as radioligands for studying biological activity associated with the adenosine $A_{2B}$ receptor.

Adenosine (Ado) is an autocoid (or local hormone) that modulates numerous functions in the cardiovascular and other organ systems. The actions of Ado are mediated by at least four subtypes of cell surface receptors called $A_1$, $A_{2A}$, $A_{2B}$, and $A_3$. Because the ubiquity of adenosine receptors (AdoRs) throughout the body of a human, their indiscriminate activation may cause undesirable side effects. Therefore, new drug design approaches to achieve receptor and organ selectivity are needed.

Recently significant advancement has been made in the understanding of the molecular pharmacology and physiology of $A_{2B}$ adenosine receptors. However, due to the lack of highly potent and selective ligands for this receptor subtype, many questions about the patho-physiological role of $A_{2B}$ receptors have not yet been answered (Feoktistov and Biaggioni, 1997; Feoktistov and Biaggioni, 1998). $A_{2B}$ receptors have been implicated in the regulation of mast cell secretion (Feoktistov and Biaggioni 1995), gene expression (Boyle et al. 1996), cell growth (Dubey et al., 1996), intestinal functions (Murthy et al., 1995), neurosecretion (Mateo et al., 1995), vascular tone (Haynes et al., 1995) and asthma (Feoktistov et al., 1998).

U.S. Pat. No. 6,117,878 to Linden discloses the use of 8-phenyl substituted xanthines for the treatment of diseases induced by activation of the adenosine $A_{2B}$ receptor and mast cell activation. These disease states are disclosed as including asthma, myocardial reperfusion injury, allergic reactions including rhinitis, poison ivy induced responses, urticaria, scleroderma arthritis, other autoimmune diseases and inflammatory bowel diseases. In general, antagonists of the $A_{2B}$ adenosine receptor subtype are disclosed to have anti-inflammatory action. U.S. Pat. No. 6,117,878 to Linden is incorporated by reference.

U.S. Patent Application 2002/0002142 to Belardinelli et al. discloses the use of $A_{2B}$ adenosine receptor antagonist compounds for inhibiting mammalian cell proliferation in cells that express the $A_{2B}$ adenosine receptor including human retinal endothelial cells (HREC). Belardinelli discloses such treatment for ischemic injury to retinal vessels, for example, microvascular abnormalities of the retina, retinopathy, prematurity, macular degeneration, and diabetic retinopathy. U.S. Patent Application 2002/0002142 to Belardinelli et al. is incorporated by reference.

The use of $A_{2B}$ antagonists as antiasthmatic agents is supported by the experimental observation that theophylline and enprofylline are used as therapeutic agents (Feoktistov and Biaggioni 1997; Feoktistov et al., 1998). Theophylline is an alkyl-xanthine that is a weak nonselective adenosine antagonist (See Linden et al., *Cardiovascular Biology of Purines*, eds. G. Burnstock, et al., 1998, pp. 1-20.) However, its use is associated with unpleasant side effects, such as insomnia and diuresis. (See Vassallo et al., *Mayo. Clin. Proc.* 1998, 73, 346-354). In recent years, the use of theophylline as a bronchodilator, for relief of asthma, has been supplanted by drugs of other classes, i.e., selective $\beta_2$-adrenergic agonists, corticosteroids, and recently leukotriene antagonists. (See Drazen et al., *New Eng. J. Med.* 1999, 340, 197-206.). These compounds also have limitations, thus, the development of a theophylline-like drug with reduced side effects is still desirable.

It has been recognized that theophylline and its closely related analogue caffeine block endogenous adenosine acting as a local modulator of adenosine receptors in the brain and other organs at therapeutically useful doses. (See Fredholm et al., *Pharmacol. Rev.* 1999, 51, 83-133.). In comparison to the other known actions of theophylline, e.g., inhibition of phosphodiesterases, theophylline is more potent in antagonism of adenosine receptors.

As noted the xanthine derivative, enprofylline, is also used to treat asthma. Enprofylline has been reported to block $A_{2B}$ adenosine receptors. However, this compounds only weakly blocks $A_1$, $A_{2A}$ and $A_3$ adenosine receptors.

It has been reported that therapeutic concentrations of theophylline or enprofylline block human $A_{2B}$ receptors, and it has been proposed that antagonists selective for this subtype may have potential use as antiasthmatic agents. (See Feoktistov et al., *Pharmacol. Rev.* 1997, 49, 381-402; and Robeva et al., *Drug Dev. Res.* 1996, 39, 243-252. Enprofylline has a reported $K_i$ value of 7 μM and is somewhat selective in binding to human $A_{2B}$ adenosine receptors. (See Robeva et al., *Drug Dev. Res.* 1996, 39, 243-252 and Linden et al., *Vol. Pharmacol.* 1999, 56, 705-713.)

Adenosine $A_{2B}$ receptors are expressed in some mast cells, such as the BR line of canine mastocytoma cells, which appear to be responsible for triggering acute $Ca^{2+}$ mobilization and degranulation. (See Auchampach et al., *Mol. Pharmacol.* 1997, 52, 846-S60 and Forsyth et al., *Inflamm. Res.* 1999, 48, 301-307.) Adenosine $A_{2B}$ receptors also trigger $Ca^{2+}$ mobilization, and participate in a delayed IL8 release from human HMC-1 mast cells. Other functions associated with the $A_{2B}$ AR are the control of cell growth and gene expression, (See Neary et al., *Trends Neurosci.* 1996, 19, 13-18.) endothelial-dependent vasodilation (See Martin et al., *J Pharmacol. Exp. Ther.* 1993, 265, 248-2,53.), and fluid secretion from intestinal epithelia. (See Strohmeier, et al., *J Biol. Chem.* 1995, 270, 2387-2394.) Adenosine acting through $A_{2B}$ receptor subtype has also been reported to stimulate chloride permeability in cells expressing the cystic fibrosis transport regulator. (See Clancy et al., *Am. J Physiol.* 1999, 276, C361-C369.)

Both of these xanthine derivatives, enprofylline and theophylline, are proven to be effective but with low potency and selectivity at the $A_{2B}$ adenosine receptor subtype (theophylline $A_{2B}$ binding affinity $K_i$=13 μM; enprofylline $A_{2B}$ binding affinity $K_i$=7 μM).

Asthma is a complex disease involving the concerted actions of multiple inflammatory and immune cells, spasmogens, inflammatory mediators, cytokines and growth factors. Theophylline has significant side effects that may be related to its $A_1$ receptor antagonism. It is therefore believed that more potent and selective $A_{2B}$ receptor antagonists will provide enhanced asthma treatment.

The $A_1$, $A_{2A}$ and $A_3$ adenosine receptors have been pharmacologically characterized through the use of highly potent and selective agonists and/or antagonists. In contrast the study of $A_{2B}$ receptor has been precluded due to the lack of selective ligands. Researchers such as Jacobson and his coworkers have proposed using the radioligand of 7-amino-2-(2-4-furyl)-5-[2-(4-hydroxy-phenyl)ethyl]-amino[1,2,4]-triazolo-[1,5-a][1,3,5]-triazine ([$^3$H]-ZM241385) as useful radioligand for studying the $A_{2B}$ adenosine receptor subtype (Ji et al., 1999) even though [$^3$H]-ZM241385 has a $K_D$ value of 34 nM.

Jacobson and coworkers have also reported some xanthine derivatives endowed with good affinity to the adenosine receptors but without significant selectivity for the human $A_{2B}$ adenosine receptor subtype (Kim et al., 1999; Jacobson et al., 1999). Some non-xanthine derivatives closely related to ZM 241385 have also been synthesized, but, while some of the reported compounds displayed significant affinity to $A_{2B}$ receptors, none of them possessed relevant selectivity versus the other receptor subtypes $A_1$, $A_{2A}$ and $A_3$ (De Zwart et al., 1999).

Similarly, Jacobson and coworkers, with the aim of obtaining non-xanthine antagonists for $A_{2B}$ receptors, modified the structure of 5-amino-9-chloro-2-(2-furanyl)[1,2,4] triazolo-[1,5-c]-quinazoline (CGS 15943), a non selective adenosine receptor antagonist, which appeared to be a suitable starting compound for adenosine receptor antagonists by appropriate substitutions at different positions. In particular an improvement of affinity to $A_{2B}$ receptors was observed when aminoacidic chains are appended to the amino group of position 5 (Kim et al., 1998).

U.S. Pat. No. 5,935,964 to Baraldi et al. discloses triazolo pyrimidines have antagonist affinity for the $A_{2A}$ receptor. Using these compounds as a starting point, Baraldi et al. investigated a series of pyrazolo[4,3-e]1,2,4-triazolo-[1,5-c] pyrimidine compounds for use as $A_{2B}$ receptor antagonists. In particular the compounds with the free amino group at the 5-position, and for example, a phenylethyl chain at the N8 pyrazole nitrogen show good affinity to $A_{2B}$ adenosine receptors. However, none of these compounds demonstrated good selectivity (Baraldi et al., 2001).

Linden, Jacobson and coworkers have also reported a series of anilide derivatives of 8-phenyl-xanthine carboxylic congeners that proved to be potent and selective $A_{2B}$ antagonists (Kim et al., 2000; Ji et al., 2001) and S-substituted 1,3,7-trialkyl xanthine derivatives (U.S. Pat. No. 5,861,405 to Jacobson et al.) While many of the Linden and Jacobson compounds have high adenosine $A_{2B}$ potency, selectivity against other human adenosine receptors are in most cases limited (PCT patent application WO 00/73307 by Linden, Jacobson et al., 2000).

We have now discovered additional novel xanthine compounds having high antagonist affinity for the $A_{2B}$ receptor with varying levels of affinity and superior selectivity compared to compounds previously reported. The above noted references are incorporated herein by reference.

BRIEF SUMMARY OF THE INVENTION

Compounds useful as potent, yet selective modulators of adenosine receptors, with activity as adenosine $A_{2B}$ receptor antagonists, and, in some cases $A_1$ or $A_3$ antagonists, and methods of preparation and use thereof, are disclosed.

The compounds of the present invention have the following general formula (I):

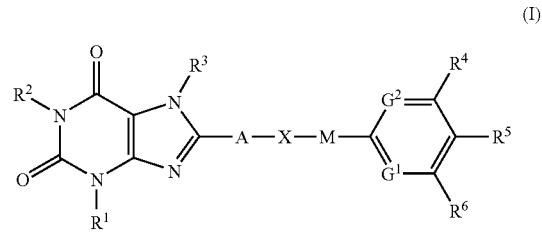

wherein $R^1$ and $R^2$ are independently hydrogen, ($C_1$ to $C_8$)alkyl, ($C_2$ to $C_8$)alkenyl, ($C_2$ to $C_8$)alkynyl, ($C_7$ to $C_{14}$)aralkyl, ($C_8$ to $C_{14}$)aralkenyl, or ($C_8$ to $C_{14}$)aralkynyl;

$R^3$ is hydrogen, ($C_1$ to $C_4$)alkyl, ($C_2$ to $C_5$)alkenyl, or ($C_2$ to $C_5$)alkynyl;

A is a carbon-carbon bond, alkyl chain of one to four carbons, alkenyl chain of two to four carbons, or alkynyl chain of two to four carbons;

X is an optionally substituted five or six-membered heteroaromatic ring, containing one to four heteroatoms, selected from nitrogen, oxygen, or sulfur, provided that at least one heteroatom is nitrogen;

M is a ($C_1$ to $C_8$)alkylene, ($C_2$ to $C_8$)alkenylene, or ($C_2$ to $C_8$)alkynylene, wherein at least one of the carbon atoms of the alkylene, alkenylene, or alkynylene group is present as a carbonyl, and one or more of the remaining carbon atoms of the alkylene, alkenylene, or alkynylene group may be replaced by —O—, —N($R^7$)—, —S—, —S(O)—, or —S(O)$_2$—;

$G^1$ and $G^2$ are independently CH or N;

$R^4$, $R^5$ and $R^6$ are independently hydrogen, ($C_1$ to $C_4$)alkyl, ($C_2$ to $C_5$)alkenyl, ($C_2$ to $C_5$)alkynyl, optionally substituted ($C_6$ to $C_{10}$)aryl, ($C_7$ to $C_{14}$)aralkyl, ($C_8$ to $C_{14}$) aralkenyl, or ($C_8$ to $C_{14}$)aralkynyl, acyl, optionally substituted alkoxy, aralkoxyalkylthio, amino, substituted amino, disubstituted amino, fluoro, chloro, bromo, iodo, nitro, cyano, azido, hydroxy, sulfhydryl, S(O)alkyl, S(O)$_2$alkyl, CO$_2$H, SO$_3$H; or taken together with the carbon atoms to which they are attached either $R^4$ and $R^5$ or $R^5$ and $R^6$ form a five or six-membered heterocyclic or heteroaromatic ring containing one to four hetereoatoms selected from nitrogen, oxygen, or sulfur; or taken together with the carbon atoms to which they are attached either $R^4$ and $R^5$ or $R^5$ and $R^6$ may independently form a carbocyclic or heterocyclic fused ring selected from the group of fused rings comprising —OCH$_2$O—, —OCH ($R^7$)O—, —OC($R^7$)$_2$O—, —OCH$_2$CH$_2$O—, OCH$_2$CH$_2$—, —CH$_2$CH$_2$O—, —OCH$_2$CH$_2$CH$_2$—, —CH$_2$CH$_2$CH$_2$O—, —OCH═CH—, —CH═CH—O—, —OCH═CH—, —CH═CH—CH═CH, —CH$_2$CH$_2$CH$_2$— and —CH$_2$CH$_2$CH$_2$CH$_2$—;

$R^7$ is hydrogen, ($C_1$ to $C_4$)alkyl, ($C_2$ to $C_5$) alkenyl, or ($C_2$ to $C_5$)alkynyl;

or a pharmaceutically acceptable salt thereof.

In another aspect this invention provides compounds of formula (I):

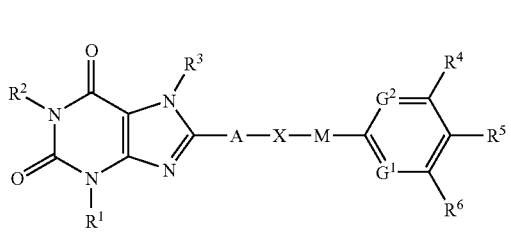

(I)

wherein

R$^1$ and R$^2$ are independently hydrogen, (C$_1$ to C$_8$)alkyl, (C$_2$ to C8)alkenyl, (C$_2$ to C$_8$)alkynyl, (C$_7$ to C$_{14}$)aralkyl, (C$_8$ to C$_{14}$)aralkenyl, or (C$_8$ to C$_{14}$)aralkynyl;

R$^3$ is hydrogen, (C$_1$ to C$_4$)alkyl, (C$_2$ to C$_5$)alkenyl, or (C$_2$ to C$_5$)alkynyl;

A is a carbon-carbon bond, alkyl chain of one to four carbons, alkenyl chain of two to four carbons, or alkynyl chain of two to four carbons;

X is a five or six-membered heteroaromatic ring, containing one to four heteroatoms, selected from nitrogen, oxygen, or sulfur, provided that at least one heteroatom is nitrogen, optionally substituted by one or two substituents selected from the group consisting of lower alkyl, amino, hydroxy, alkyloxy, acyloxy and acylamino;

M is a (C$_1$ to C$_8$)alkylene, (C$_2$ to C$_8$)alkenylene, or (C$_2$ to C$_8$)alkynylene, wherein at least one of the carbon atoms of the alkylene, alkenylene, or alkynylene group is present as a carbonyl, and one or more of the remaining carbon atoms of the alkylene, alkenylene, or alkynylene group may be replaced by —O—, —N(R$^7$)—, —S—, —S(O)—, —S(O)$_2$—; or a carbon substituted with a lower alkyl;

G$^1$ and G$^2$ are independently CH or N;

R$^4$, R$^5$ and R$^6$ are independently hydrogen, (C$_1$ to C$_4$)alkyl, (C$_2$ to C$_5$)alkenyl, (C$_2$ to C$_5$)alkynyl, optionally substituted (C$_6$ to C$_{10}$)aryl, (C$_7$ to C$_{14}$)aralkyl, (C$_8$ to C$_{14}$) aralkenyl, or (C$_8$ to C$_{14}$)aralkynyl, acyl, optionally substituted alkoxy, aralkoxyalkylthio, amino, substituted amino, disubstituted amino, fluoro, chloro, bromo, iodo, nitro, cyano, azido, hydroxy, sulfhydryl, S(O)alkyl, S(O)$_2$alkyl, CO$_2$H, SO$_3$H; or taken together with the carbon atoms to which they are attached either R$^4$ and R$^5$ or R$^5$ and R$^6$ form a five or six-membered heterocyclic or heteroaromatic ring containing one to four hetereoatoms selected from nitrogen, oxygen, or sulfur; or taken together with the carbon atoms to which they are attached either R$^4$ and R$^5$ or R$^5$ and R$^6$ form a carbocyclic or heterocyclic fused ring selected from the group of fused rings comprising —OCH$_2$O—, —OCH(R$^7$)O—, —OC(R$^7$)$_2$O—, —OCH$_2$CH$_2$O—, OCH$_2$CH$_2$—, —CH$_2$CH$_2$O—, —OCH$_2$CH$_2$CH$_2$—, —CH$_2$CH$_2$CH$_2$O—, —OCH=CH—, —CH=CH—O—, —O—CH=CH—O—, —CH=CH—CH=CH—, —CH$_2$CH$_2$CH$_2$— and —CH$_2$CH$_2$CH$_2$CH$_2$—;

R$^7$ is hydrogen, (C$_1$ to C$_4$)alkyl, (C$_2$ to C$_5$) alkenyl, or (C$_2$ to C$_5$)alkynyl;

or a pharmaceutically acceptable salt thereof.

In a further aspect, this invention provides compounds of the following formula (II):

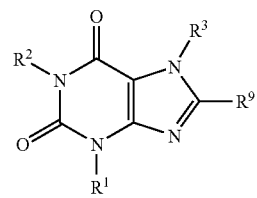

(II)

wherein

R$^1$ and R$^2$ are independently hydrogen, (C$_1$ to C$_8$)alkyl, (C$_2$ to C$_8$)alkenyl, (C$_2$ to C$_8$)alkynyl, (C$_7$ to C$_{14}$)aralkyl, (C$_8$ to C$_{14}$aralkenyl, or (C$_8$ to C$_{14}$)aralkynyl;

R$^3$ is H or (C$_1$ to C$_8$)alkyl;

R$^9$ is independently a phenyl or pyrazole ring; a phenyl or pyrazole ring substituted at any position with amino, lower alkyl, or carboxyl; or a phenyl or pyrazole ring substituted at any two positions with a substituent selected from amino, lower alkyl, and carboxyl; or R$^9$ is selected from the group consisting of

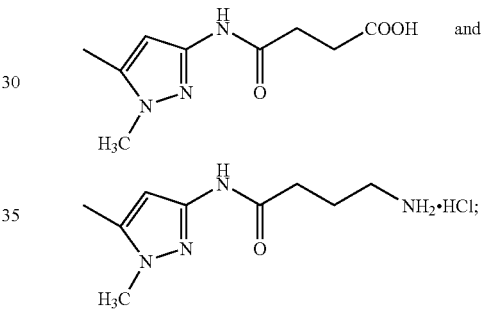

or a pharmaceutically acceptable salt thereof.

In yet another aspect, the invention provides compounds of formula (III):

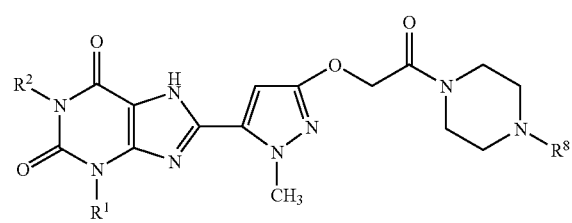

(III)

wherein

R$^1$ and R$^2$ are independently hydrogen, (C$_1$ to C$_8$)alkyl, (C$_2$ to C$_8$)alkenyl, (C$_2$ to C$_8$)alkynyl, (C$_7$ to C$_{14}$)aralkyl, (C$_8$ to C$_{14}$)aralkenyl, or (C$_8$ to C$_{14}$)aralkynyl;

R$^8$ is phenyl, substituted phenyl, (C, to C$_8$)alkyl, or benzyl;

or a pharmaceutically acceptable salt thereof

The compounds can be used in a method for the treatment of diseases mediated by adenosine A$_{2B}$ receptors. Such diseases include, but are not limited to chronic and acute inflammatory diseases involving degranulation of mast cells including asthma, chronic obstructive pulmonary disease, rheumatoid arthritis, allergic rhinitis, allergic dermatitis and bee sting; impaired sensitivity to insulin including Type 2 diabetes or non-insulin dependent diabetes, pre-diabetic state, and impaired glucose tolerance; diseases in which angiogenesis is a key component of pathogenesis including solid tumors and angiogenic retinopathies; and apnea of preterm infants; myocardial reperfusion injury, inflammatory bowel disease, and autoimmune diseases such as rheumatoid arthritis, multiple sclerosis (MS), and lupus erythematosis.

Similarly, the compounds can be used in a method for the treatment of diseases involving microvascular abnormalities of the retina that are mediated by adenosine $A_{2B}$ receptors. Such diseases include, but are not limited to, retinopathy, prematurity, macular degeneration, and diabetic retinopathy.

The compounds can be used in a pharmaceutical formulation that includes a compound of the present invention and one or more excipients. Various chemical intermediates can be used to prepare the compounds of the present invention.

DETAILED DESCRIPTION OF THE INVENTION

Figure 1:
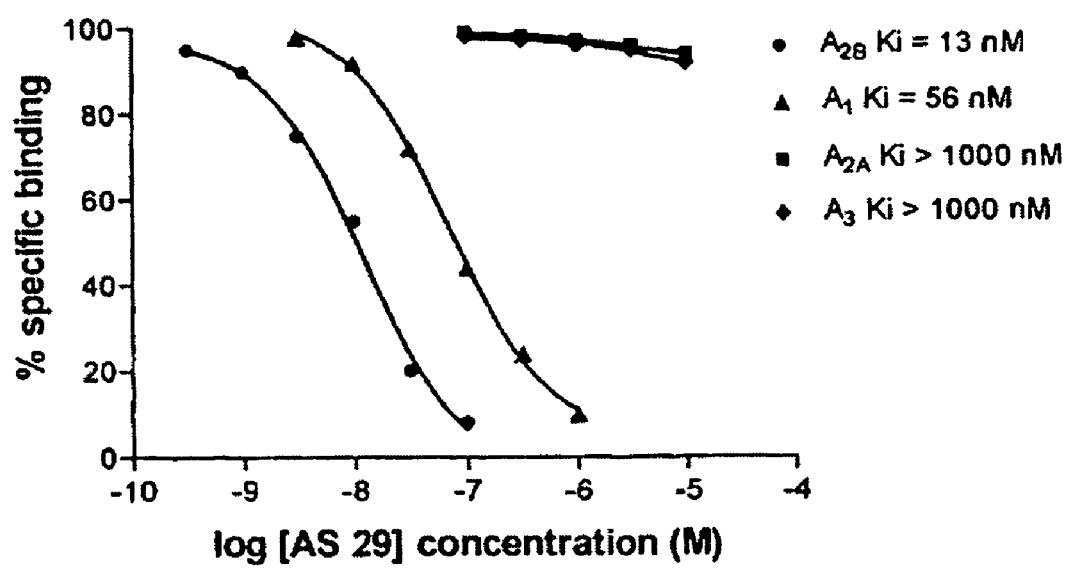
FIG. 1 illustrates competition binding curves for compound AS29 to human cloned $A_1$, $A_{2a}$, $A_{2b}$, and $A_3$ adenosine receptors.
Figure 2:
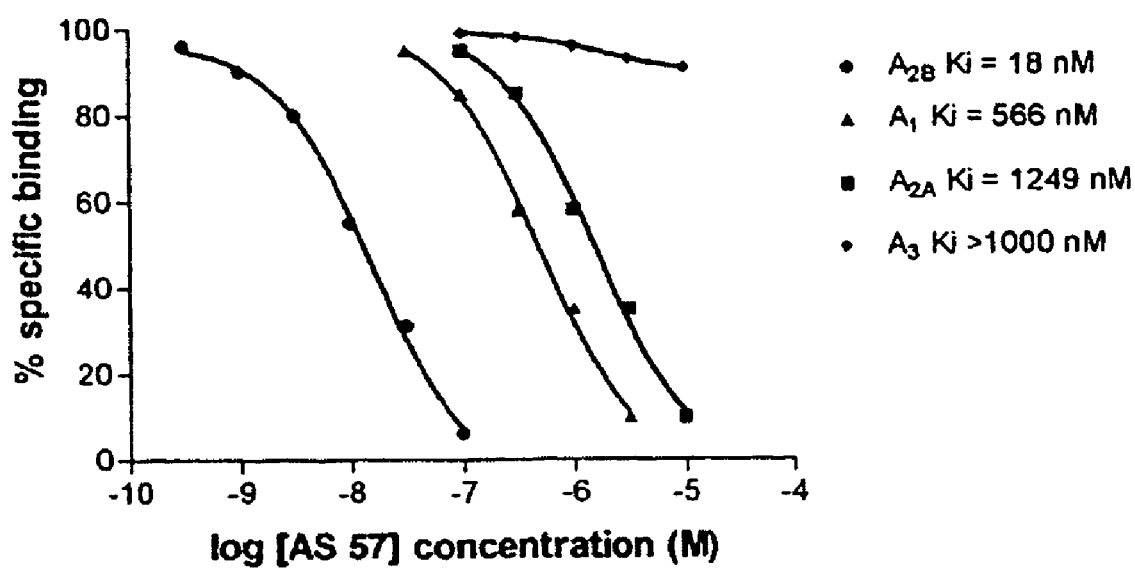
FIG. 2 illustrates competition binding curves for compound AS57 to human cloned $A_1$, $A_{2a}$, $A_{2b}$, and $A_3$ adenosine receptors.
Figure 3:
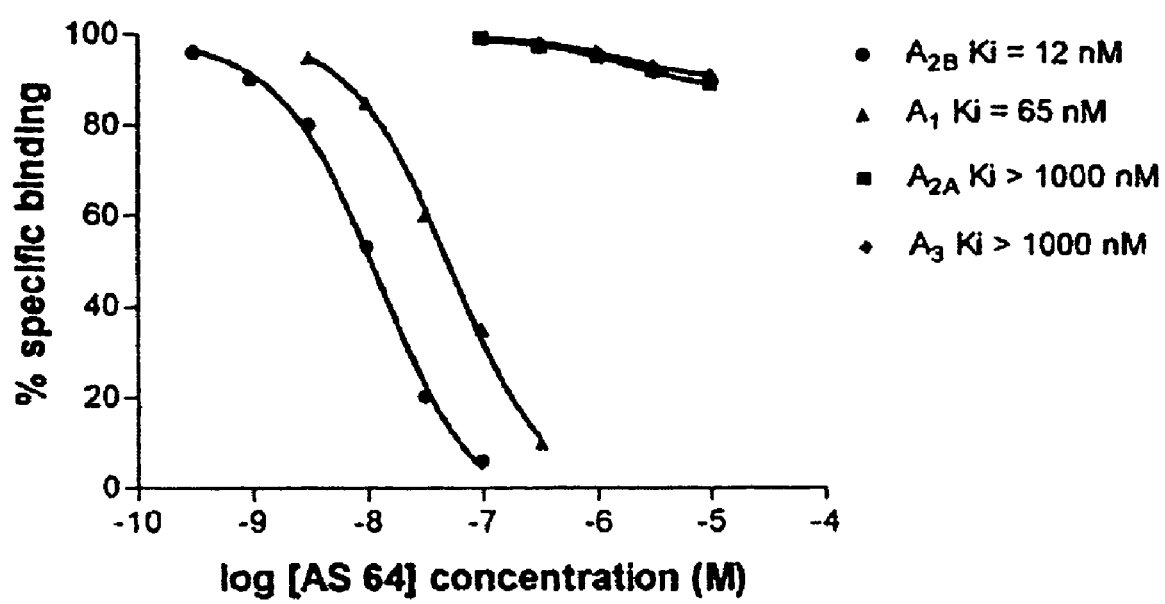
FIG. 3 illustrates competition binding curves for compound AS64 to human cloned $A_1$, $A_{2a}$, $A_{2b}$, and $A_3$ adenosine receptors.
Figure 4:
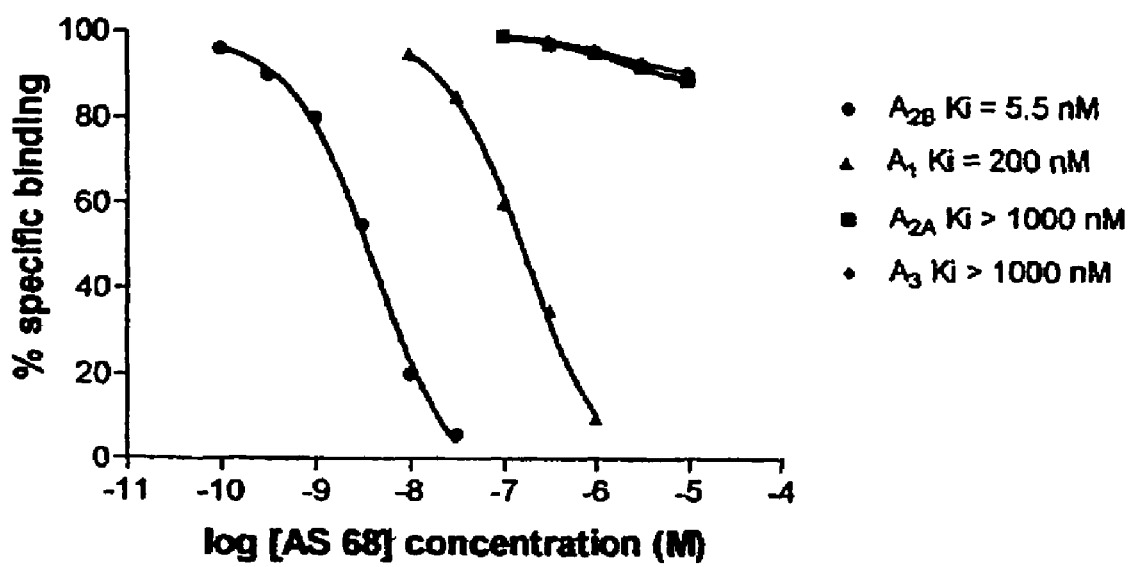
FIG. 4 illustrates competition binding curves for compound AS68 to human cloned $A_1$, $A_{2a}$, $A_{2b}$, and $A_3$ adenosine receptors.

The present application discloses compounds useful as potent, yet selective antagonists of adenosine receptors with particular utility with the adenosine $A_{2B}$ receptor subtype, methods of preparation and use thereof.

The compounds can be used in a pharmaceutical formulation that includes a compound of the present invention and one or more excipients. Various chemical intermediates can be used to prepare the compounds of the present invention.

The compounds of the present invention have the following general formula (I):

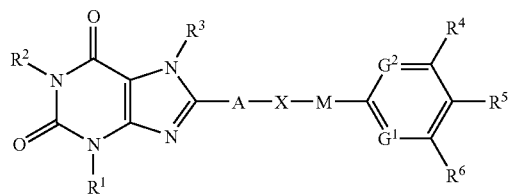

(I)

wherein
$R^1$ and $R^2$ are independently hydrogen, ($C_1$ to $C_8$)alkyl, ($C_2$ to $C_8$)alkenyl, ($C_2$ to $C_8$)alkynyl, ($C_7$ to $C_{14}$)aralkyl, ($C_8$ to $C_{14}$)aralkenyl, or ($C_8$ to $C_{14}$)aralkynyl;
$R^3$ is hydrogen, ($C_1$ to $C_4$)alkyl, ($C_2$ to $C_5$)alkenyl, or ($C_2$ to $C_5$)alkynyl;
A is a carbon-carbon bond, alkyl chain of one to four carbons, alkenyl chain of two to four carbons, or alkynyl chain of two to four carbons;
X is an optionally substituted five or six-membered heteroaromatic ring, containing one to four heteroatoms, selected from nitrogen, oxygen, or sulfur, provided that at least one heteroatom is nitrogen;
M is a ($C_1$ to $C_8$)alkylene, ($C_2$ to C8)alkenylene, or ($C_2$ to $C_8$)alkynylene, wherein at least one of the carbon atoms of the alkylene, alkenylene, or alkynylene group is present as a carbonyl, and one or more of the remaining carbon atoms of the alkylene, alkenylene, or alkynylene group may be replaced by —O—, —N($R^7$)—, —S—, —S(O)—, or —S(O)$_2$—;
$G^1$ and $G^2$ are independently CH or N;
$R^4$, $R^5$ and $R^6$ are independently hydrogen, ($C_1$ to $C_4$)alkyl, ($C_2$ to $C_5$)alkenyl, ($C_2$ to $C_5$)alkynyl, optionally substituted ($C_6$ to $C_{10}$)aryl, ($C_7$ to $C_{14}$)aralkyl, ($C_8$ to $C_{14}$)aralkenyl, or ($C_8$ to $C_{14}$)aralkynyl, acyl, optionally substituted alkoxy, aralkoxyalkylthio, amino, substituted amino, disubstituted amino, fluoro, chloro, bromo, iodo, nitro, cyano, azido, hydroxy, sulfhydryl, S(O)alkyl, S(O)$_2$alkyl, $CO_2H$, $SO_3H$; or
taken together with the carbon atoms to which they are attached either $R^4$ and $R^5$ or $R^5$ and $R^6$ form a five or six-membered heterocyclic or heteroaromatic ring containing one to four hetereoatoms selected from nitrogen, oxygen, or sulfur; or
taken together with the carbon atoms to which they are attached either $R^4$ and $R^5$ or $R^5$ and $R^6$ may independently form a carbocyclic or heterocyclic fused ring selected from the group of fused rings comprising —OCH$_2$O—, —OCH($R^7$)O—, —OC($R^7$)$_2$O—, —OCH$_2$CH$_2$O—, OCH$_2$CH$_2$—, —CH$_2$CH$_2$O—, —OCH$_2$CH$_2$CH$_2$—, —CH$_2$CH$_2$CH$_2$O—, —OCH=CH—, —CH=CH—O—, —O—CH=CH—O—, —CH=CH—CH=CH—, —CH$_2$CH$_2$CH$_2$— and —CH$_2$CH$_2$CH$_2$CH$_2$—;
$R^7$ is hydrogen, ($C_1$ to $C_4$)alkyl, ($C_2$ to $C_5$) alkenyl, or ($C_2$ to $C_5$)alkynyl;
or a pharmaceutically acceptable salt thereof.

In another aspect this invention provides compounds of formula (I):

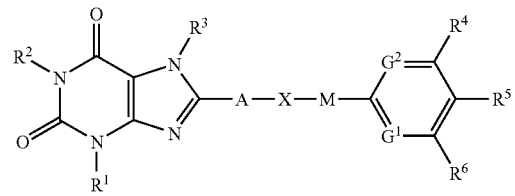

(I)

wherein
$R^1$ and $R^2$ are independently hydrogen, ($C_1$ to $C_8$)alkyl, ($C_2$ to $C_8$)alkenyl, ($C_2$ to $C_8$)alkynyl, ($C_7$ to $C_{14}$)aralkyl, ($C_8$ to $C_{14}$)aralkenyl, or ($C_8$ to $C_{14}$)aralkynyl;
$R^3$ is hydrogen, ($C_1$ to $C_4$)alkyl, ($C_2$ to $C_5$)alkenyl, or ($C_2$ to $C_5$)alkynyl;

A is a carbon-carbon bond, alkyl chain of one to four carbons, alkenyl chain of two to four carbons, or alkynyl chain of two to four carbons;

X is a five or six-membered heteroaromatic ring, containing one to four heteroatoms, selected from nitrogen, oxygen, or sulfur, provided that at least one heteroatom is nitrogen, optionally substituted by one or two substituents selected from the group consisting of lower alkyl, amino, hydroxy, alkyloxy, acyloxy and acylamino;

M is a ($C_1$ to $C_8$)alkylene, ($C_2$ to $C_8$)alkenylene, or ($C_2$ to $C_8$)alkynylene, wherein at least one of the carbon atoms of the alkylene, alkenylene, or alkynylene group is present as a carbonyl, and one or more of the remaining carbon atoms of the alkylene, alkenylene, or alkynylene group may be replaced by —O—, —N($R^7$)—, —S—, —S(O)—, —S(O)$_2$—; or a carbon substituted with a lower alkyl;

$G^1$ and $G^2$ are independently CH or N;

$R^4$, $R^5$ and $R^6$ are independently hydrogen, ($C_1$ to $C_4$)alkyl, ($C_2$ to $C_5$)alkenyl, ($C_2$ to $C_5$)alkynyl, optionally substituted ($C_6$ to $C_{10}$)aryl, ($C_7$ to $C_{14}$)aralkyl, ($C_8$ to $C_{14}$)aralkenyl, or ($C_8$ to $C_{14}$)aralkynyl, acyl, optionally substituted alkoxy, aralkoxyalkylthio, amino, substituted amino, disubstituted amino, fluoro, chloro, bromo, iodo, nitro, cyano, azido, hydroxy, sulfhydryl, S(O)alkyl, S(O)$_2$alkyl, $CO_2H$, $SO_3H$; or taken together with the carbon atoms to which they are attached either $R^4$ and $R^5$ or $R^5$ and $R^6$ form a five or six-membered heterocyclic or heteroaromatic ring containing one to four hetereoatoms selected from nitrogen, oxygen, or sulfur; or taken together with the carbon atoms to which they are attached either $R^4$ and $R^5$ or $R^5$ and $R^6$ form a carbocyclic or heterocyclic fused ring selected from the group of fused rings comprising —OCH$_2$O—, —OCH($R^7$)O—, —OC($R^7$)$_2$O—, —OCH$_2$CH$_2$O—, OCH$_2$CH$_2$—, —CH$_2$CH$_2$O—, —OCH$_2$CH$_2$CH$_2$—, —CH$_2$CH$_2$CH$_2$O—, —OCH=CH—, —CH=CH—O—, —O—CH=CH—O—, —CH=CH—CH=CH—, —CH$_2$CH$_2$CH$_2$— and —CH$_2$CH$_2$CH$_2$CH$_2$—;

$R^7$ is hydrogen, ($C_1$ to $C_4$)alkyl, ($C_2$ to $C_5$) alkenyl, or ($C_2$ to $C_5$)alkynyl;

or a pharmaceutically acceptable salt thereof.

In a further aspect, this invention provides compounds of the following formula (II):

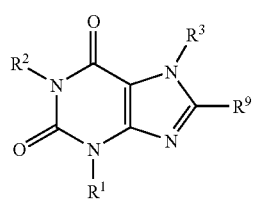

(II)

wherein $R^1$ and $R^2$ are independently hydrogen, ($C_1$ to $C_8$)alkyl, ($C_2$ to $C_8$)alkenyl, ($C_2$ to $C_8$)alkynyl, ($C_7$ to $C_{14}$)aralkyl, ($C_8$ to $C_{14}$)aralkenyl, or ($C_8$ to $C_{14}$)aralkynyl;

$R^3$ is H or ($C_1$ to $C_8$)alkyl;

$R^9$ is independently a phenyl or pyrazole ring; a phenyl or pyrazole ring substituted at any position with amino, lower alkyl, or carboxyl; or a phenyl or pyrazole ring substituted at any two positions with a substituent selected from amino, lower alkyl, and carboxyl; or $R^9$ is selected from the group consisting of

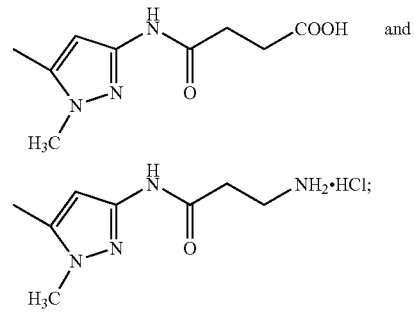

or a pharmaceutically acceptable salts thereof.

In yet another aspect, the invention provides compounds of formula (III):

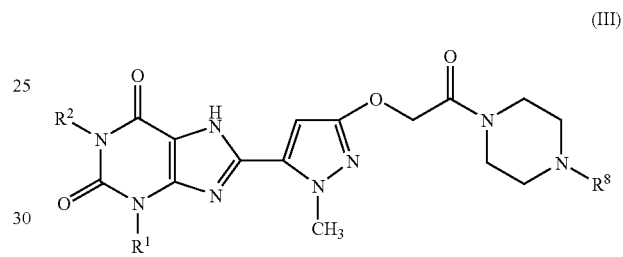

(III)

wherein $R^1$ and $R^2$ are independently hydrogen, ($C_1$ to $C_8$)alkyl, ($C_2$ to $C_8$)alkenyl, ($C_2$ to $C_8$)alkynyl, ($C_7$ to $C_{14}$)aralkyl, ($C_8$ to $C_{14}$)aralkenyl, or ($C_8$ to $C_{14}$)aralkynyl;

$R^8$ is phenyl, substituted phenyl, ($C_1$ to $C_8$)alkyl, or benzyl;

or a pharmaceutically acceptable salt thereof

As used herein the term "very potent adenosine $A_{2B}$ receptor antagonist" means a compound able to prevent the inhibition of an adenosine $A_{2B}$ receptor agonist and having a binding to human adenosine $A_{2B}$ receptor ($K_i$) of less than 2000 nM, preferably less than 150 nM, and most preferably less than 50 nM. The term "highly potent adenosine $A_{2B}$ receptor antagonist" means a very potent adenosine $A_{2B}$ receptor antagonist having a binding affinity to human adenosine $A_{2B}$ receptor ($K_i$) of less than 150 nM.

As used herein the term "highly selective adenosine $A_{2B}$ receptor antagonist" means a very potent adenosine $A_{2B}$ receptor antagonist having a binding affinity to human adenosine receptor subtypes $A_1$, $A_{2A}$ and $A_3$ ($K_i$) of greater than 1,000 nM.

As used herein the term "lower alkyl" means a monovalent radical, straight or branched chain, derived from the corresponding alkane having one to ten carbon atoms, i.e., methyl, ethyl, propyl, isopropyl, n-butyl, sec-butyl, t-butyl, pentyl (all isomers), etc. Likewise, "lower alkylene" means a divalent radical of the corresponding alkane. Further, as used herein, other moieties having names derived from alkanes, such as alkoxyl, alkanoyl, alkenyl, cycloalkenyl, etc. when modified by "lower," have carbon chains of ten or less carbon atoms. In those cases where the minimum number of carbons are greater than one, e.g., alkenyl (minimum of two carbons) and cycloalkyl, (minimum of three carbons), it is to be understood that "lower" means at least the minimum number of carbons.

As used herein the term "amino acid" means an alpha amino acid selected from those amino acids that naturally occur in proteins but without regard for specific stereochemical properties. The term "protected amino acid" means an amino acid of which the alpha amino group has been converted to a less reactive moiety, but a moiety that can be converted back to the amino group with relative ease. The terms "amino acid residue" and "amino acid moiety" are use synonymously herein.

As used herein, the term "substituted alkyl" refers to an alkyl group, preferably of from 1 to 10 carbon atoms ("substituted lower alkyl"), having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, keto, thioketo, carboxyl, carboxylalkyl, thiol, thioalkoxy, substituted thioalkoxy, aryl, aryloxy, heteroaryl, heteroaryloxy, heterocyclic, hydroxyamino, alkoxyamino, nitro, —S(O)-alkyl, —S(O)-substituted alkyl, —S(O)-aryl, —S(O)-heteroaryl, —S(O)$_2$-alkyl, —S(O)$_2$-substituted alkyl, —S(O)$_2$-aryl, —S(O)$_2$-heteroaryl, and mono- and di-alkylamino, mono- and di-(substituted alkyl)amino, mono- and di-arylamino, mono- and di-heteroarylamino, mono- and di-heterocyclic amino, and asymmetric di-substituted amines having different substituents selected from the group consisting of alkyl, aryl, heteroaryl and heterocyclic. As used herein, other moieties having, the prefix "substituted" are intended to include one or more of the substituents listed above.

As used herein, the term "alkoxy" refers to the group "alkyl-O—", where alkyl is as defined above. Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

As used herein, the term "alkenyl" refers to alkenyl groups preferably having from 2 to 10 carbon atoms and more preferably 2 to 6 carbon atoms and having at least 1 and preferably from 1-2 sites of alkenyl unsaturation. Preferred alkenyl groups include ethenyl (—CH=CH$_2$), n-propenyl (—CH$_2$CH=CH$_2$), iso-propenyl (—C(CH$_3$)=CH$_2$), and the like.

As used herein, the term "alkynyl" refers to alkynyl groups preferably having from 2 to 10 carbon atoms and more preferably 2 to 6 carbon atoms and having at least 1 and preferably from 1-2 sites of alkynyl unsaturation.

As used herein, the term "acyl" refers to the groups alkyl-C(O)—, substituted alkyl C(O)—, cycloalkyl-C(O)—, substituted cycloalkyl-C(O)—, aryl-C(O)—, substituted aryl-C(O)—, heteroaryl-C(O)— and heterocyclic-C(O)— where alkyl, substituted alkyl, cycloalkyl, substituted cycloalkyl, aryl, heteroaryl and heterocyclic are as defined herein.

As used herein, the term "acylamino" refers to the group —C(O)NRR where each R is independently hydrogen, alkyl, substituted alkyl, aryl, substituted aryl, heteroaryl, or heterocyclic, wherein alkyl, substituted alkyl, aryl, heteroaryl and heterocyclic are as defined herein.

As used herein, the term "aryl" refers to an unsaturated aromatic carbocyclic group of from 6 to 14 carbon atoms having a single ring, (e.g., phenyl) or multiple condensed (fused) rings (e.g., naphthyl or anthryl). Preferred aryls include phenyl, naphthyl and the like. Unless otherwise constrained by the definition for the aryl substituent, such aryl groups can optionally be substituted with from 1 to 5 substituents and preferably 1 to 3 substituents selected from the group consisting of acyloxy, hydroxy, acyl, alkyl, alkoxy, alkenyl, alkynyl, substituted alkyl, substituted alkoxy, substituted alkenyl, substituted alkynyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —S(O)-alkyl, —S(O)-substituted alkyl, —S(O)-aryl, —S(O)-heteroaryl, —S(O)$_2$-alkyl, —S(O)$_2$-substituted alkyl, —S(O)$_2$-aryl, —S(O)$_2$-heteroaryl, trihalomethyl. Preferred substituents include alkyl, alkoxy, halo, cyano, nitro, trihalomethyl, and thioalkoxy.

As used herein, the term "cycloalkyl" refers to cyclic alkyl groups of from 3 to 12 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantyl, and the like.

As used herein, the terms "halo" or "halogen" refers to fluoro, chloro, bromo and iodo and preferably is fluoro, bromo or chloro.

As used herein, the term "heteroaryl" refers to an aromatic carbocyclic group of from 1 to 15 carbon atoms and 1 to 4 heteroatoms selected from the group consisting of oxygen, nitrogen and sulfur within at least one ring (if there is more than one ring).

Unless otherwise constrained by the definition for the heteroaryl substituent, such heteroaryl groups can be optionally substituted with from 1 to 5 substituents and preferably 1 to 3 substituents selected from the group consisting of acyloxy, hydroxy, acyl, alkyl, alkoxy, alkenyl, alkynyl, substituted alkyl, substituted alkoxy, substituted alkenyl, substituted alkynyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —S(O)-alkyl, —S(O)-substituted alkyl, —S(O)-aryl, —S(O)-heteroaryl, —S(O)$_2$-alkyl, —S(O)$_2$-substituted alkyl, —S(O)$_2$-aryl, —S(O)$_2$-heteroaryl, trihalomethyl. Preferred substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl).

"Heterocycle" or "heterocyclic" refers to a monovalent saturated or unsaturated carbocyclic group having a single ring or multiple condensed rings, from 1 to 15 carbon atoms and from 1 to 4 hetero atoms selected from the group consisting of nitrogen, sulfur or oxygen within the ring. Such heterocyclic groups are optionally substituted with 1 to 5 substituents selected from the group consisting of alkyl, substituted alkyl, alkoxy, substituted alkoxy, aryl, aryloxy, halo, nitro, heteroaryl, thiol, thioalkoxy, substituted thioalkoxy, thioaryloxy, trihalomethyl, and the like. Such heterocyclic groups can have a single ring or multiple condensed rings.

As to any of the above groups that contain 1 or more substituents, it is understood, that such groups do not contain any substitution or substitution patterns which are sterically impractical and/or synthetically non-feasible.

"Pharmaceutically acceptable salts" refers to pharmaceutically acceptable salts of a compound of the general formula of the present invention, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like can be used as the pharmaceutically acceptable salt.

The term "protecting group" or "blocking group" refers to any group which when bound to one or more hydroxyl, amino or carboxyl groups of the compounds (including intermediates thereof such as the aminolactams, aminolactones, etc.) prevents reactions from occurring at these groups and which protecting group can be removed by conventional chemical or enzymatic steps to reestablish the hydroxyl, amino or carboxyl group. Preferred removable amino blocking groups include conventional substituents such as t-butyoxycarbonyl (t-BOC), benzyloxycarbonyl (CBZ), and the like which can be removed by conventional conditions compatible with the nature of the product.

Those skilled in the art of organic chemistry will appreciate that reactive and fragile functional groups often must be protected prior to a particular reaction, or sequence of reactions, and then restored to their original forms after the last reaction is completed. Usually groups are protected by converting them to a relatively stable derivative. For example, a hydroxyl group may be converted to an ether group and an amino converted to an amide or carbamate. Methods of protecting and de-protect, also know as "blocking" and "de-blocking," are well know and widely practiced in the art, e.g., see T. Green, Protective Groups in Organic Synthesis, John Wiley, New York (1981) or Protective Groups in Organic Chemistry, Ed. J. F. W. McOmie, Plenum Press, London (1973).

Representative example compounds include:

| Compound Number | Compound Name |
|---|---|
| AS3 | 8-(3-amino-1-methyl-1H-pyrazol-5-yl)-1,3-dipropyl-3,7-dihydro-1H-purine-2,6-dione |
| AS4 | [3-(2,6-dioxo-1,3-dipropyl-2,3,6,7-tetra-hydro-1H-purin-8-yl)isoxazol-5-yl]methyl-benzoate |
| AS7 | 8-(1-methyl-4-nitro-1H-pyrrol-2-yl)-1,3-dipropyl-3,7-dihydro-1H-purine-2,6-dione |
| AS8 | 4-{[5-(1,3-dipropyl-2,6-dioxo-2,3,6,7-tetrahydro-1H-pur-in-8-yl)-1-methyl-1H-pyrazol-3-yl]amino}-4-oxobutanoic acid |
| AS9 | tert-butyl 4-{[5-(2,6-dioxo-1,3-dipropyl-2,3,6,7-tetrahydro-1H-purin-8-yl)-1-methyl-1H-pyrazol-3-yl]amino}-4-oxobutylcarbamate |
| AS10 | 4-{[5-(2,6-dioxo-1,3-dipropyl-2,3,6,7-tetrahydro-1H-purin-8-yl)-1-methyl-1H-pyrazol-3-yl]amino}-4-oxobutan-1-aminium chloride |
| AS11 | N-[5-(2,6-dioxo-1,3-dipropyl-2,3,6,9-tetrahydro-1H-purin-8-yl)-1-methyl-1H-pyrazol-3-yl]-2-phenylacetamide |
| AS12 | 2-(2,4-dichlorophenoxy)-N-[5-(2,6-dioxo-1,3-dipropyl-2,3,6,7-tetrahydro-1H-purin-8-yl)-1-methyl-1H-pyrazol-3-yl]acetamide |
| AS13 | 2-(3-methoxyphenyl)-N-[5-(2,6-dioxo-1,3-dipropyl-2,3,6,9-tetrahydro-1H-purin-8-yl)-1-methyl-1H-pyrazol-3-yl]acetamide |
| AS14 | N-[5-(2,6-dioxo-1,3-dipropyl-2,3,6,9-tetrahydro-1H-purin-8-yl)-1-methyl-1H-pyrazol-3-yl]-2-(4-isobutylphenyl)acetamide |
| AS15 | N-[5-(2,6-dioxo-1,3-dipropyl-2,3,6,9-tetrahydro-1H-purin-8-yl)-1-methyl-1H-pyrazol-3-yl]-2-(4-nitrophenyl)acetamide |
| AS16 | 2-[4-benzyloxyphenyl]-N-[5-(2,6-dioxo-1,3-dipropyl-2,3,6,9-tetrahydro-1H-purin-8-yl)-1-methyl-1H-pyrazol-3-yl]acetamide |
| AS17 | 2-[4-hydroxyphenyl]-N-[5-(2,6-dioxo-1,3-dipropyl-2,3,6,9-tetrahydro-1H-purin-8-yl)-1-methyl-1H-pyrazol-3-yl]acetamide |
| AS18 | (2S)-N-[5-(2,6-dioxo-1,3-dipropyl-2,3,6,7-tetrahydro-1H-purin-8-yl)-1-methyl-1H-pyrazol-3-yl]-2-phenylpropanamide |
| AS19 | (2R)-N-[5-(2,6-dioxo-1,3-dipropyl-2,3,6,7-tetrahydro-1H-purin-8-yl)-1-methyl-1H-pyrazol-3-yl]-2-phenylpropanamide |
| AS20 | {3-[(E)-2-(1,3-dipropyl-7-methyl-2,6-dioxo-2,3,6,7-tetrahydro-1H-purin-8-yl)vinyl]isoxazol-5-yl}methyl benzoate |
| AS21 | 2-(4-chlorophenoxy)-N-[5-(1,3-dipropyl-2,6-dioxo-2,3,6,7-tetrahydro-1H-purin-8-yl)-1-methyl-1H-pyrazol-3-yl]acetamide |
| AS22 | N-[5-(2,6-dioxo-1,3-dipropyl-2,3,6,9-tetrahydro-1H-purin-8-yl)-1-methyl-1H-pyrazol-3-yl]-2-(4-fluorophenyl)acetamide |
| AS23 | 2-(4-methoxyphenyl)-N-[5-(2,6-dioxo-1,3-dipropyl-2,3,6,9-tetrahydro-1H-purin-8-yl)-1-methyl-1H-pyrazol-3-yl]acetamide |
| AS24 | N-[5-(2,6-dioxo-1,3-dipropyl-2,3,6,9-tetrahydro-1H-purin-8-yl)-1-methyl-1H-pyrazol-3-yl]-2-(3-chlorophenyl)acetamide |
| AS25 | N-[5-(2,6-dioxo-1,3-dipropyl-2,3,6,9-tetrahydro-1H-purin-8-yl)-1-methyl-1H-pyrazol-3-yl]-2-(3-fluorophenyl)acetamide |
| AS26 | N-[5-(2,6-dioxo-1,3-dipropyl-2,3,6,9-tetrahydro-1H-purin-8-yl)-1-methyl-1H-pyrazol-3-yl]-2-[4-(N,N-dimethylamino)phenyl]acetamide |
| AS27 | N-[5-(2,6-dioxo-1,3-dipropyl-2,3,6,9-tetrahydro-1H-purin-8-yl)-1-methyl-1H-pyrazol-3-yl]-2-(4-chlorophenyl)acetamide |
| AS28 | 2-(3,4-dimethoxyphenyl)-N-[5-(2,6-dioxo-1,3-dipropyl-2,3,6,9-tetrahydro-1H-purin-8-yl)-1-methyl-1H-pyrazol-3-yl]acetamide |
| AS29 | N-[5-(2,6-dioxo-1,3-dipropyl-2,3,6,9-tetrahydro-1H-purin-8-yl)-1-methyl-1H-pyrazol-3-yl]-2-(4-{[2-(trifluoromethyl)benzyl]oxy}phenyl)acetamide |
| AS30 | N-[5-(2,6-dioxo-1,3-dipropyl-2,3,6,9-tetrahydro-1H-purin-8-yl)-1-methyl-1H-pyrazol-3-yl]-2-(4-{[3-(trifluoromethyl)benzyl]oxy}phenyl)acetamide |

-continued

| Compound Number | Compound Name |
|---|---|
| AS31 | N-[5-(2,6-dioxo-1,3-dipropyl-2,3,6,9-tetrahydro-1H-purin-8-yl)-1-methyl-1H-pyrazol-3-yl]-2-(4-{4-nitro-benzyloxy}phenyl)acetamide |
| AS32 | N-[5-(2,6-dioxo-1,3-dipropyl-2,3,6,9-tetrahydro-1H-purin-8-yl)-1-methyl-1H-pyrazol-3-yl]-2-[4-(trifluoromethyl)phenyl]acetamide |
| AS33 | ethyl 4-[(E)-2-(7-methyl-1,3-dipropyl-2,6-dioxo-2,3,6,7-tetrahydro-1H-purin-8-yl)vinyl]-1-methyl-1H-pyrrole-2-carboxylate |
| AS35 | N-[5-(2,6-dioxo-1,3-dipropyl-2,3,6,9-tetrahydro-1H-purin-8-yl)-1-methyl-1H-pyrazol-5-yl]-2-phenylacetamide |
| AS36 | 8-(1-methyl-3-nitro-1H-pyrazol-5-yl)-1,3-dipropyl-3,7-dihydro-1H-purine-2,6-dione |
| AS37 | 8-(5-amino-1-methyl-1H-pyrazol-3-yl)-1,3-dipropyl-3,7--dihydro-1H-purine-2,6-dione |
| AS38 | 8-(3-amino-1-methyl-1H-pyrazol-5-yl)-1,3-dimethyl-3,7-dihydro-1H-purine-2,6-dione |
| AS40 | N-[5-(2,6-dioxo-1,3-dimethyl-2,3,6,9-tetrahydro-1H-purin-8-yl)-1-methyl-1H-pyrazol-3-yl]-2-phenylacetamide |
| AS43 | N-[5-(2,6-dioxo-1,3-dipropyl-2,3,6,9-tetrahydro-1H-purin-8-yl)-1-methyl-1H-pyrazol-3-yl]-2-(3,4-difluorophenyl)acetamide |
| AS44 | 2-(2,3,4-trimethoxyphenyl)-N-[5-(2,6-dioxo-1,3-dipropyl-2,3,6,9-tetrahydro-1H-purin-8-yl)-1-methyl-1H-pyrazol-3-yl]acetamide |
| AS53 | N-[4-(dimethylamino)phenyl]-N'-[5-(2,6-dioxo-1,3-dipropyl-2,3,6,7-tetrahydro-1H-purin-8-yl)-1-methyl-1H-pyrazol-3-yl]urea |
| AS54 | N-(3-chlorophenyl)-N'-[5-(2,6-dioxo-1,3-dipropyl-2,3,6,7-tetrahydro-1H-purin-8-yl)-1-methyl-1H-pyrazol-3-yl]urea |
| AS55 | N-[5-(2,6-dioxo-1,3-dipropyl-2,3,6,7-tetrahydro-1H-purin-8-yl)-1-methyl-1H-pyrazol-3-yl]-N'-(3-methoxyphenyl)urea |
| AS56 | 2-[4-(benzyloxy)-3-methoxyphenyl]-N-[5-(2,6-dioxo-1,3-dipropyl-2,3,6,9-tetrahydro-1H-purin-8-yl)-1-methyl-1H-pyrazol-3-yl]acetamide |
| AS57 | 2-(1,3-benzodioxol-5-yl)-N-[5-(2,6-dioxo-1,3-dipropyl-2,3,6,9-tetrahydro-1H-purin-8-yl)-1-methyl-1H-pyrazol-3-yl]acetamide |
| AS58 | N-[5-(2,6-dioxo-1,3-dipropyl-2,3,6,9-tetrahydro-1H-purin-8-yl)-1-methyl-1H-pyrazol-3-yl]-2-(4-hydroxy-3-methoxyphenyl)acetamide |
| AS59 | N-(4-methylphenyl)-2-{[5-(1,3-dipropyl-2,6-dioxo-2,3,6,7-tetrahydro-1H-purin-8-yl)-1-methyl-1H-pyrazol-3-yl]oxy}acetamide |
| AS60 | N-(4-bromophenyl)-2-{[3-(2,6-dioxo-1,3-dipropyl-2,3,6,9-tetrahydro-1H-purin-8-yl)-1-methyl-1H-pyrazol-5-yl]oxy}acetamide |
| AS61 | N-(4-fluorophenyl)-2-{[3-(2,6-dioxo-1,3-dipropyl-2,3,6,9-tetrahydro-1H-purin-8-yl)-1-methyl-1H-pyrazol-5-yl]oxy}acetamide |
| AS62 | 2-{[3-(1,3-diisobutyl-2,6-dioxo-2,3,6,9-tetrahydro-1H-purin-8-yl)-1-methyl-1H-pyrazol-5-yl]oxy}-N-(4-fluorophenyl)acetamide |
| AS63 | 2-{[3-(1,3-diisobutyl-2,6-dioxo-2,3,6,9-tetrahydro-1H-purin-8-yl)-1-methy-1-1H-pyrazol-5-yl]oxy}-N-(4-bromophenyl)acetamide |
| AS64 | 2-{[5-(2,6-dioxo-1,3-dipropyl-2,3,6,9-tetrahydro-1H-purin-8-yl)-1-methyl-1H-pyrazol-3-yl]oxy}-N-(4-fluorophenyl)acetamide |
| AS65 | 2-{[5-(2,6-dioxo-1,3-dipropyl-2,3,6,9-tetrahydro-1H-purin-8-yl)-1-methyl-1H-pyrazol-3-yl]oxy}-N-(4-bromophenyl)acetamide |
| AS66 | 2-{[5-(1,3-diisobutyl-2,6-dioxo-2,3,6,9-tetrahydro-1H-purin-8-yl)-1-methy-1-1H-pyrazol-3-yl]oxy}-N-(4-fluorophenyl)acetamide |
| AS67 | 2-{[5-(1,3-diisobutyl-2,6-dioxo-2,3,6,9-tetrahydro-1H-purin-8-yl)-1-methy-1-1H-pyrazol-3-yl]oxy}-N-(4-bromophenyl)acetamide |
| AS68 | N-1,3-benzodioxol-5-yl-2-{[5-(2,6-dioxo-1,3-dipropyl-2,3,6,9-tetrahydro-1H-purin-8-yl)-1-methyl-1H-pyrazol-3-yl]oxy}acetamide |
| AS69 | 2-{[5-(2,6-dioxo-1,3-dipropyl-2,3,6,9-tetrahydro-1H-purin-8-yl)-1-methyl-1H-pyrazol-3-yl]oxy}-N-(4-methoxyphenyl)acetamide |
| AS1 | 1,3-di-n-propyl-8-(1-methyl-5-carboxy-1-H-pyrazol-3-yl)-xanthine |
| AS49 | 1-[5-(2,6-Dioxo-1,3-dipropyl-2,3,6,7-tetrahydro-1H-purin-8-yl)-1-methyl-1H-pyrazol-3-yl]-3-(4-methoxy-phenyl)-urea |
| AS91 | 1,3-di-n-propyl-8-{5-[(4-sec-butyl-phenylcarbamoyl)-methoxy]-2-methyl-2H-pyrazole-3-yl} |
| AS92 | 1,3-di-n-propyl-8-{5-[(4-methyl-phenylcarbamoyl-methoxy]-2-methyl-2H-pyrazole-3-yl}-xanthine |
| AS93 | 1,3-di-n-propyl-8-{5-[(4-(morpholine-4-yl)-phenylcarbamoyl]-methoxy]-2-methyl-2H-pyrazole-3-yl}-xanthine |
| AS95 | 1,3-di-n-propyl-8-{5-[(4-carboxy-phenylcarbamoyl)-methoxy]-2-methyl-2H-py-razole-3-yl}-xanthine |
| AS99 | 1,3-di-n-propyl-8-{5-[(3,4-dime-thyl-phenylcarbamoyl)-methoxy]-2-methyl-2H-pyrazole-3-yl}-xanthine |
| AS100 | 1,3-di-n-propyl-8-{5-[(3,4-dimethyl-phenylcar-bamoyl)-methoxy]-2-methyl-2H-pyrazole-3-yl}-xanthine |
| AS101 | 1,3-di-n-propyl-8-{5-[(3,4-dimethoxy-phenylcarbamoyl)-methoxy]-2-methyl-2H-pyrazole-3-yl}-xanthine |
| AS89 | 1,3-di-n-propyl-8-{5-[(pyri-din-4yl)-methoxy]-2-methyl-2H-pyrazole-3-yl}-xanthine |
| AS70 | 1,3-di-n-propyl-8-{5-[2-oxo-2-(4-phenyl-piperazin-1-yl)-ethoxy]-2-methyl-2H-pyrazole-3-yl}-xanthine |

-continued

| Compound Number | Compound Name |
|---|---|
| AS72 | 8-(5-{2-[4-(4-Fluoro-pheny-1)-piperazin-1-yl]-2-oxo-ethoxy}-2-methyl-2H-pyrazol-3-yl)-1,3-dipropyl-3,7-dihydro-purine-2,6-dione |
| AS87 | 1,3-di-n-propyl-8-{5-[2-Oxo-2-(4-methyl-piperazin-1-yl)-ethoxy]-2-methyl-2H-pyrazole-3-yl}-xanthine |
| AS90 | 8-(5-{2-[4-(4-Benzyl-pheny-1)-piperazin-1-yl]-2-oxo-ethoxy}-2-methyl-2H-pyrazol-3-yl)-1,3-dipropyl-3,7-dihydro-purine-2,6-dione |
| AS96 | 1,3-di-allyl-8-{5-[2-oxo-2-(4-phenyl-piperazin-1-yl)-ethoxy]-2-methyl-2H-pyrazole-3-yl}-xanthine |
| AS74 | 1,3-di-n-propyl-8-{3-[(3,4-me-thylendioxy-phenylcarbamoyl)-methoxy]-isoxazol-5-yl}-xanthine |
| AS76 | 1,3-di-n-propyl-8-{3-[(3,4-dimethoxy-phenylcarbamoyl)-methoxy]-isoxazol-5-yl}-xanthine |
| AS73 | 1,3-di-n-propyl-8-{3-[(4-fluoro--phenylcarbamoyl)-methoxy]-isoxazol-5-yl}-xanthine |
| AS75 | 1,3-di-n-propyl-8-{3-[(4-methoxy-phenylcarbamoyl)-methoxy]-isoxazol-5-yl}-xanthine |
| AS81 | 1,3-di-n-propyl-8-{6-[(4-iodo-phenylcarbamoyl)-metho-xy]-pyridin-3-yl}-xanthine |
| AS85 | 1,3-di-n-propyl-8-{6-[(4-iodo-pheny-lcarbamoyl)-methoxy]-pyridazin-3-yl}-xanthine |
| AS68a | N-1,3-benzodioxol-5-yl-2-{[5-(2,6-dioxo-1,3-diallyl-2,3,6,9-tetrahydro-1H-purin-8-yl)-1-methyl-1H-pyrazol-3-yl]oxy}acetamide |
| AS94 | 1,3-di-n-propyl-8-{5-[(4-(ethoxycarbonyl)-phenylcarbamoyl)-methoxy]-2-met-hyl-2H-pyrazole-3-yl}-xanthine |
| AS103 | 1,3-di-n-propyl-8-(2-hydroxypyridin-5-yl)-xanthine |
| AS105 | 1,3-diallyl-8-{5-[2-oxo-2-(4-(pyridin-2-yl)-piperazin-1-yl)-ethoxy]-2-met-hyl-2H-pyrazole-3-yl}-xanthine |
| AS106 | 1,3-diallyl-8-{5-[2-oxo-2-(4-(pyrimidin-2-yl)-piperazin-1-yl)-ethoxy]-2-m-ethyl-2H-pyrazole-3-yl}-xanthine |
| AS109 | 1,3-di-n-propyl-8-{5-[(4-(aminosulfonyl)phenylcarbamoyl)-methoxy]-2-methy-1-2H-pyrazole-3-yl}-xanthine |

Synthesis of Compounds

The compounds of the present invention may be synthesized by any suitable means. However, the 8-heteroaryl-xanthine derivatives of the present invention are preferably synthesized by condensation of a suitably substituted heteroaryl-carboxylic acid with a 1,3-disubstituted-5,6-diaminouracil to form an amide, which is subsequently cyclized to give a 1,3-disubstituted-8-heteroaryl-xanthine.

If desired, reaction of this product under conditions commonly employed by one skilled in the art would provide additional compounds of the present invention. For example, 1,3-disubstituted-8-heteroaryl-xanthines containing a primary amine on the heteroaryl moiety could be further reacted with an appropriate carboxylic acid, acid halide, carboxylic acid ester, or isocyanate under conditions widely known to those skilled in the art to provide the corresponding amides or ureas of the present invention.

Similarly, the 1,3-disubstituted-8-heteroaryl-xanthines containing a hydroxyl group attached to the heteroaryl moiety might be reacted with a suitable acyl ester, acid halide, α-halocarbonyl compound, isocyanate, sulfinyl halide or sulfonyl halide to afford the respective ester, β-oxycarbonyl compound, carbamate, sulfinate, or sulfonate. A further example can be seen in which a 1,3-disubstituted-8-heteroaryl-xanthine containing a carboxylic acid attached to the heteroaryl moiety may be reacted with an appropriate aniline, heteroarylamine, alkylamine, or aralkylamine to afford the corresponding amide.

It will be recognized by one skilled in the art that numerous other possibilities are conceivable in the substituent attached to the heteroaryl moiety and the functional group it is reacted with. It will also be recognized that the suggested additional reactions are not exhaustive, but merely illustrative.

In general, the compounds of the present invention are prepared as depicted in the accompanying schemes. As shown in Scheme 1, a 1,3-disubstituted-5,6-diaminouracil (Compound 2) may be dissolved in an appropriate volume of a lower alcohol with an appropriate heteroaryl carboxylic acid (Compound 3) and a suitable coupling agent, such as 3-ethyl-1-(3-dimethylaminopropyl)-3-ethylcarbodiimide hydrochloride (EDCI) or 1,3-dicyclohexylcarbodiimide (DCC), at a temperature of 5 to 70° C., for a period of 1 to 24 hours.

After removing the residual solvent, the intermediate amide is treated with an excess of an aqueous basic solution, such as sodium hydroxide or potassium hydroxide at a temperature of 30 to 100° C. for 1 to 12 hours to afford the desired 8-(aminoheteroaryl)-1,3-disubstituted-xanthine (Compound 4).

Scheme 1:

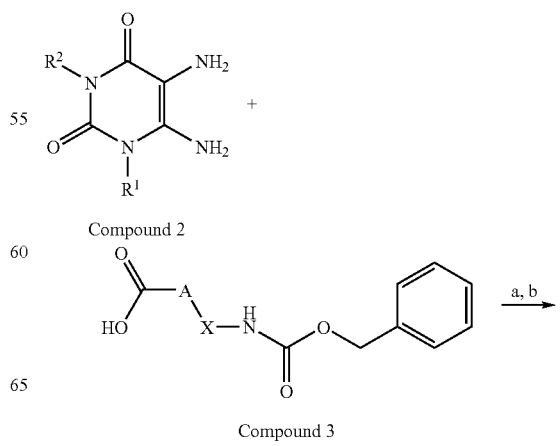

-continued

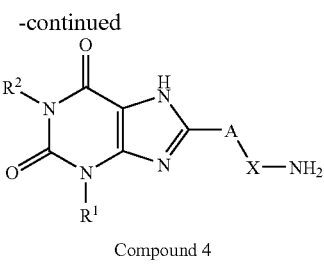

Compound 4

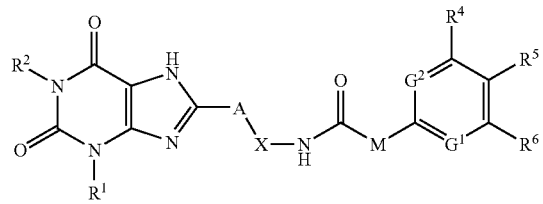

Compound 1A a) EDCI. b) NaOH. c) SOCl$_2$. d) TEA, CH$_2$Cl$_2$

After cooling the resulting clear aqueous solution to room temperature, the solution is typically acidified to approximately pH=5 using a suitable inorganic acid, such as concentrated HCl, until the intermediate 8-(aminoheteroaryl)-1,3-disubstituted-xanthine precipitates. The precipitated intermediate may then be collected by filtration or centrifugation further purifying, if desired, by recrystallization from an appropriate solvent or combination of solvents or by chromatography.

A solution of the requisite carboxylic acid (Compound 5) may then be converted to the corresponding acyl halide by suspending in the appropriate halogenating reagent, such as thionyl chloride, phosphorus oxychloride, thionyl bromide, phosphorus trichloride, or phosphorus tribromide, optionally in the presence of a suitable solvent, such as methylene chloride, chlorform, 1,2-dichloroethane, 1,4-dioxane, or diethyl ether, and warming to between 30 and 90° C. for 1 to 18 hours.

After removal of the excess halogenating reagent, a solution of the intermediate 8-(aminoheteroaryl)-1,3-disubstituted-xanthine and a suitable base, such as triethylamine, diethylisopropylamine, or diisopropylethylamine, is added to the acyl halide dissolved in an appropriate solvent. After stirring the mixture at 10 to 80° C. for 1 to 36 hours, the mixture is evaporated, and the residue partitioned between an organic solvent and a saturated aqueous solution of sodium bicarbonate. After drying the organic extract, the desired product is typically purified by column chromatography on silica gel.

Alternatively, compounds of the present invention may be prepared as depicted in Scheme 2. In this sequence, 1,3-disubstituted-5,6-diaminouracils (Compound 2) may be condensed with heteroarylcarboxylic acids possessing an ethoxycarbonylmethoxy group attached to the heteroaryl moiety. Such condensation may be effected by treating a solution of the 1,3-disubstituted-5,6-diaminouracil (Compound 2) in an appropriate volume of a lower alcohol with the desired heteroaryl carboxylic acid (Compound 6) and a suitable coupling agent, such as 3-ethyl-1-(3-dimethylaminopropy-1)-3-ethylcarbodiimide hydrochloride (EDCl) or 1,3-dicyclohexylcarbodiimid-e (DCC), at a temperature of 5 to 70° C., for a period of 1 to 24 hours.

After removing the residual solvent, the intermediate amide is treated with an excess of an aqueous basic solution, such as sodium hydroxide or potassium hydroxide at a temperature of 30 to 100° C. for 15 minutes to 12 hours to afford the desired 8-(carboxymethoxy-heteroaryl)-1,3-disubstituted-xanthine (Compound 7).

Scheme 2:

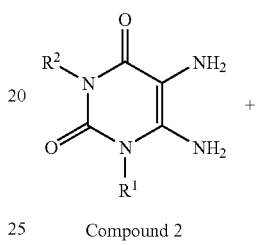

Compound 2

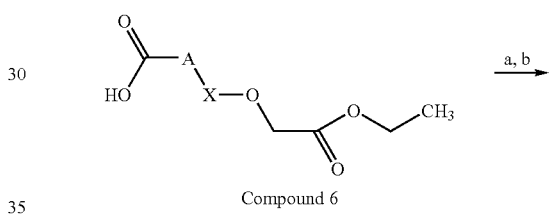

Compound 6

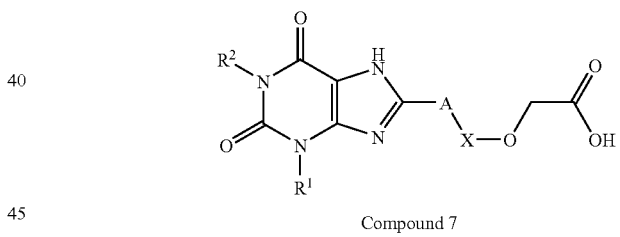

Compound 7

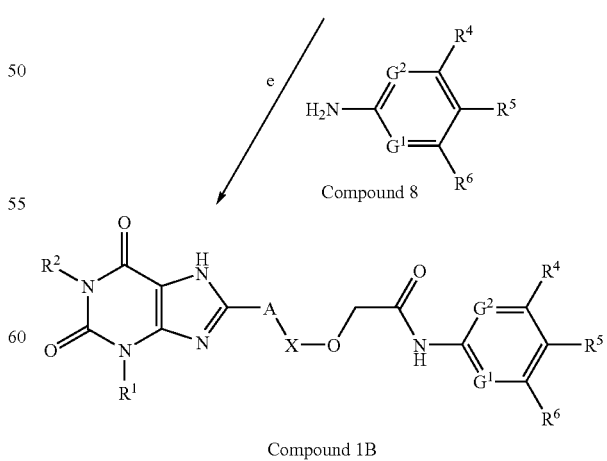

Compound 1B a) EDCI. b) NaOH. e) EDCI, HOBt, DMF

Condensation of the intermediate xanthine (Compound 7) with a suitable aniline, or heteroaromatic amine (Compound 8) affords the desired products following normal purification procedures. This condensation is typically performed in dimethylformamide, or other suitable solvent, such as dimethylacetamide, hexamethylphosphortriamide, or ethyl acetate, using EDCl and HOBt to promote the amide bond formation at temperatures of 10 to 90° C. for periods of 10 minutes to 24 hours.

It will be recognized that a variety of other condensation procedures, all well known in the art, such as the use of DCC or the conversion of the carboxylic acid to an activated ester and displacement with the amine, will also result in the preparation of the desired compounds.

In another illustrative synthesis example, Scheme 3, the intermediate Compound 4, dissolved in an appropriate solvent such as anhydrous 1,4-dioxane, methylene chloride, 1,2-dichloroethane, or 1,2-dimethoxyethane, is treated with a suitable isocyanate (Compound 9) at room temperature or above for a period of 4 to 24 hours to afford the desired 8-heteroaryl)xanthine ureas. The desired products are typically precipitated by the addition of water, followed by column chromatography purification on silica gel.

Scheme 3:

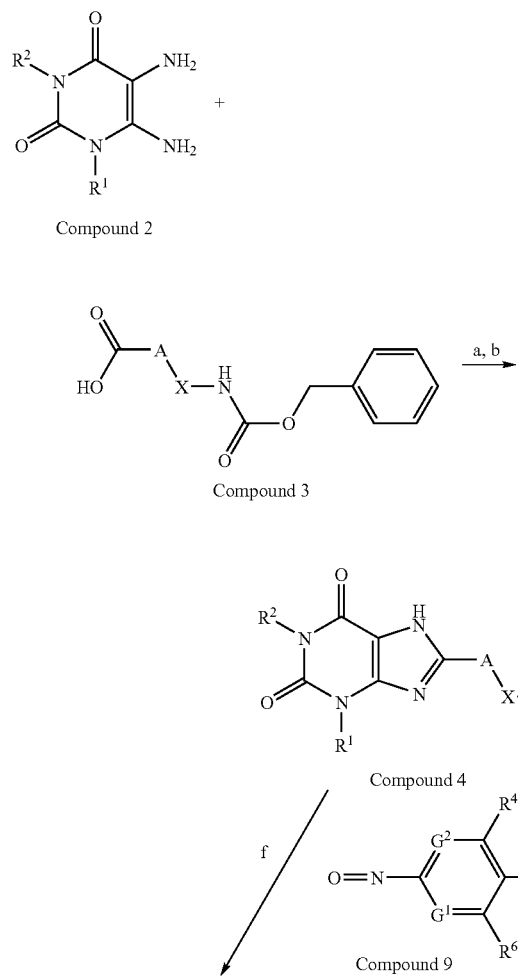

-continued

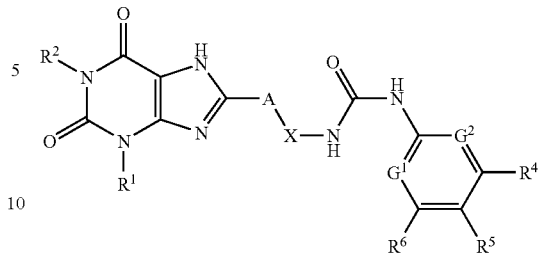

Compound 1C a) EDCl. b) NaOH. f) 1,4-dioxane 5,6-Diamino-1,3-dimethyluracil, 5,6-diamino-1,3-diallyluracil, and 5,6-diamino-1,3-diropylluracil are commercially available. The 5,6-diamino-1,3-diisobutyluracil may be prepared as previously described (M. Merlos, et al., *Eur. J. Med. Chem.* 25: 652 (1990).). The synthesis of 1-methyl-3-benzyloxy-carbonylamino-pyrazole-5-carboxylic acid and 1-methyl-5-benzyloxycarbonylamino-pyrazole-3-carboxylic acid follows the method of Lee and Cain (*J. Org. Chem.* 54: 428 (1989)).

The synthesis of ethyl (3-carboxy-1-methylpyrazol-5-yl) oxyacetate and ethyl (5-carboxy-1-methylpyrazoi-3-yl)oxyacetate has been described by Sucrow and coworkers (*Chem. Ber.* 109: 253 (1976) and *Chem. Ber.* 109: 268 (1976)). 1-Methyl-4-nitroimidazole-2-carboxylate is prepared as described by Krowicki and Lown (*J. Org. Chem.* 52: 3493 (1987)). 1-Methyl-4-nitropyrrole-2-carboxylate is commercially available. Aicher and coworkers (*J. Med. Chem.* 41: 4556 (1998)) recently described the preparation of 3-substituted-5-hydroxymethyl-isoxazoles, which are readily acylated using methods well known to those skilled in the art.

The 4-(substituted)-benzyloxyphenylacetic acids not commercially available may be prepared from methyl 4-hydroxyphenylacetate and the appropriate benzyl halides, as described by Muller, Reindl, and Breu (*J. Med. Chem.* 44: 814 (2001)) for 4-(3-methoxybenzyloxy)phenylacetic acid. All other starting materials are generally available from normal commercial sources.

The following examples are provided in a non-limiting manner to further illustrate the methods of synthesis and use of the compounds of the present invention.

EXAMPLE 1

Preparation Of Compound AS3

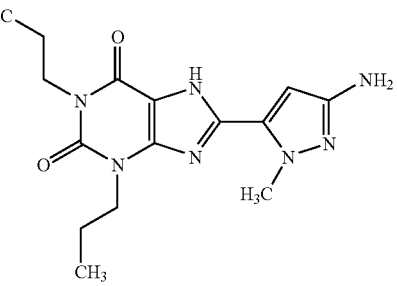

A solution of 1,3-dipropyl-5,6-diaminouracil (0.7 g, 0.003 mol), 1-methyl-3-(benzyloxycarbonylamino)-pyrazole-5-carboxylic acid (0.8 g, 0.003 mol), and EDCl (0.6 g, 0.003 mol) in 50 mL of $CH_3OH$ was stirred at room temperature for two hours. Excess $CH_3OH$ was evaporated in vacuo to give a yellow solid that was collected by filtration and washed with $H_2O$ to give the amide intermediate.

A mixture of the amide intermediate and 30 mL of 2.5 N NaOH was warmed to 70-80° C. for three hours. The clear aqueous solution was cooled and acidified to pH 5 with concentrated HCl. The white precipitate that formed was collected by filtration and washed with $H_2O$ to afford the desired 1,3-dipropyl-8-(3-amino-i-methylpyrazol-5-yl)xanthine, which was recrystallized from $CH_3OH$.

MP: 285-288° C.; $^1$H-NMR (DMSO-$d_6$): δ0.93 (m, 6H), 1.58 (m, 2H), 1.75 (m, 2H), 3.88 (bs, 2H), 4.01 (s, 5H), 6.21 (s, 1H), 13.51 (bs, 1H).

EXAMPLE 2

Preparation of Compound AS11

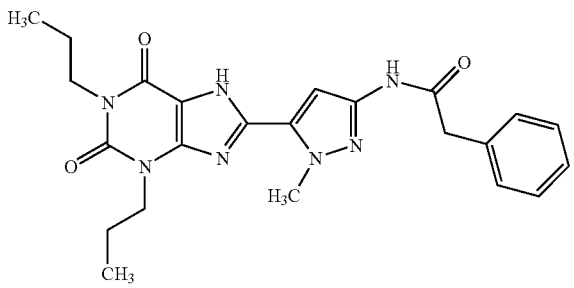

A solution of phenylacetic acid (0.196 mmol) in 3 mL of thionyl chloride was stirred at 70° C. for four hours, then excess thionyl chloride removed in a nitrogen stream. A solution of 1,3-dipropyl-8-(3-amino-1-methylpyrazol-5-yl)xanthine (0.151 mmol, Example 1) and 0.04 mL of anhydrous triethylamine in 10 mL of $CH_2Cl_2$: $CH_3OH$ (1:1) was added and the mixture was stirred at room temperature for 24 hours, monitoring by TLC.

At completion, the solvent was evaporated, the residue dissolved in ethyl acetate, and the solution washed with saturated aqueous $NaHCO_3$ and brine. The organic layer was dried ($Na_2SO_4$), filtered, and evaporated in vacuo. The desired product was purified by column chromatography on silica gel.

MP: 139-140° C.; $^1$H-NMR (DMSO-$d_6$): δ 0.89 (q, 6H, J=5.18 Hz), 1.59 (q, 2H), J=7.18 Hz), 1.72 (q, 2H, J=7.06 Hz), 3.62 (s, 2H), 3.88 (t, 2H, J=6.72 Hz), 3.98 (t, 2H), J=6.96 Hz), 4.12 (s, 3H), 7.25-7.33 (m, 6H), 10.8 (s, 1H), 14.02 (s, 1H).

EXAMPLE 3

Preparation of Compound AS12

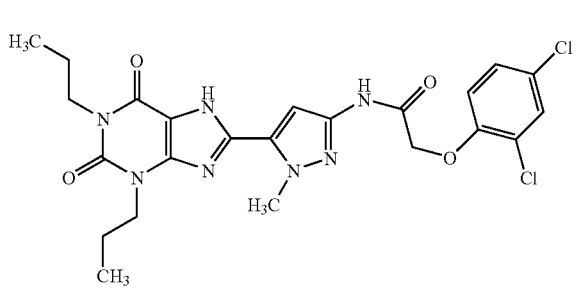

Using 2,4-dichlorophenoxyacetic acid and 1,3-dipropyl-8-(3-amino-1-methylpyrazol-5-yl)xanthine (Example 1, Compound AS3).

MP: 225-226° C.; $^1$H-NMR (DMSO-$d_6$): δ 0.85 (m, 6H), 1.59 (m, 2H), 1.72 (m, 2H), 3.85 (t, 2H), 4.01 (t, 2H), 4.14 (s, 3H), 4.87 (s, 2H), 7.10 (d, 1H), 7.33 (m, 2H), 7.60 (d, 1H), 10.80 (s, 1H), 14.02 (s, 1H).

EXAMPLE 4

Preparation of Compound AS13

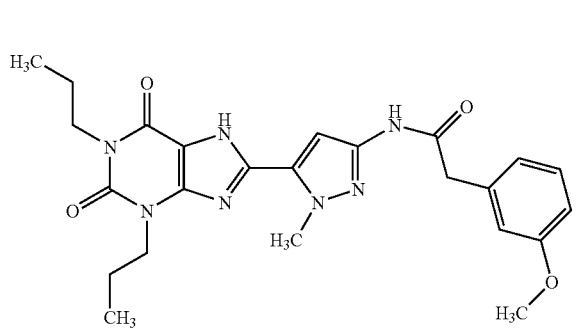

Using 3-methoxyphenylacetic acid and 1,3-dipropyl-8-(3-amino-1-methylpyrazol-5-yl)xanthine (Example 1, Compound AS3).

MP: 158-159° C.; $^1$H-NMR (DMSO-$d_6$): δ 0.89 (q, 6H, J=7.13 Hz), 1.62 (q, 2H), 1.72 (q, 2H), 3.59 (s, 2H), 3.74 (s, 3H), 3.85 (t, 2H), 4.00 (t, 2H), 4.13 (s, 3H), 6.92 (s, 1H), 7.30 (m, 4H), 10.77 (s, 1H), 14.00 (s, 1H).

EXAMPLE 5

Preparation of Compound AS14

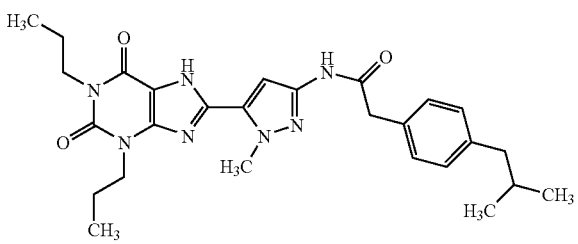

Using 4-(2-methylpropyl)phenylacetic acid and 1,3-dipropyl-8-(3-amino-1-methylpyrazol-5-yl)xanthine (Example 1, Compound AS3).

MP: 124-126° C.; .¹H-NMR (DMSO-d₆): δ 0.85 (m, 12H, J=6.52 Hz), 1.39 (d, 2H, J=6.87 Hz), 1.75 (m, 5H), 2.41 (d, 2H, J=7.1 Hz), 3.85 (t, 2H, J=6.94 Hz), 4.00 (t, 2H), 4.10 (s, 3H), 7.11 (d, 1H), 7.30 (m, 4H, J=8.05 Hz), 10.70 (s, 1H), 13.99 (s, 1H).

EXAMPLE 6

Preparation of Compound AS15

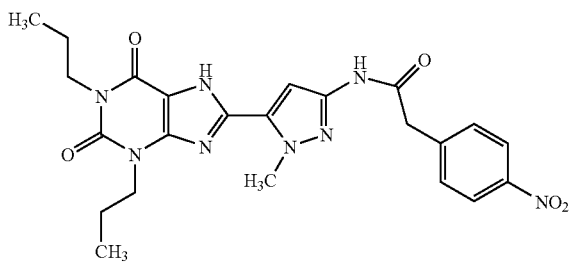

Using 4-nitrophenylacetic acid and 1,3-dipropyl-8-(3-amino-1-methylpyrazol-5-yl)xanthine (Example 1, Compound AS3).

MP: 285-287° C.; .¹H-NMR (DMSO-d₆): δ 0.89 (m, 6H, J=6.83 Hz), 1.55 (q, 2H, J=6.83 Hz), 1.72 (q, 2H, J=7.05 Hz), 3.89 (d, 4H), 4.00 (t, 2H), 4.13 (s, 3H), 7.27 (s, 1H), 7:63 (d, 2H, J=8.47 Hz), 8.18 (d, 2H, J=8.34 Hz), 10.87 (s, 1H), 13.90 (s, 1H).

EXAMPLE 7

Preparation of Compound AS16

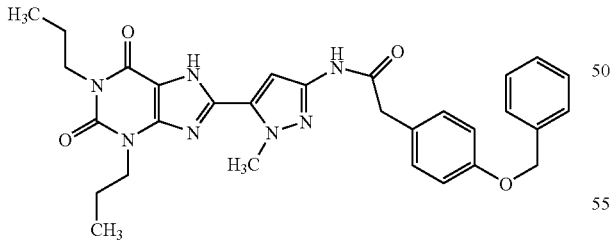

Using 4-(benzyloxy)phenylacetic acid and 1,3-dipropyl-8-(3-amino-1-methylpyrazol-5-yl)xanthine (Example 1, Compound AS3).

MP: 184-185° C.; .¹H-NMR (DMSO-d₆): δ 0.89 (m, 6H), 1.59 (q, 2H, J=6.98 Hz), 1.69 (q, 2H, J=7.1 Hz), 3.54 (s, 2H), 3.85 (t, 2H), 3.98 (t, 2H), 4.13 (s, 3H), 5.00 (s, 2H), 6.98 (d, 1H), 7.28 (m, 9H, J=6.46 Hz), 10.75 (s,1H), 14.02 (s, 1H).

EXAMPLE 8

Preparation of Compound AS17

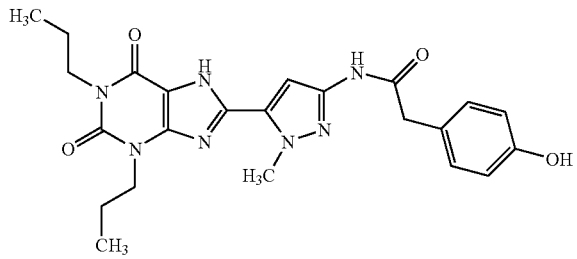

Using 4-hydroxyphenylacetic acid and 1,3-dipropyl-8-(3-amino-1-methylpyrazol-5-yl)xanthine (Example 1, Compound AS 3).

MP: 145-150° C.; .¹H-NMR (DMSO-d₆): δ 0.86 (m, 6H), 1.55 (m, 2H), 1.72 (m, 2H), 3.40 (s, 2H), 3.85 (t, 2H), 3.98 (t, 2H), 4.10 (s, 3H), 6.69 (d, 2H, J=8), 7.31 (s, 1H), 9.20 (s,1H), 10.70 (s, 1H), 14.0 (s, 1H1).

EXAMPLE 9

Preparation of Compound AS18

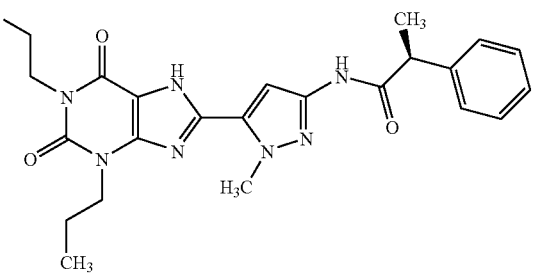

Using (S)-2-phenylpropanoic acid and 1,3-dipropyl-8-(3-amino-1-methylpyrazol-5-yl)xanthine (Example 1, Compound AS3).

MP: 125-126° C.; .¹H-NMR (CDCl₃): δ 0.85 (m, 6H), 1.57 (s,3H), 1.59 (m, 2H), 1.61 (m, 2H), 1.70 (m, 1H), 4.1 (m, 4H), 4.16 (s, 3H), 7.37 (m, 5H), 7.39 (s, 1H), 7.90, (s, 1H), 12.8(s, 1H).

EXAMPLE 10

Preparation of Compound AS19

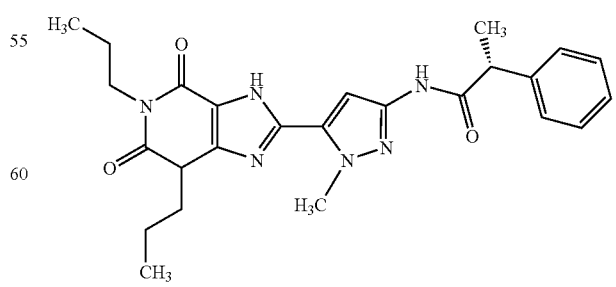

Using (R)-2-phenylpropanoic acid and 1,3-dipropyl-8-(3-amino-1-methylpyrazol-5-yl)xanthine (Example 1, Compound AS3).

MP: 125-126° C.; 1H-NMR (CDCl₃): δ 0.85 (m, 6H), 1.57 (s, 3H), 1.59 (m, 2H), 1.61 (m, 2H), 1.70 (m, 1H), 4.1 (m, 4H), 4.16 (s, 3H), 7.37 (m, 5H), 7.39 (s, 1H), 7.90 (s, 1H), 12.8 (s, 1H).

EXAMPLE 11

Preparation of Compound AS21

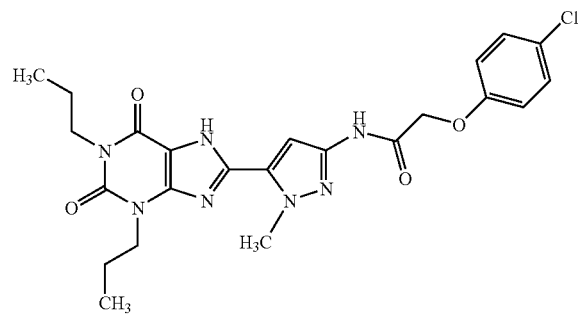

Using 4-chlorophenoxyacetic acid and 1,3-dipropyl-8-(3-amino-1-methylpyrazol-5-yl)xanthine (Example 1, Compound AS3).

MP: 260-261° C.; ¹H-NMR (DMSO-d₆): δ 0.85 (m, 6H), 1.59 (m, 2H), 1.72 (m, 2H), 3.85 (t, 2H), 3.98 (t, 2H), 4.14 (s, 3H), 6.98 (d, 2H, J=8.0 Hz), 7.36 (d, 2H, J=8.0 Hz), 7.33 (s, 1H), 10.80 (s, 1H), 14.02 (s, 1H).

EXAMPLE 12

Preparation of Compound AS22

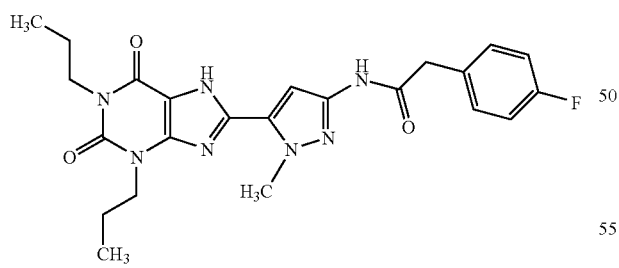

Using 4-fluorophenylacetic acid and 1,3-dipropyl-8-(3-amino-1-methylpyrazol-5-yl)xanthine (Example 1, Compound AS3).

MP: 176° C.; ¹H-NMR (DMSO-d₆). δ 0.88 (m, 6H), 1.60 (m, 2H), 1.70 (m, 2H), 3.60 (s, 2H), 3.70 (s, 3H), 3.80 (t, 2H), 4.00 (t, 2H), 4.10 (s, 3H), 7.15 (m, 2H), 7.31 (m, 2H), 7.30 (s, 1H), 10.70 (s, 1H), 14.0 (s, 1H).

EXAMPLE 13

Preparation of Compound AS23

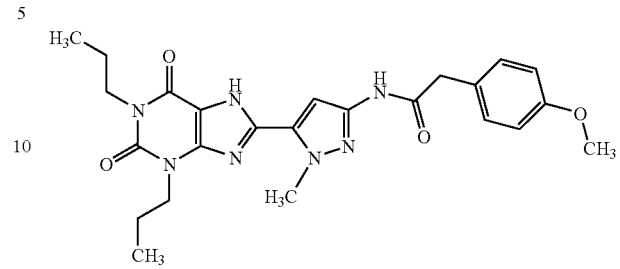

Using 4-methoxyphenylacetic acid and 1,3-dipropyl-8-(3-amino-1-methylpyrazol-5-yl)xanthine (Example 1, Compound AS3).

MP: 125-126° C.; .¹H-NMR (DMSO-d₆): δ 0.86 (m, 6H), 1.50 (m, 2H), 1.70 (m, 2H), 3.50 (s, 2H), 3.70 (s, 3H), 3.80 (t, 2H), 4.00 (t, 2H), 4.10 (s, 3H), 7.15 (m, 2H), 7.31 (m, 2H), 7.30 (s, 1H), 10.70 (s, 1H), 14.0 (s, 1H).

EXAMPLE 14

Preparation of Compound AS24

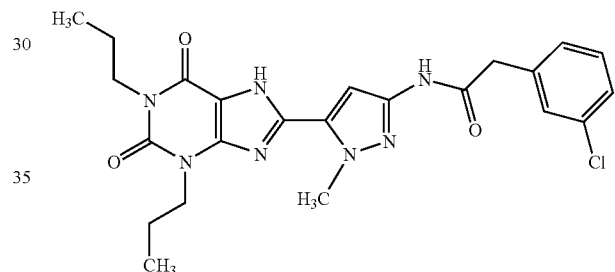

Using 3-chlorophenylacetic acid and 1,3-dipropyl-8-(3-amino-i1-methypyrazol-5-yl)xanthine (Example 1, Compound AS3).

MP: 143-145° C.; ¹H-NMR (DMSO-d₆): δ 0.86 (m, 6H), 1.50 (m, 2H), 1.70 (m, 2H), 3.60 (s, 2H), 3.80 (t, 2H), 4.00 (t, 2H), 4.10 (s, 3H), 7.30 (m, 4H), (s, 1H), 10.8 (s, 1H), 14.0 (s, 1H).

EXAMPLE 15

Preparation of Compound AS25

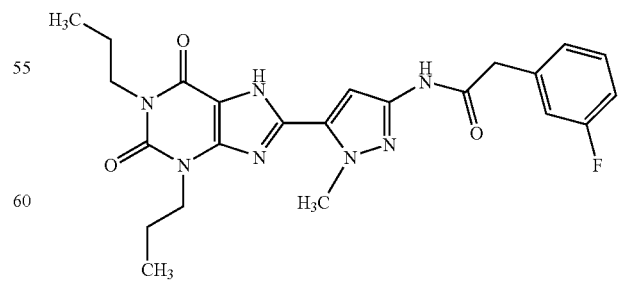

Using 3-fluorophenylacetic acid and 1,3-dipropyl-8-(3-amino-1-methylpyrazol-5-yl)xanthine (Example 1, Compound AS3).

MP: 148-150° C.; ¹H-NMR (DMSO-$d_6$): δ 0.86 (m, 6H), 1.50 (m, 2H), 1.70 (m, 2H), 3.60 (s, 2H), 3.80 (t, 2H), 4.00 (t, 2H), 4.10 (s, 3H), 7.10 (m, 4H), 7.30 (s, 1H), 10.8 (s, 1H), 14.0 (s, 1H).

EXAMPLE 16

Preparation of Compound AS26

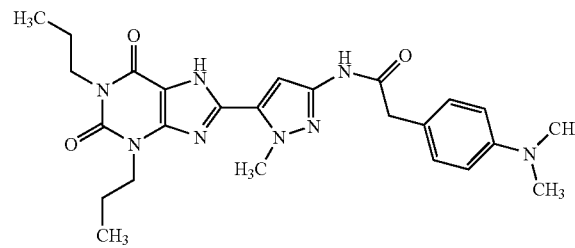

Using 4-(dimethylamino)phenylacetic acid and 1,3-dipropyl-8-(3-amino-1-methylpyrazol-5-yl)xanthine (Example 1, Compound AS3).

MP: 215° C.; ¹H-NMR (DMSO-$d_6$): δ 0.86 (m, 6H), 1.50 (m, 2H), 1.70 (m, 2H), 2.80 (s, 6H), 3.60 (s, 2H), 3.80 (t, 2H)?, 4.00 (t, 2H), 4.10 (s, 3H), 6.67 (d, 2H, J=8.0 Hz), 7.14 (d, 2H, J=8.0 Hz), 7.29 (s, 1H), 10.8 (s, 1H), 14.0 (s, 1H).

EXAMPLE 17

Preparation of Compound AS27

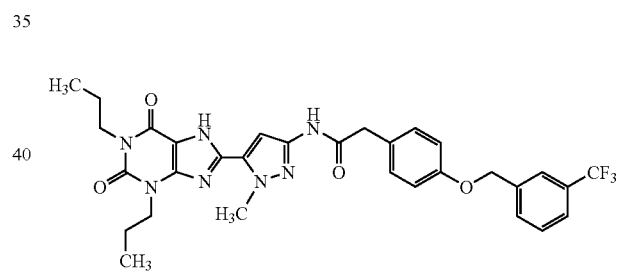

Using 4-chlorophenylacetic acid and 1,3-dipropyl-8-(3-amino-1-methylpyrazol-5-yl)xanthine (Example 1, Compound AS3).

MP: 159-161° C.; ¹H-NMR (DMSO-$d_6$): δ 0.86 (m, 6H), 1.50 (m, 2H), 1.70 (m, 2H), 3.60 (s, 2H), 3.80 (t, 2H), 4.00 (t, 2H), 4.10 (s, 3H), 7.29 (s, 1H), 7.32 (d, 2H, J=8.0 Hz), 7.38 (d, 2H, J=8.0 Hz), 10.8 (s, 1H), 14.0 (s, 1H).

EXAMPLE 18

Preparation of Compound AS28

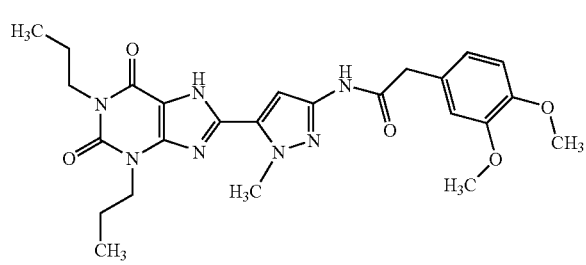

Using 3,4-(dimethoxy)phenylacetic acid and 1,3-dipropyl-8-(3-amino-1-methylpyrazol-5-yl)xanthine (Example 1, Compound AS3).

MP: 140-142° C.; ¹H-NMR (DMSO-$d_6$): δ 0.87 (m, 6H), 1.55 (q, 2H), 1.72 (q, 2H), 3.50 (s, 2H), 3.74 (s, 6H), 3.82 (t, 2H), 4.02 (t, 2H), 4.13 (s, 3H), 6.88 (m, 3H, J=3.58), 6.96 (d, 1H), 7.33 (s, 1H), 10.73 (s, 1H).

EXAMPLE 19

Preparation of Compound AS29

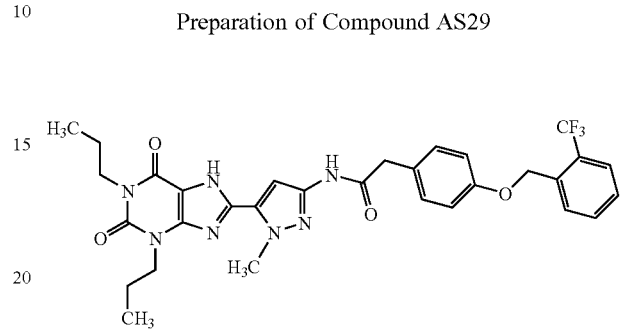

Using 4-(2-trifluoromethylbenzyloxy)phenylacetic acid and 1,3-dipropyl-8-(3-amino-1-methylpyrazol-5-yl)xanthine (Example 1, Compound AS3).

MP: 184-186° C.; ¹H-NMR (DMSO-$d_6$): δ 0.88 (m, 6H), 1.59 (q, 2H), 1.69 (q, 2H), 3.54 (s, 2H), 3.85 (t, 2H), 4.00 (t, 2H), 4.12 (s, 3H), 5.20 (s, 2H), 6.92 (d, 1H), 7.28 (m, 3H, J=5.48), 7.73 (m, 4H, J=6.55), 10.75 (s, 1H), 14.02 (s, 1H).

EXAMPLE 20

Preparation of Compound AS30

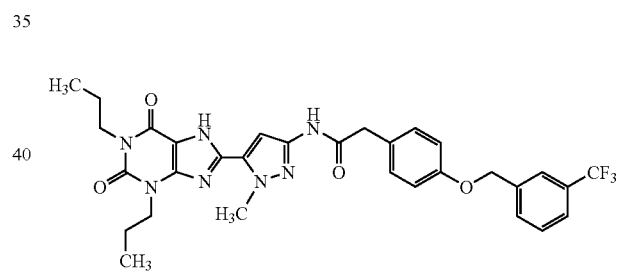

Using 4-(3-trifluoromethylbenzyloxy)phenylacetic acid and 1,3-dipropyl-8-(3-amino-1-methylpyrazol-5-yl)xanthine (Example 1, Compound AS3).

MP: 218-220° C.; ¹H-NMR (DMSO-$d_6$): δ 0.88 (m, 6H, J=5.06), 1.55 (q, 2H, J=6.88), 1.72 (q, 2H, J=7.47), 3.55 (s, 2H), 4.01 (t, 2H), 4.08 (t, 2H), 4.12 (s, 3H), 5.20 (s, 2H), 5.76 (s, 1H), 7.00 (d, 1H), 7.68 (t, 3H), 7.80 (m, 4H), 10.75 (s, 1H), 14.01 (s, 1H).

EXAMPLE 21

Preparation of Compound AS31

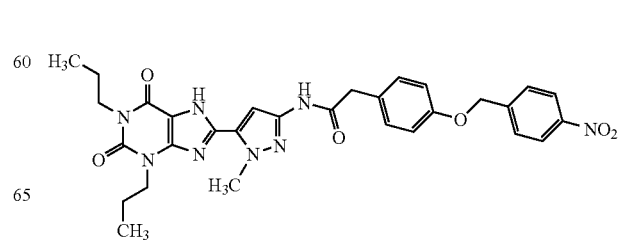

Using 4-(4-nitrobenzyloxy)phenylacetic acid and 1,3-dipropyl-8-(3-amino-1-methylpyrazol-5-yl)xanthine (Example 1, Compound AS3).

MP: 136-139° C.; .¹H-NMR (DMSO-d$_6$): δ 0.88 (m, 6H), 1.55 (q, 2H), 1.72 (q, 2H), 3.55 (s, 2H), 4.01 (t, 2H), 4.08 (t, 2H), 4.12 (s, 3H), 5.20 (s, 2H), 7.00 (d, 1H), 7.48 (t, 4H), 7.80 (d, 2H), 8.30 (d, 2H), 10.75 (s, 1H).

EXAMPLE 22

Preparation of Compound AS32

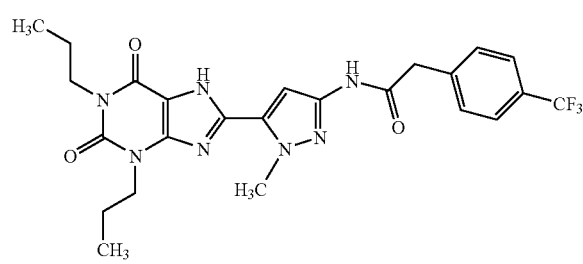

Using 4-(trifluoromethyl)phenylacetic acid and 1,3-dipropyl-8-(3-amino-1-methylpyrazol-5-yl)xanthine (Example 1, Compound AS3).

MP: 240° C.; .¹H-NMR (DMSO-d$_6$): δ 0.88 (m, 6H), 1.55 (q, 2H), 1.72 (q, 2H), 3.75 (s, 2H), 3.89 (t, 2H), 4.01 (t, 2H), 4.08 (s, 3H), 7.27 (s, 1H), 7.68 (d, 2H), 7.80 (d, 2H), 10.85 (s, 1H).

EXAMPLE 23

Preparation of Compound AS43

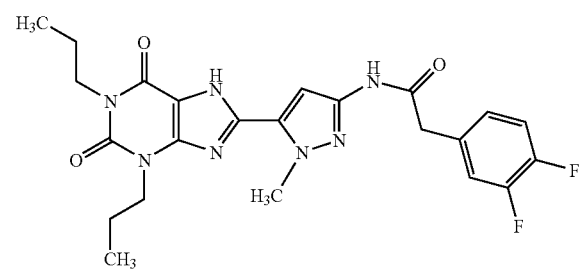

Using 3,4-difluorophenylacetic acid and 1,3-dipropyl-8-(3-amino-1-methylpyrazol-5-yl)xanthine (Example 1, Compound AS3).

MP: 250-252° C.;. ¹H-NMR (DMSO-d$_6$): δ 0.86 (m, 6H), 1.50 (m, 2H), 1.70 (m, 2H), 3.60 (s, 2H), 3.80 (t, 2H), 4.00 (t, 2H), 4.10 (s, 3H), 7.29 (s, 1H), 7.32 (m, 3H), 10.80 (s, 1H), 14.00 (s, 1H).

EXAMPLE 24

Preparation of Compound AS44

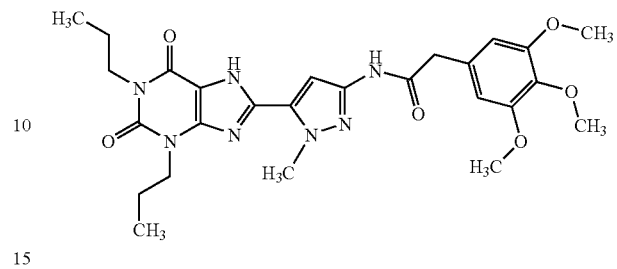

Using 3,4,5-(trimethoxy)phenylacetic acid and 1,3-dipropyl-8-(3-amino-1-methylpyrazol-5-yl)xanthine (Example 1, Compound AS3).

MP: 298-300° C.; ¹H-NMR (DMSO-d$_6$): δ 0.88 (m, 6H), 1.55 (q, 2H), 1.72 (q, 2H), 3.54 (s, 2H), 3.62 (s, 3H), 3.75 (s, 6H), 3.85 (t, 2H), 4.01 (t, 2H), 4.13 (s, 3H), 6.66 (s, 2H), 7.33 (s, 1H), 10.74 (s, 1H), 14.01 (s, 1H).

EXAMPLE 25

Preparation of Compound AS56

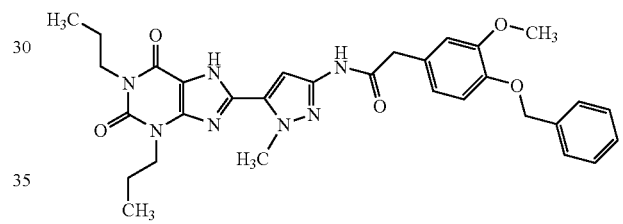

Using 4-(benzyloxy)-3-methoxyphenylacetic acid and 1,3-dipropyl-8-(3-amino-1-methylpyrazol-5-yl)xanthine (Example 1, Compound AS3).

MP: 205-208° C.; ¹H-NMR (DMSO-d$_6$): δ 0.89 (m, 6H), 1.55 (m, 2H), 1.72 (m, 2H), 3.54 (s, 2H), 3.76 (s, 3H), 3.85 (t, 2H), 4.01 (t, 2H), 4.13 (s, 3H), 5.04 (s, 2H), 6.84 (d, 1H), 6.98 (d, 2H), 7.38 (m, 6H, J=8.36), 10.72 (s, 1H).

EXAMPLE 26

Preparation of Compound AS57

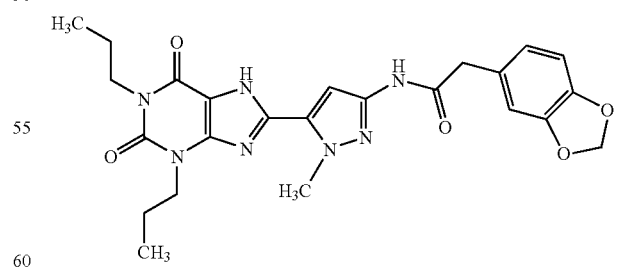

Using 3,4-methylenedioxyphenylacetic acid and 1,3-dipropyl-8-(3-amino-1-methylpyrazol-5-yl)xanthine (Example 1, Compound AS3).

MP: 138-140° C.; ¹H-NMR (DMSO-d$_6$): δ 0.88 (m, 6H), 1.58 (m, 2H), 1.71 (m, 2H), 3.52 (s, 2H), 3.85 (t, 2H), 4.00 (t, 2H), 4.12 (s, 3H), 5.97 (s, 2H), 6.83 (m, 3H), 7.27 (s, 1H), 10.71 (s, 1H), 14.00 (s, 1H).

EXAMPLE 27

Preparation of Compound AS58

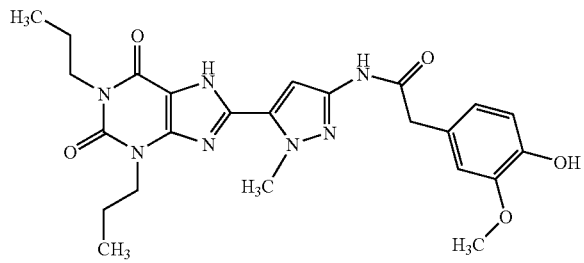

Using 4-hydroxy-3-methoxyphenylacetic acid and 1,3-dipropyl-8-(3-amino-1-methylpyrazol-5-yl)xanthine (Example 1, Compound AS3).

MP: 185° °C.; $^1$H-NMR (DMSO-$d_6$): δ 0.88 (m, 6H), 1.58 (m, 2H), 1.71 (m, 2H), 3.40 (s, 2H), 3.81 (s, 3H), 3.83 (t, 2H), 3.88 (t, 2H), 4.12 (s, 3H), 6.70 (s, 1H), 6.90 (s, 1H), 7.30 (s, 1H), 8.80 (s, 1H), 10.71 (s, 1H), 14.00 (s, 1H).

EXAMPLE 28

Preparation of Compound AS8

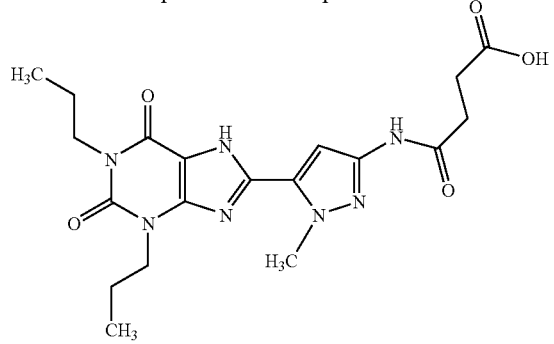

A solution of succinic anhydride and 1,3-dipropyl-8-(3-amino-1-methylpyrazol-5-yl)xanthine (Example 1, Compound AS3) in 1,4-dioxane was heated at 60° C. overnight, the solvent removed, and the residue purified by column chromatography on silica gel to provide the desired product.

MP: 265-266° C.; $^1$H-NMR (DMSO-$d_6$): δ 0.86 (m, 6H), 1.55 (m, 2H), 1.72 (m, 2H), 3.31 (s, 2H), 3.34 (s, 2H), 3.65 (t, 2H), 3.98 (t, 2H), 4.01 (s, 3H), 7.33 (s, 1H), 10.50 (s, 1H), 12.10 (s, 1H), 14.01 (s, 1H).

EXAMPLE 29

Preparation of Compound AS9

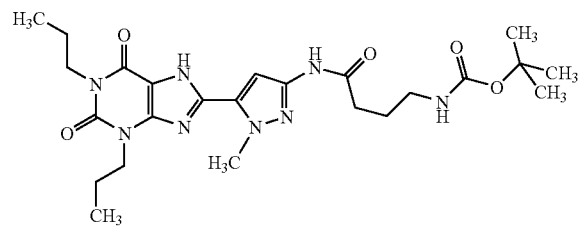

Using 4-(t-butyloxycarbonylamino)butanoic acid and 1,3-dipropyl-8-(3-amino-1-methylpyrazol-5-yl)xanthine (Example 1, Compound AS3).

MP: 215-216° C.; $^1$H-NMR (DMSO-$d_6$): δ 0.89 (m, 6H), 1.37 (s, 9H), 1.66 (m, 6H), 2.28 (m, 2H), 2.91 (m, 2H), 3.86 (t, 2H), 4.01 (t, 2H), 4.12 (s, 3H), 7.30 (s, 1H), 10.50 (s, 1H), 14.01 (s, 1H).

EXAMPLE 30

Preparation of Compound AS10

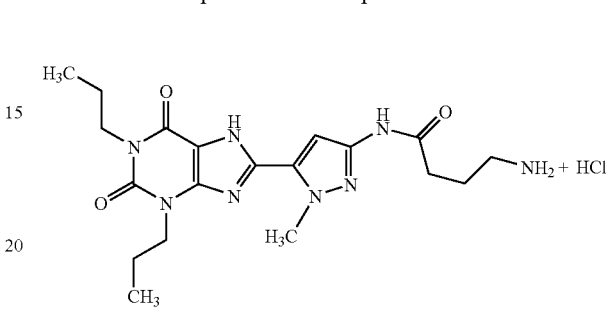

A solution of 1,3-dipropyl-8-(3-(4-(t-butyloxycarbonylamino)-1-oxo-butylamino)-1-methyl-pyrazol-5-yl)xanthine (Example 29) in 1,4-dioxane was treated with excess ethereal HCl (2 N) at room temperature for 16 hours, during which a white solid precipitated. This was collected by filtration, washing with diethyl ether to afford the desired product as the hydrochloride salt.

MP: 251-252° C.; $^1$H-NMR (DMSO-$d_6$): δ 0.89 (m, 6H), 1.59 (m, 2H), 1.72 (m, 4H), 2.45 (m, 2H), 2.81 (t, 2H), 3.86 (t, 2H), 3.98 (t, 2H), 4.12 (s, 3H), 7.30 (s, 1H), 7.95 (s, 3H), 10.62 (s, 1H), 14.02 (s, 1H).

EXAMPLE 31

Preparation of Compound AS38

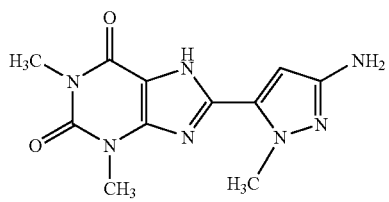

A solution of 1,3-dimethyl-5,6-diaminouracil (0.7 g, 0.003 mol), 1-methyl-3-(benzyloxycarbonylamino)-pyrazole-5-carboxylic acid (0.8 g, 0.003 mol), and EDCl (0.6 g, 0.003 mol) in 50 mL of $CH_3OH$ was stirred at room temperature for two hours. Excess $CH_3OH$ was evaporated in vacuo to give a yellow solid that was collected by filtration and washed with $H_2O$ to give the amide intermediate.

A mixture of the amide intermediate and 30 mL of 2.5 N NaOH was warmed to 70-80° C. for three hours. The clear aqueous solution was cooled and acidified to pH 5 with concentrated HCl. The white precipitate that formed was collected by filtration and washed with $H_2O$ to afford the desired 1,3-dimethyl-8-(3-amino-1-methylpyrazol-5-yl)xanthine, which was recrystallized from $CH_3OH$.

MP: >300° C.; $^1$H-NMR (DMSO-$d_6$): δ 3.20 (s, 3H), 3.40 (s, 3H), 4.00 (s, 3H), 5.50 (s, 2H), 6.20 (s, 1H), 13.20 (s, 1H).

EXAMPLE 32

Preparation of Compound AS40

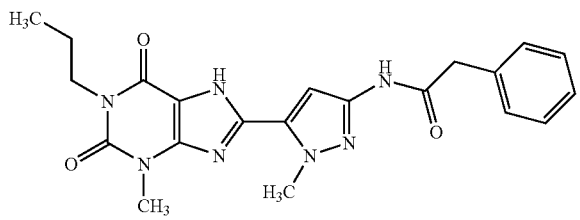

Using phenylacetic acid and 1,3-dimethyl-8-(3-amino-1-methylpyrazol-5-yl)xanthine (Example 31).

MP: >300° C.; $^1$H-NMR (DMSO-$d_6$): δ 3.20 (s, 3H), 3.40 (s, 3H), 3.60 (s, 2H), 4.10 (s, 3H), 7.30 (s, 1H), 7.40 (m, 5H), 10.80 (s, 1H), 14.00 (s, 1H).

EXAMPLE 33

Preparation of Compound AS7

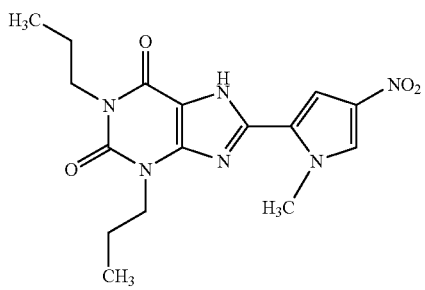

A solution of 1,3-dipropyl-5,6-diaminouracil (0.7 g, 0.003 mol), 1-methyl-4-nitropyrrole-2-carboxylic acid (0.8 g, 0.003 mol), and EDCl (0.6 g, 0.003 mol) in 50 mL of CH$_3$OH was stirred at room temperature for two hours. Excess CH$_3$OH was evaporated in vacuo to give a yellow solid that was collected by filtration and washed with H$_2$O to give the amide intermediate.

A mixture of the amide intermediate and 30 mL of 2.5 N NaOH was warmed to 70-80° C. for three hours. The clear aqueous solution was cooled and acidified to pH 5 with concentrated HCl. The white precipitate that formed was collected by filtration and washed with H$_2$O to afford the desired 1,3-dipropyl-8-(1-methyl-4-nitropyrrol-2-yl)xanthine, which was recrystallized from CH$_3$OH.

MP: 295-297° C.; $^1$H-NMR (DMSO-$d_6$): δ 0.86 (m, 6H), 1.55 (m, 2H), 1.72 (m, 2H), 3.88 (t, 2H), 3.98 (t, 2H), 3.99 (s, 3H), 7.52 (s, 1H), 8.20 (s, 1H), 14.00 (s, 1H).

EXAMPLE 34

Preparation of Compound AS36

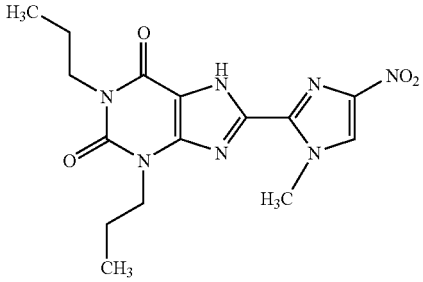

Using 1,3-dipropyl-5,6-diaminouracil and 1-methyl-4-nitroimidazole-2-carboxylic acid.

EXAMPLE 35

Preparation of Compound AS33

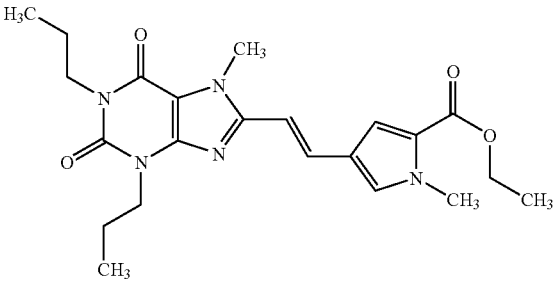

Using 1,3-dipropyl-5,6-diaminouracil and 3-(2-ethoxycarbonyl-1-methylpyrrol-4-yl)acrylic acid.

MP: 210-211° C.; $^1$H-NMR (DMSO-$d_6$): δ 0.85 (m, 6H), 1.30 (t, 3H), 1.59 (m, 2H), 1.72 (m, 2H), 3.85 (s, 3 H), 4.03 (s, 3 H), 4.10 (q, 2H), 7.10 (d, 2H), 7.59 (d, 2H), 7.60 (s, 1H).

EXAMPLE 36

Preparation of Compound AS59

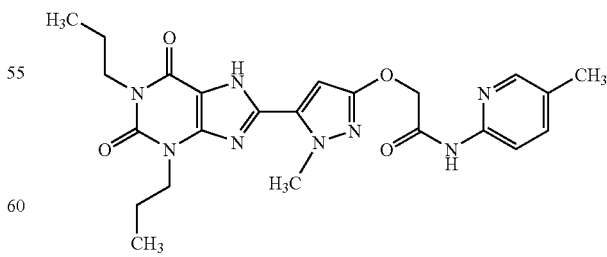

To a solution of ethyl (5-carboxy-1-methypyrazol-3-yl) oxyacetate (0.5 mmol) and EDCI (0.5 mmol) in methanol (20 mL) was added a solution of 1,3-dipropyl-5,6-diaminouracil (0.5 mmol), dissolved in methanol (20 mL). The mixture was stirred at room temperature for two hours, the solvent was then removed in vacuo, water added, and the solid that formed was collected by filtration and washed with additional cold water. The intermediate amide was heated in 20 mL of 2.5 N NaOH at 70° C. for 30 minutes to afford the desired 2-[5-(1,3-dipropyl-xanthin-8-yl)-1-methylpyrazol-3-vloxy]acetic acid.

Condensation of 2-[5-(1,3-dipropyl-xanthin-8-yl)-1-methylpyrazol-3-yloxy]acetic acid (0.5 mmol) and 5-methyl-2-aminopyridine (1.3 mmol) in the presence of EDCI (1.12 mmol) and HOBt (1.14 mmol) in anhydrous dimethylformamide afforded the desired product.

MP: 278-280° C.; $^1$H-NMR (DMSO-$d_6$): δ 0.90 (m, 6H, J=4.66 Hz), 1.55 (m, 2H, J=7.38 Hz), 1.67 (m, 2H, J=7.34 Hz), 2.24 (s, 3H), 3.89 (t, 2H, J=7.34 Hz), 4.00 (t, 2H, J=7.14 Hz), 4.05 (s, 3H), 4.82 (s, 2H), 6.44 (s, 1H), 7.64 (dd, 1H), 7.93 (d, 1H), 8.15 (d, 1H), 10.43 (s, 1H), 13.95 (bs, 1H).

EXAMPLE 37

Preparation of Compound AS64

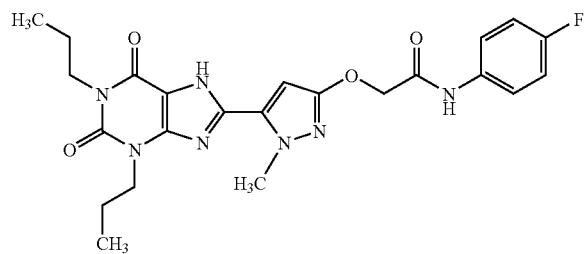

Using 4-fluoroaniline and 2-[5-(1,3-dipropyl-xanthin-8-yl)-1-methylpyrazol-3-vloxy]acetic acid (Example 36).

MP: 264° C.; 1H-NMR (DMSO-$d_6$): δ 0.87 (m, 6H), 1.55 (q, 2H), 1.59 (q, 2H), 3.86 (t, 2H), 4.00 (t, 2H), 4.07 (s, 3H), 4.76 (s, 2H), 6.50 (s, 1H), 7.16 (m, 2H, J=8.75 Hz), 7.64 (m, 2H, J=5.04), 10.20 (s, 1H).

EXAMPLE 38

Preparation of Compound AS65

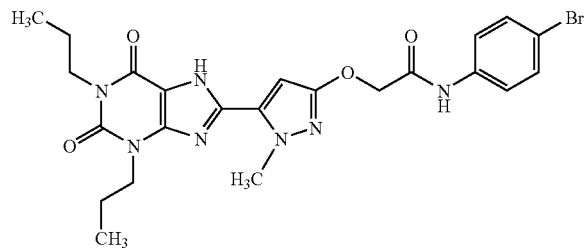

Using 4-bromoaniline and 2-[5-(1,3-dipropyl-xanthin-8-yl)-1-methylpyrazol-3-vloxy]acetic acid (Example 36).

MP: 264° C.; $^1$H-NMR (DMSO-$d_6$): δ 0.90 (m, 6H), 1.59 (m, 2H), 1.71 (m, 2H), 3.86 (t, 2H), 4.00 (t, 2H), 4.06 (s, 3H), 4.77 (s, 2H), 6.50 (s, 1H), 7.52 (m, 4H), 10.26 (s, 1H).

EXAMPLE 39

Preparation of Compound AS68

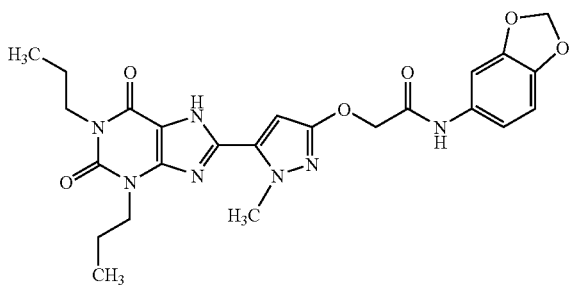

Using 3,4-methylenedioxyaniline and 2-[5-(13-dipropyl-xanthin-8-yl)-1-methylpyrazol-3-yloxy]acetic acid (Example 36).

MP: 272-273° C.; $^1$H-NMR (DMSO-$d_6$): δ 0.89 (m, 6H), 1.60 (m, 2H), 1.70 (m, 2H), 3.90 (t, 2H), 3.98 (t, 2H), 4.07 (s, 3H), 4.73 (s, 2H), 5.98 (s, 2H), 6.52 (s, 1H), 6.88 (d, 1H, J=8.44 Hz), 7.01 (d, 1H), 7.32 (s, 1H), 10.01 (s, 1H).

EXAMPLE 40

Preparation of Compound AS69

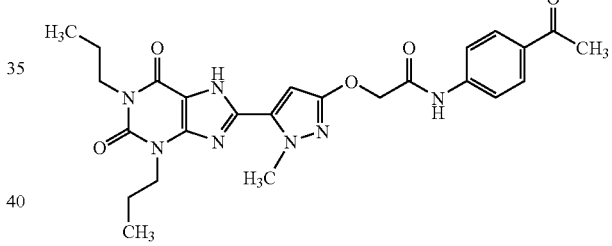

Using 4-acetylaniline and 2-[5-(1,3-dipropyl-xanthin-8-yl)-1-methylpyrazol-3-yloxy]acetic acid (Example 36).

MP: 273-275° C.; $^1$H-NMR (DMSO-$d_6$): δ 0.90 (m, 61H, J=7.34Hz), 1.74 (m, 4H, J=6.97 Hz), 2.60 (s, 3H), 4.00 (bt, 2H), 4.14 (t, 2H), 4.19 (s, 3H), 4.86 (s, 2H), 6.60 (s, 1H), 7.85 (d, 2H, J=8.58 Hz), 7.96 (d, 2H, J=8.69Hz), 8.82 (s, 1H), 12.95 (bs, 1H).

EXAMPLE 41

Preparation of Compound AS66

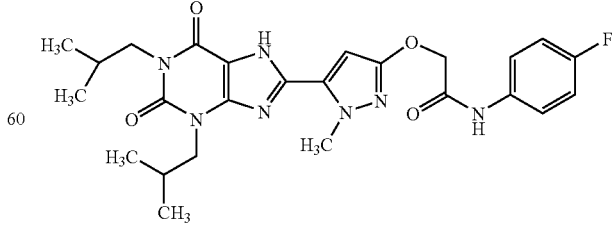

To a solution of ethyl (5-carboxy-1-methylpyrazol-3-yl) oxyacetate (0.5 mmol) and EDCI (0.5 mmol) in methanol (20 mL) was added a solution of 1,3-diisobutyl-5,6-diaminouracil (0.5 mmol), dissolved in methanol (20 mL). The mixture was stirred at room temperature for two hours, the solvent was then removed in vacuo, water added, and the solid that formed was collected by filtration and washed with additional cold water. The intermediate amide was heated in 20 mL of 2.5 N NaOH at 70° C. for 30 minutes to afford the desired 2-[5-(1,3-diisobutyl-xanthin-8-yl)-1-methylpyrazol-3-yloxy]acetic acid.

Condensation of 2-[5-(1,3-diisobutyl-xanthin-8-yl)-1-methylpyrazol-3-yloxy]acetic acid (0.5 mmol) and 4-fluoroaniline (1.3 mmol) in the presence of EDCI (1.12 mmol) and HOBt (1.14 mmol) in anhydrous dimethylformamide afforded the desired product.

MP: 227-230° C.; $^1$H-NMR (DMSO-$d_6$): δ 0.87 (t, 12H, J=7.58Hz), 2.05 (bm, 2H), 3.74 (d, 2H, J=7.15 Hz), 3.85 (d, 2H, J=7.15), 4.06 (s, 2H), 4.76 (s, 2H), 6.51 (s, 1H), 7.16 (t, 2H), 7.64 (m, 2H), 10.17 (s, 1H), 13.96 (bs, 1H).

EXAMPLE 42

Preparation of Compound AS67

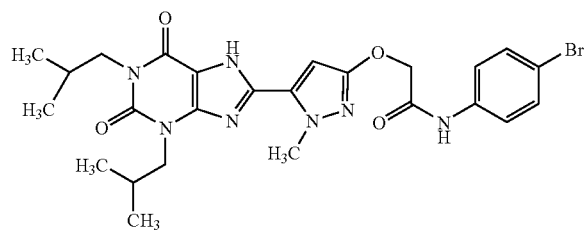

Condensation of 2-[5-(1,3-diisobutyl-xanthin-8-yl)-1-methylpyrazol-3-yloxy]acetic acid (Example 44, Compound AS35, 0.5 mmol) and 4-bromoaniline (1.3 mmol) in the presence of EDCI (1.12 mmol) and HOBt (1.14 mmol) in anhydrous dimethylformamide afforded the desired product.

MP: 258-260° C.; $^1$H-NMR (DMSO-$d_6$): δ 0.87 (t, 12H, J=7.22Hz), 2.06 (m, 2H), 3.77 (d, 2H, J=7.3 Hz), 3.85 (d, 2H, J=7.16), 4.06 (s, 3H), 4.77 (s, 2H), 6.51 (s, 1H), 7.52 (dd, 4H, J=8.88 Hz), 10.26 (s, 1H), 13.96 (s, 1H).

EXAMPLE 43

Preparation of Compound AS37

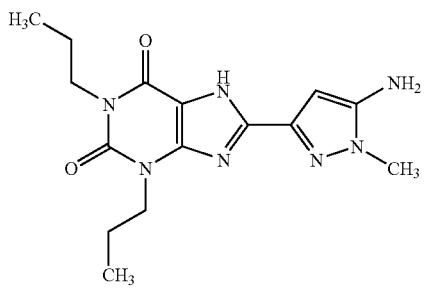

A solution of 1,3-dipropyl-5,6-diaminouracil (0.7 g, 0.003 mol), 1-methyl-5-(benzyloxycarbonylamino)-pyrazole-3-carboxylic acid (0.8 g, 0.003 mol), and EDCI (0.6 g, 0.003 mol) in 50 mL of CH$_3$OH was stirred at room temperature for two hours. Excess CH$_3$OH was evaporated in vacuo to give a yellow solid that was collected by filtration and washed with H$_2$O to give the amide intermediate.

A mixture of the amide intermediate and 30 mL of 2.5 N NaOH was warmed to 70-80° C. for three hours. The clear aqueous solution was cooled and acidified to pH 5 with concentrated HCl. The white precipitate that formed was collected by filtration and washed with H$_2$O to afford the desired 1,3-dipropyl-8-(5-amino-1-methylpyrazol-3-yl)xanthine, which was recrystallized from CH$_3$OH.

MP: 249-250° C.; $^1$H-NMR (DMSO-$d_6$): δ 0.85 (m, 6H), 1.59 (m, 2H), 1.72 (m, 2H), 3.50 (s, 3H), 3.85 (m, 2H), 3.95 (m, 2H), 5.50 (d, 2H), 6.00 (s,1H), 13.50 (s, 1H).

EXAMPLE 44

Preparation of Compound AS35

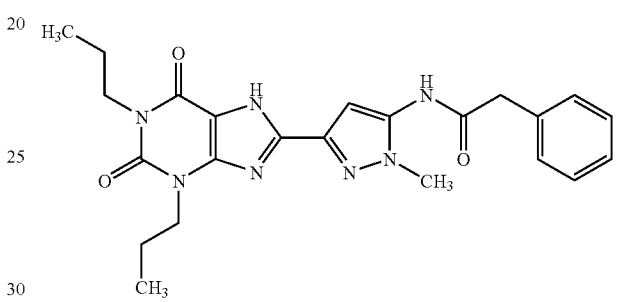

A solution of phenylacetic acid (0.196 mmol) in 3 mL of thionyl chloride was stirred at 70° C. for four hours, then excess thionyl chloride removed in a nitrogen stream. A solution of 1,3-dipropyl-8-(5-amino-1-methylpyrazol-3-yl) xanthine (0.151 mmol, Example 43) and 0.04 mL of anhydrous triethylamine in 10 mL of CH$_2$Cl$_2$: CH$_3$OH (1:1) was added and the mixture was stirred at room temperature for 24 hours, monitoring by TLC.

At completion, the solvent was evaporated, the residue dissolved in ethyl acetate, and the solution washed with saturated aqueous NaHCO$_3$ and brine. The organic layer was dried (Na$_2$SO$_4$), filtered, and evaporated in vacuo. The desired product was purified by column chromatography on silica gel.

MP: 279-281° C.; $^1$H-NMR (DMSO-$d_6$): δ 0.88 (m, 6H), 1.55 (m, 2H), 1.72 (m, 2H), 3.60 (s, 3H), 3.75 (s, 2H), 3.89 (t, 2H), 4.01 (t, 2H), 7.27 (s, 1H), 6.90 (s, 1H), 7.20 (m, 5H), 10.20 (s, 1H), 14.00 (s, 1H).

EXAMPLE 45

Preparation of Compound AS60

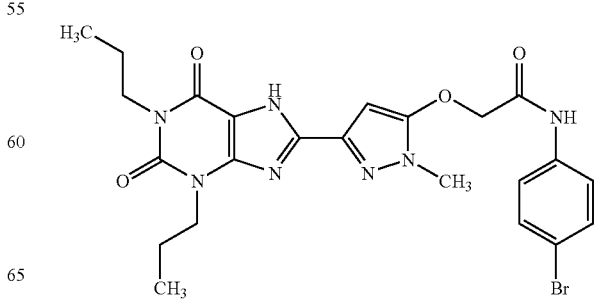

To a solution of ethyl (3-carboxy-1-methylpyrazol-5-yl) oxyacetate (0.5 mmol) and EDCI (0.5 mmol) in methanol (20 mL) was added a solution of 1,3-dipropyl-5,6-diaminouracil (0.5 mmol), dissolved in methanol (20 mL). The mixture was stirred at room temperature for two hours, the solvent was then removed in vacuo, water added, and the solid that formed was collected by filtration and washed with additional cold water. The intermediate amide was heated in 20 mL of 2.5 N NaOH at 70° C. for 30 minutes to afford the desired 2-[3-(1,3-dipropyl-xanthin-8-yl)-1-methylpyrazol-5-yloxy]acetic acid.

Condensation of 2-[3-(1,3-dipropyl-xanthin-8-yl)-1-methylpyrazol-5-yloxy]acetic acid (0.5 mmol) and 4-bromoaniline (1.3 mmol) in the presence of EDCI (1.12 mmol) and HOBt (1.14 mmol) in anhydrous dimethylformamide afforded the desired product.

MP: 242° C.; $^1$H-NMR (DMSO-$d_6$): δ 0.88 (m, 6H), 1.70 (m, 4H), 3.70 (s, 3H), 3.85 (t, 2H), 3.98 (t, 2H), 4.85 (s, 2H), 6.32 (s, 1H), 7.62 (dd, 4H, J=8 Hz), 10.33 (s, 1H), 13.70 (s, 1H).

EXAMPLE 46

Preparation of Compound AS61

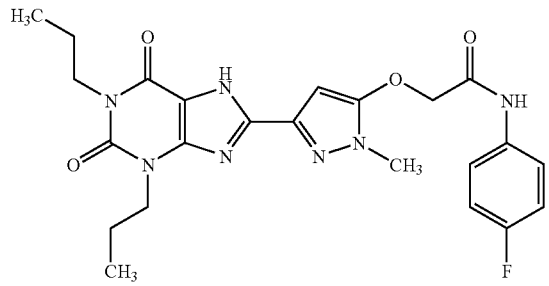

Condensation of 2-[3-(1,3-dipropyl-xanthin-8-yl)-1-methylpyrazol-5-yloxy]acetic acid (Example 45, 0.5 mmol) and 4-fluoroaniline (1.3 mmol) in the presence of EDCI (1.12 mmol) and HOBt (1.14 mmol) in anhydrous dimethylformamide afforded the desired product.

MP: 262° C.; $^1$H-NMR (DMSO-$d_6$): δ 0.88 (m, 6H), 1.70 (m, 4H), 3.70 (s, 3H), 3.85 (t, 2H), 3.98 (t, 2H), 4.85 (s, 2H), 6.32 (s, 1H), 7.18 (t, 2H, J=8.88Hz), 7.62 (m, 2H, J=6.92 Hz), 10.25 (s, 1H), 13.70 (s, 1H).

EXAMPLE 47

Preparation of Compound AS62

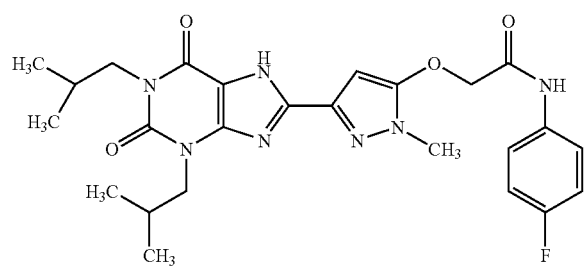

To a solution of ethyl (3-carboxy-1-methylpyrazol-5-yl) oxyacetate (0.5 mmol) and EDCI (0.5 mmol) in methanol (20 mL) was added a solution of 1,3-diisobutyl-5,6-diaminouracil (0.5 mmol), dissolved in methanol (20 mL). The mixture was stirred at room temperature for two hours, the solvent was then removed in vacuo, water added, and the solid that formed was collected by filtration and washed with additional cold water. The intermediate amide was heated in 20 mL of 2.5 N NaOH at 70° C. for 30 minutes to afford the desired 2-[3-(1,3-diisobutyl-xanthin-8-yl)-1-methylpyrazol-5-yloxy]acetic acid.

Condensation of 2-[3-(1,3-diisobutyl-xanthin-8-yl)-1-methylpyrazol-5-yloxy]acetic acid (0.5 mmol) and 4-fluoroaniline (1.3 mmol) in the presence of EDCI (1.12 mmol) and HOBt (1.14 mmol) in anhydrous dimethylformamide afforded the desired product.

MP: 251-252° C.; $^1$H-NMR (DMSO-$d_6$): δ 0.85 (t, 12H), 2.10 (m, 2H), 3.75 (s, 3H), 3.83 (dd, 4H), 4.86 (s, 2H), 6.32 (s, 1H), 7.18 (t, 2H, J=8.85 Hz), 7.62 (m, 2H, J=5.03 Hz), 13.70 (s, 1H).

EXAMPLE 48

Preparation of Compound AS63

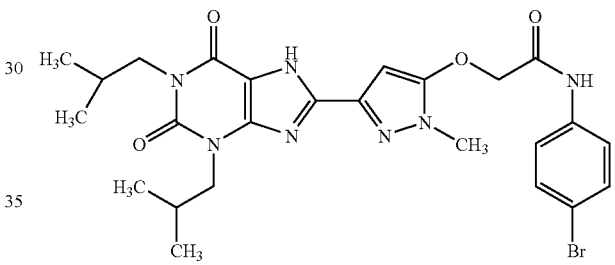

Condensation of 2-[3-(1,3-diisobutyl-xanthin-8-yl)-1-methyl-pyrazol-5-yloxy]acetic acid (xanthine intermediate from Example 47, 0.5 mmol) and 4-bromoaniline (1.3 mmol) in the presence of EDCI (1.12 mmol) and HOBt (1.14 mmol) in anhydrous dimethylformamide afforded the desired product.

MP: 234° C.; $^1$H-NMR (DMSO-$d_6$): δ 0.84 (t, 12H), 2.10 (m, 2H), 3.73 (s, 3H), 3.831 (dd, 4H), 4.85 (s, 2H), 6.26 (s, 1H), 7.53 (q, 4H), 10.36 (s, 1H), 13.64 (s, 1H).

EXAMPLE 49

Preparation of Compound AS4

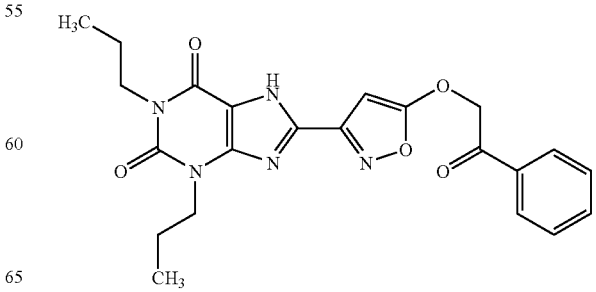

A solution of 1,3-dipropyl-5,6-diaminouracil (0.7 g, 0.003 mol), 3-(benzoyloxymethyl)-oxazole-5-carboxylic acid (0.8 g, 0.003 mol), and EDCl (0.6 g, 0.003 mol) in 50 mL of CH$_3$OH was stirred at room temperature for two hours. Excess CH$_3$OH was evaporated in vacuo to give a solid that was collected by filtration and washed with H$_2$O to afford the amide intermediate.

A mixture of the amide intermediate and 30 mL of 2.5 N NaOH was warmed to 70-80° C. for three hours. The clear aqueous solution was cooled and acidified to pH 5 with concentrated HCl. The white precipitate that formed was collected by filtration and washed with H$_2$O to afford the desired 1,3-dipropyl-8-[3-(benzoyloxymethyl)-oxazol-5-yl] xanthine, which was recrystallized from CH$_3$OH.

MP: 236-238° C.; $^1$H-NMR (DMSO-d$_6$): δ 0.96 (m, 6H), 1.49 (m, 2H), 1.59 (m, 2H), 3.88 (t, 2H), 3.98 (bs, 2H), 5.60 (s, 2H), 7.25 (s, 1H), 7.74 (m, 3H), 8.00 (m, 2H), 14.50 (s,1 H).

EXAMPLE 50

Preparation of Compound AS20

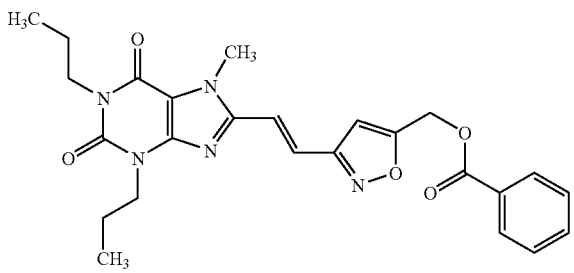

Using 1,3-dipropyl-5,6-diaminouracil and 3-[3-(benzoyloxymethyl)oxazol-5-yl]acrylic acid, the requisite intermediate was prepared, as described for Example 41. The product was treated with sodium hydride, followed by methyl iodide in THF to provide the desired product.

MP: 165° C.; $^1$H-NMR (DMSO-d$_6$): δ 0.85 (m, 6H), 1.59 (m, 2H), 1.72 (m, 2H), 3.85 (t, 2H), 3.98 (t, 2H), 4.03 (s, 3H), 5.50 (s, 2H), 7.30 (s, 1H), 7.57 (m, 3H), 7.59 (d, 2H, J=8Hz), 8.03 (d, 2H, J=8Hz).

EXAMPLE 51

Preparation of Compound AS53

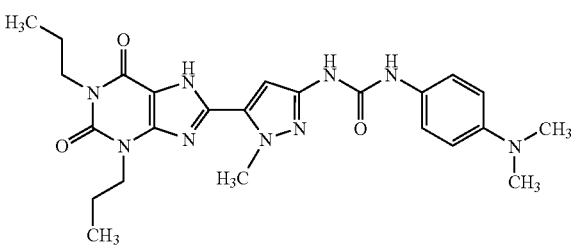

To a solution of 1,3-dipropyl-8-(3-amino-1-methylpyrazol-5-yl)xanthine (3 mmol, Example 1) in 1,4-dioxane at room temperature was added 4-(dimethylaminophenyl)isocyanate (3.2 mmol). The mixture was stirred overnight at room temperature, quenched by the addition of water, and the precipitated product collected by filtration. Purification was achieved by column chromatography on silica gel.

MP: 266-268° C.; $^1$H-NMR (DMSO-d$_6$): δ 0.87 (m, 6H), 1.50 (m, 2H), 1.60 (m, 2H), 2.80 (s, 6H), 3.83 (m, 2H), 3.98 (m, 2H), 4.10 (s, 3H), 6.69 (d, 11H, J=8.0 Hz), 6.94 (d, 1H, J=8.0 Hz), 7.1 (s, 1H), 7.27 (d, 2H, J=8.0 Hz), 8.64 (s, 1H), 8.98 (s, 1H).

EXAMPLE 52

Preparation of Compound AS54

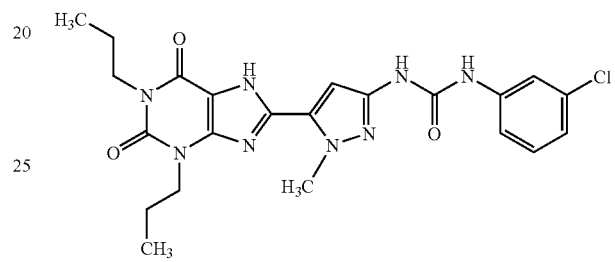

Using 3-chlorophenylisocyanate and 1,3-dipropyl-8-(3-amino-1-methyl-pyrazol-5-yl)xanthine (Example 1, Compound AS3).

MP: >300° C.; $^1$H-NMR (DMSO-d$_6$): δ 0.87 (m, 6H), 1.50 (m, 2H), 1.60 (m, 2H), 3.83 (m, 2H), 3.98 (m, 2H), 4.10 (s, 3H), 7.01 (m, 1H), 7.19 (s, 1H), 7.30 (m, 2H), 7.70 (s, 1H), 9.03 (s, 1H), 9.15 (s, 1H), 14.0 (s, 1H).

EXAMPLE 53

Preparation of Compound AS55

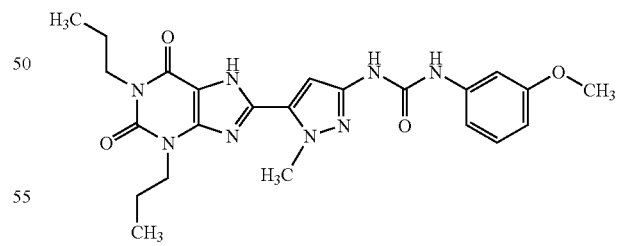

Using 3-(methoxy)phenylisocyanate and 1,3-dipropyl-8-(3-amino-1-methylpyrazol-5-yl)xanthine (Example 1, Compound AS3).

MP: >300° C.; $^1$H-NMR (DMSO-d$_6$): δ 0.87 (m, 6H), 1.50 (m, 2H), 1.60 (m, 2H), 3.82 (s, 3H), 3.86 (m, 2H), 3.98 (m,2H), 4.10 (s, 3H), 6.54 (d, 1H, J=8.0 Hz), 6.90 (d, 1H, J=8.0 Hz), 7.10 (s, 1H), 7.24 (m, 2H), 8.90 (s, 1H), 9.07 (s, 1H), 14.0 (s, 1H,

EXAMPLE 54

Preparation of Compound AS49

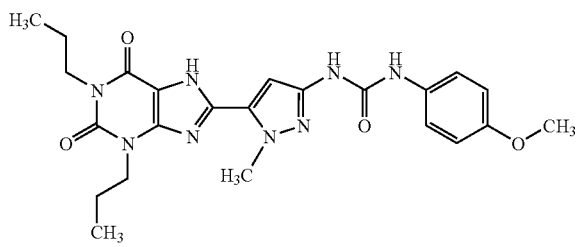

Using 4-(methoxy)phenylisocyanate and 1,3-dipropyl-8-(3-amino-1-methylpyrazol-5-yl)xanthine (Example 1, Compound AS3).

Yield: 98% MP: >300° C.; 1H NMR (DMSO-$d_6$): δ 0.80 (m, 6H); 1.62 (m, 2H); 1.70 (m, 2H); 3.68 (s, 3H); 3.75 (m, 2H); 4.02 (m, 2H); 4.22 (s, 3H); 7.00 (d, 2H, J=8.00 Hz); 7.25 (s, 1H); 7.32 (d, 2H, J=8.00 Hz); 8.82 (s, 1H); 8.95 (S, 1H); 14.01 (s, 1H).

EXAMPLE 55

Preparation of Compound AS1

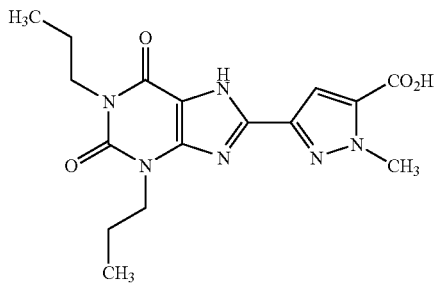

To a solution of 1,3-dipropyl-5,6-diaminouracil (2.2 mmol) in methanol (10 mL) was added an equimolar amount of 1-methyl-1H-pyrazole-3,5-dicarboxylic acid 5-ethyl ester and DCI (2.21 mmol). The reaction mixture was stirred at room temperature for 4-5 h with monitoring by TLC. At completion, the reaction mixture was concentrated in vacuo and water added. The intermediate amide precipitated and was collected by filtration. The solid thus collected was dissolved in methanol (10 mL), 2.5 N NaOH (15 mL) added, and the mixture heated to 70-80° C. for 12 hours. After removal of the methanol, the residue was taken up in water, acidified to pH 4-5 with HCl, and the resultant precipitate collected by filtration. The desired product was purified by flash chromatography on silica gel, eluting with ethyl acetate/petroleum ether.

Yield: 40%; MP: >300° C.; 1H NMR (DMSO-$d_6$): δ 0.93 (m, 6H); 1.58 (m, 2H), 1.75 (m, 2H); 3.88 (m, 2H); 3.98 (m, 2H); 4.01 (s, 3H); 7.43 (s,1H); 13.60 (bs, 2H).

EXAMPLE 56

Preparation of Compound AS91

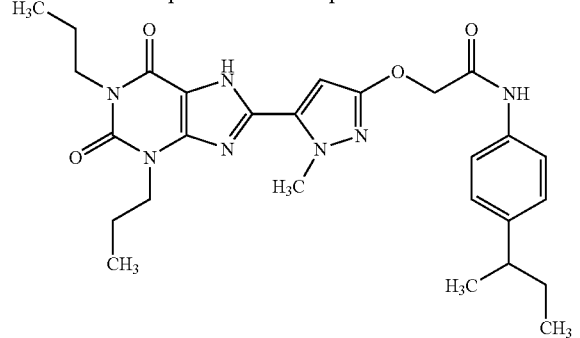

Using 4-(sec-butyl)aniline and 2-[5-(1,3-dipropyl-xanthin-8-yl)-1-methylpyrazol-3-yloxy]acetic acid (Example 36), according to the method described in Example 36.

Yield: 36%; MP: 240-242° C.; 1H NMR (DMSO-$d_6$): δ 0.74 (t, 3H, J=8.00); 0.85 (m, 9H); 1.15 (d, 3H, J=8.00); 1.51 (m, 2H); 1.55 (m, 2H); 3.86 (m, 2H); 4.00 (m, 2H); 4.06 (s, 3H); 4.74 (s, 2H); 6.50 (s, 1H); 7.12 (d, 2H, J=8.00); 7.52 (d, 2H, J=8.00); 10.02 (s, 1H); 13.93 (s, 1H).

EXAMPLE 57

Preparation of Compound AS92

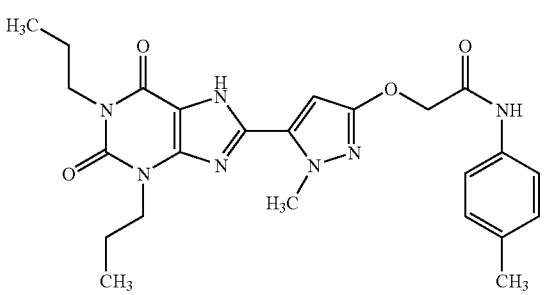

Using 4-(methyl)aniline and 2-[5-(1,3-dipropyl-xanthin-8-yl)-1-methylpyrazol-3-yloxy]acetic acid (Example 36), according to the method described in Example 36.

Yield: 38%; MP: 256-257° C.; 1H NMR (DMSO-$d_6$): δ 0.87 (m, 6H); 1.56 (m, 2H); 1.73 (m, 2H); 2.24 (s, 3H); 3.84 (m, 2H); 3.94 (m, 2H); 4.05 (s, 3H); 4.74 (s, 2H); 6.51 (s, 1H); 7.12 (d, 2H, J=8.10); 7.50 (d, 2H, J=8.15); 10.01 (s, 1H); 13.94 (s, 1H).

EXAMPLE 58

Preparation of Compound AS93

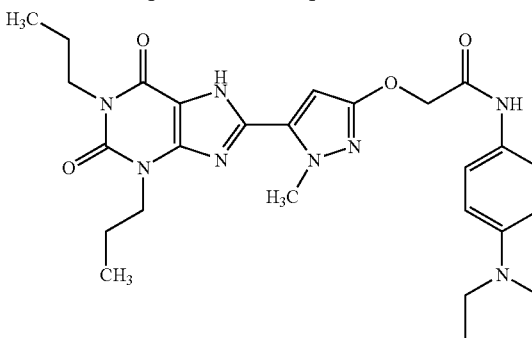

Using 4-(N-morpholino)aniline and 2-[5-(1,3-dipropyl-xanthin-8-yl)-1-methylpyrazol-3-yloxy]acetic acid (Example 36), according to the method described in Example 36.

Yield: 46%; MP: 296-298° C.; 1H NMR (DMSO-$d_6$): δ 0.87 (m, 6H); 1.57 (m, 2H); 1.75 (m, 2H); 3.03 (m, 4H); 3.71 (m, 4H); 3.74 (m, 2H); 3.85 (m, 2H); 4.03 (s, 3H); 4.71 (s, 2H); 6.46 (s, 1H); 6.89 (d, 2H, J=8.27); 7.48 (d, 2H, J=8.22); 9.89 (s, 1H); 13.86 (bs, 1H).

EXAMPLE 59

Preparation of Compound AS94

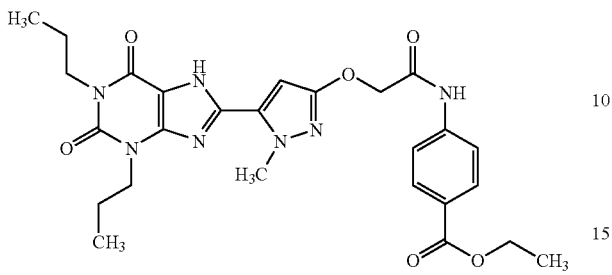

Using ethyl 4-(amino)benzoate and 2-[5-(1,3-dipropyl-xanthin-8-yl)-1-methylpyrazol-3-yloxy]acetic acid (Example 36), according to the method described in Example 36.

Yield: 48%; MP: 294° C.; 1H NMR (DMSO-$d_6$): δ 0.87 (m, 6H); 1.30 (m, 3H, J=8.00); 1.58 (m, 2H); 1.62 (m, 2H); 3.85 (m, 2H); 3.96 (m, 2H); 4.03 (s, 3H); 4.24 (q, 2H, J=8.00); 4.80 (s, 2H); 6.44 (s, 1H); 7.77 (d, 2H, J=8.00); 7.92 (d, 2H, J=8.00); 10.46 (s, 1H); 13.92 (s, 1H).

EXAMPLE 60

Preparation of Compound AS95

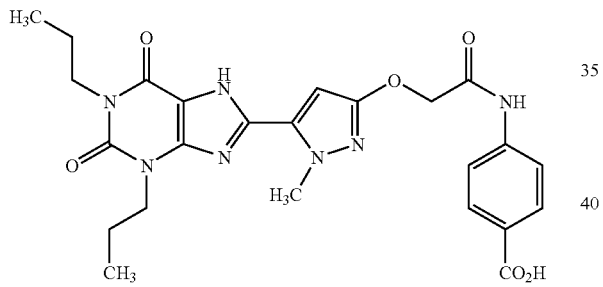

Using 4-(amino)benzoic acid and 2-[5-(1,3-dipropyl-xanthin-8-yl)-1-methylpyrazol-3-yloxy]acetic acid (Example 36), according to the method described in Example 36.

Yield: 38%; MP: >300° C.; 1H NMR (DMSO-$d_6$): δ 0.88 (m, 6H); 1.56 (m, 2H); 1.73 (m, 2H); 3.86 (m, 2H); 3.98 (m, 2H); 4.06 (s, 3H); 4.81 (s, 2H); 6.49 (s, 1H); 7.74 (d, 2H, J=8.70); 7.80 (d, 2H, J=8.58); 10.44 (s, 1H); 13.92 (s, 1H).

EXAMPLE 61

Preparation of Compound AS99

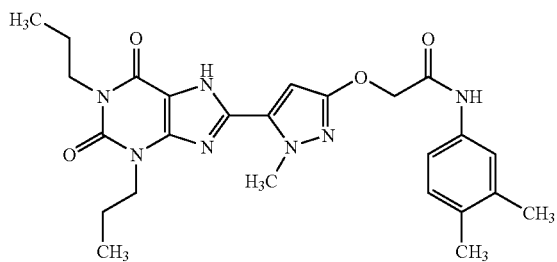

Using 3,4-dimethylaniline and 2-[5-(1,3-dipropyl-xanthin-8-yl)-1-methylpyrazol-3-yloxy]acetic acid (Example 36), according to the method described in Example 36.

Yield: 65%; MP: 264-265° C.; 1H NMR (DMSO-$d_6$): δ 0.88 (m, 6H); 1.57 (m, 2H); 1.73 (m, 2H); 2.16 (m, 6H); 3.83 (m, 2H); 3.98 (m, 2H); 4.06 (s, 3H); 4.73 (s, 2H); 6.51 (s, 1H); 7.31 (m, 1H); 7.34 (m, 2H); 9.93 (s, 1H); 13.90 (s, 1H).

EXAMPLE 62

Preparation of Compound AS100

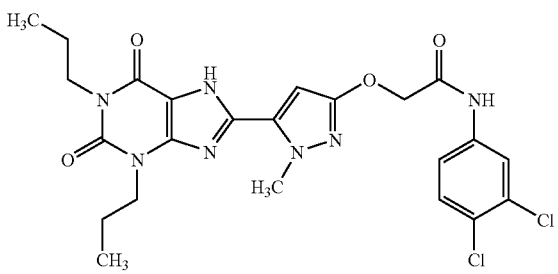

Using 3,4-dichloroaniline and 2-[5-(1,3-dipropyl-xanthin-8-yl)-1-methylpyrazol-3-yloxy]acetic acid (Example 36), according to the method described in Example 36.

Yield: 55%; MP: 258° C.; $^1$H NMR (DMSO-$d_6$): δ 0.88 (m, 6H); 1.57 (m, 2H); 1.72 (m, 2H); 3.84 (m, 2H); 4.00 (m, 2H); 4.06 (s, 3H); 4.78 (s, 2H); 6.52 (s, 1H); 7.57 (s, 2H); 8.02 (s, 1H); 10.42 (s, 1H); 13.94 (s, 1H).

EXAMPLE 63

Preparation of Compound AS101

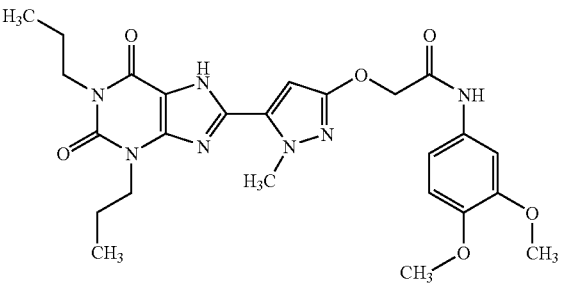

Using 3,4-dimethoxyaniline and 2-[5-(1,3-dipropyl-xanthin-8-yl)-1-methylpyrazol-3-yloxy]acetic acid (Example 36), according to the method described in Example 36.

Yield: 60%; MP: 291-293° C.; $^1$H NMR (DMSO-$d_6$): δ 0.88 (m, 6H); 1.59 (m, 2H); 1.77 (m, 2H); 3.71 (m, 6H); 3.87 (m, 2H); 4.00 (m, 2H); 4.07 (s, 3H); 4.73 (s, 2H); 6.51 (s, 1H); 6.89 (m, 1H); 7.14 (m, 1H); 7.33 (m, 1H); 9.95 (s, 1H); 13.97 (s, 1H).

EXAMPLE 64

Preparation of Compound AS89

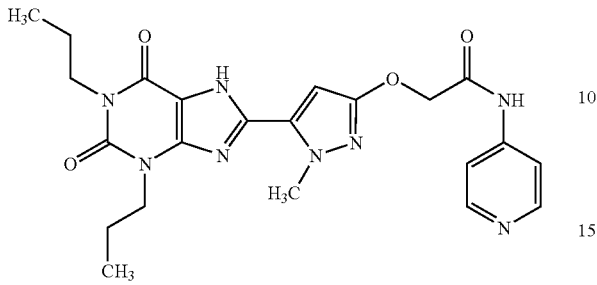

Using 4-aminopyridine and 2-[5-(1,3-dipropyl-xanthin-8-yl)-1-methylpyrazol-3-yloxy]acetic acid (Example 36), according to the method described in Example 36.

Yield: 35%; MP: 248-251° C.; $^1$H NMR (DMSO-$d_6$): δ0.9 (m, 6H); 1.55 (m, 2H); 1.67 (m, 2H); 3.89 (m, 2H); 4.00 (m, 2H); 4.05 (s, 3H); 4.82 (s, 2H); 6.44 (s, 1H); 7.64 (d, 2H, J=8.80); 7.93 (d, 2H, J=8.92); 10.43 (s, 1H); 13.95 (bs, 1H).

EXAMPLE 65

Preparation of AS70

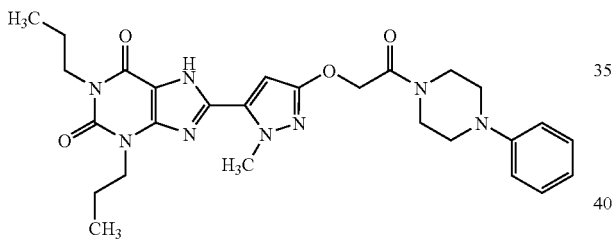

Using N-phenyl-piperazine and 2-[5-(1,3-dipropyl-xanthin-8-yl)-1-methylpyrazol-3-yloxy]acetic acid (Example 36), according to the method described in Example 36.

Yield: 38%; MP: 273-274° C.; $^1$H NMR (DMSO-$d_6$): δ 0.87 (m, 6H); 1.69 (m, 2H); 1.71 (m, 2H); 3.18 (m, 4H); 3.57 (m, 4H); 3.86 (m, 2H); 4.00 (m, 2H); 4.05 (s, 2H); 6.46 (s, 1H); 6.81 (m, 1H); 6.96 (d, 2H, J=8.00); 7.21 (t, 2H, J=8.00); 13.92 (s, 1H).

EXAMPLE 66

Preparation of AS72

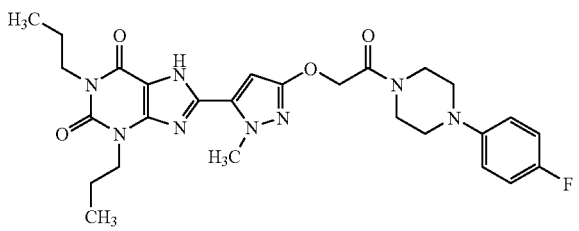

Using N-(4-fluorophenyl)-piperazine and 2-[5-(1,3-dipropyl-xanthin-8-yl)-1-methylpyrazol-3-yloxy]acetic acid (Example 36), according to the method described in Example 36.

Yield: 40%; MP: 235-237° C.; $^1$H NMR (DMSO-$d_6$): δ 0.87 (m, 6H); 1.57 (m, 2H); 1.74 (m, 2H); 3.09 (m, 4H); 3.84 (m, 2H); 3.95 (m, 2H); 4.05 (s, 3H); 4.92 (s, 2H); 6.46 (s, 1H); 7.01 (m, 4H); 13.92 (s, 1H).

EXAMPLE 67

Preparation of AS87

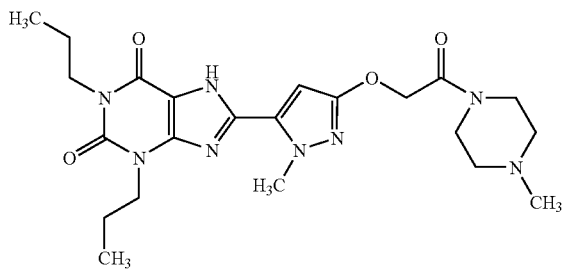

Using N-methyl-piperazine and 2-[5-(1,3-dipropyl-xanthin-8-yl)-1-methylpyrazol-3-yloxy]acetic acid (Example 36), according to the method described in Example 36.

Yield: 56%; MP: 192-194° C.; $^1$H NMR (DMSO-$d_6$): δ 0.87 (m, 6H); 1.06 (m, 2H); 1.20 (m, 2H); 2.39 (m, 4H); 3.39 (m, 4H); 3.75 (m, 2H); 3.90 (s, 3H); 4.12 (m, 2H); 4.04 (s, 3H); 4.85 (s, 2H); 6.92 (s, 1H); 13.92 (s, 1H).

EXAMPLE 68

Preparation of AS90

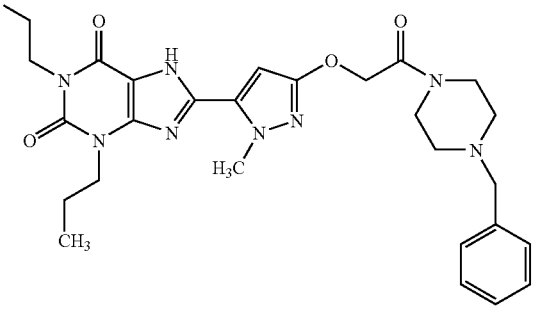

Using N-benzyl-piperazine and 2-[5-(1,3-dipropyl-xanthin-8-yl)-1-methylpyrazol-3-yloxy]acetic acid (Example 36), according to the method described in Example 36.

Yield: 32%; MP: 236-237° C.; $^1$H NMR (DMSO-$d_6$): δ 0.87 (m, 6H); 1.08 (m, 2H); 1.12 (m, 2H); 2.39 (m, 4H); 3.39 (m, 4H); 3.50 (s, 2H); 3.86 (m, 2H); 4.00 (m, 2H), 4.04 (s, 3H); 4.85 (s, 2H); 6.42 (s, 1H); 7.31 (m, 5H); 13.92 (s, 1H).

EXAMPLE 69

Preparation of AS96

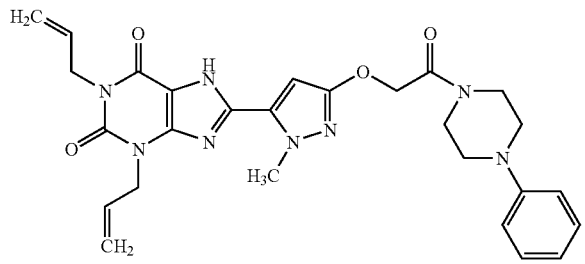

To a solution of ethyl (5-carboxy-1-methylpyrazol-3-yl)oxyacetate (0.5 mmol) and EDCI (0.5 mmol) in methanol (20 mL) was added a solution of 1,3-diallyl-5,6-diaminouracil (0.5 mmol), dissolved in methanol (20 mL). The mixture was stirred at room temperature for two hours, the solvent was then removed in vacuo, water added, and the solid that formed was collected by filtration and washed with additional cold water. The intermediate amide was heated in 20 mL of 2.5 N NaOH at 70° C. for 30 minutes to afford the desired 2-[5-(1,3-diallyl-xanthin-8-yl)-1-methylpyrazol-3-yloxy]acetic acid.

Condensation of 2-[5-(1,3-diallyl-xanthin-8-yl)-1-methylpyrazol-3-yloxy]acetic acid (0.5 mmol) and N-phenylpiperazine (1.3 mmol) in the presence of EDCI (1.12 mmol) and HOBt (1.14 mmol) in anhydrous dimethylformamide afforded the desired product.

Yield: 27%; MP: 289-290° C.; $^1$H NMR (DMSO-$d_6$): δ 3.17 (m, 4H); 3.57 (m, 4H); 4.05 (s, 3H); 4.51 (m, 2H); 4.64 (m, 2H); 4.93 (s, 2H); 5.11 (m, 4H); 5.89 (m, 2H); 6.46 (s, 1H); 6.81 (m, 1H); 6.96 (d, 2H, J=8.13); 7.23 (t, 2H, J=8.00); 14.00 (s, 1H).

EXAMPLE 70

Preparation of AS105

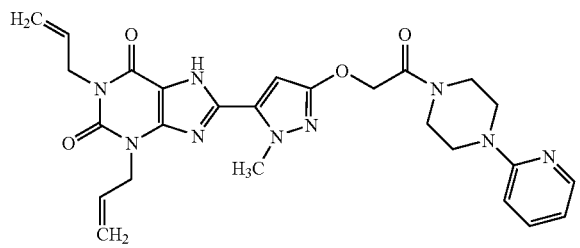

Using N-(pyridin-2-yl)-piperazine and 2-[5-(1,3-diallyl-xanthin-8-yl)-1-methylpyrazol-3-yloxy]acetic acid (Example 69), according to the method described in Example 69.

EXAMPLE 71

Preparation of AS106

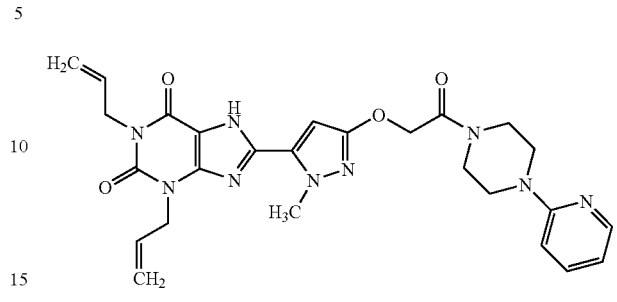

Using N-(pyrimidin-2-yl)-piperazine and 2-[5-(1,3-diallyl-xanthin-8-yl)-1-methylpyrazol-3-yloxy]acetic acid (Example 69), according to the method described in Example 69.

EXAMPLE 72

Preparation of AS109

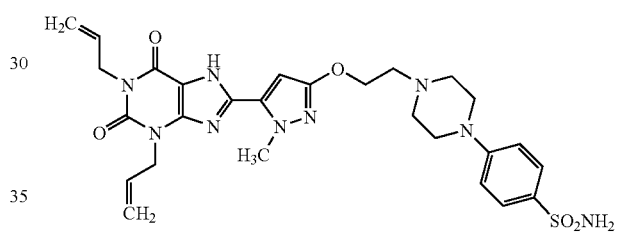

Using N-(4-sulfonamidophenyl)-piperazine and 2-[5-(1,3-diallyl-xanthin-8-yl)-1-methylpyrazol-3-yloxy]acetic acid (Example 69), according to the method described in Example 69.

EXAMPLE 73

Preparation of ethyl (5-(methoxycarbonyl)-isoxazol-3-yl)oxyacetate

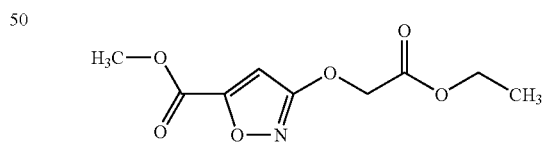

To a solution of methyl 3-hydroxy-isoxazole-5-carboxylate (7.14 mmol) in acetone (30 mL), was added potassium carbonate (1.2 g, 8.6 mmol) and ethyl bromoacetate (8.6 mmol). The reaction mixture was heated at reflux for 2 h, monitoring by TLC. At completion, acetone was removed in vacuo and the residue partitioned between water and ethyl acetate (50 mL). The organic layer was dried (MgSO$_4$), filtered, and evaporated to afford the desired intermediate.

Yield: 81%; MP: 66-67° C.; $^1$H NMR (CDCl$_3$): δ 1.30 (t, 3H, J=7.22); 3.96 (s, 3H); 4.27 (q, 2H, J=7.21); 4.87 (s, 2H); 6.65 (s, 1H).

EXAMPLE 74

Preparation of (5-carboxyisoxazol-3-yl)oxyacetic Acid

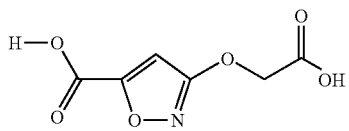

A solution of ethyl (5-(methoxycarbonyl)isoxazol-3-yl)oxyacetate (4 mmol, Example 73) in methanol (60 mL) and 5% aqueous NaOH is heated at reflux for 1 hour. At the end of this time, the methanol is removed, the residue diluted with additional water, and acidified to pH=4 with hydrochloric acid. The resulting precipitate is collected by filtration, washed with cold water, and dried.

Yield: 90%; MP: >300° C.; $^1$H NMR (DMSO-d$_6$): 0 4.71 (s, 2H); 6.22 (s, 1H); 11.30 (bs, 1H); 14.75 (bs, 1H).

EXAMPLE 75

Preparation of ethyl (5-carboxyisoxazol-3-yl)oxyacetate

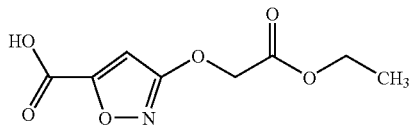

(5-Carboxyisoxazol-3-yl)oxyacetic acid (4.0 mmol, Example 74) is dissolved in ethanol (50 mL), to which is added a catalytic amount of p-toluenesulfonic acid (100 mg). After stirring overnight at room temperature, the ethanol was removed and the residue was recrystallized from ethanol/water.

Yield: 70%; MP: 145-150° C.; $^1$H NMR (CDCl$_3$): [1.40 (t, 3H, J=7.18); 4.20 (q, 2H, J=7.21); 4.90 (s, 2H); 6.75 (s, 1H); 11.35 (bs, 1H).

EXAMPLE 76

Preparation of AS74

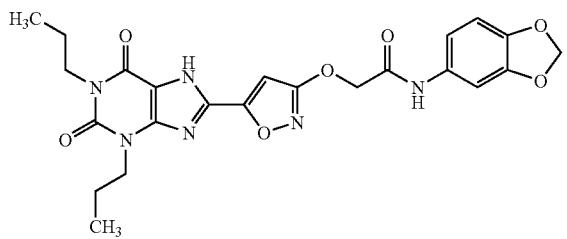

To a solution of ethyl (5-carboxyisoxazol-3-yl)oxyacetate (0.5 mmol) and EDCI (0.5 mmol) in methanol (20 mL) was added a solution of 1,3-dipropyl-5,6-diaminouracil (0.5 mmol), dissolved in methanol (20 mL). The mixture was stirred at room temperature for two hours, the solvent was then removed in vacuo, water added, and the solid that formed was collected by filtration and washed with additional cold water. The intermediate amide was heated in 20 mL of 2.5 N NaOH at 70° C. for 30 minutes to afford the desired 2-[5-(1,3-dipropyl-xanthin-8-yl)-isoxazol-3-yloxy]acetic acid.

Condensation of 2-[5-(1,3-dipropyl-xanthin-8-yl)-isoxazol-3-yloxy]acetic acid (0.5 mmol) and 3,4-methylenedioxyaniline (1.3 mmol) in the presence of EDCI (1.12 mmol) and HOBt (1.14 mmol) in anhydrous dimethylformamide afforded the desired product.

EXAMPLE 77

Preparation of AS76

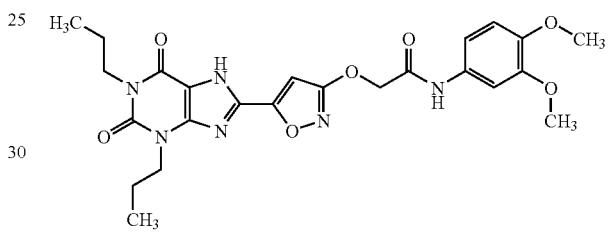

Using 3,4-dimethoxyaniline and 2-[5-(1,3-dipropyl-xanthin-8-yl)-isoxazol-3-yloxy]acetic acid (Example 76), according to the method described in Example 76.

Yield: 36%; MP: 253-255° C.; $^1$H NMR (DMSO-d$_6$): δ 0.88 (m, 6H); 1.55 (m, 2H); 1.70 (m, 2H); 3.72 (s, 6H); 3.85 (m, 2H); 3.97 (m, 2H); 4.90 (s, 2H); 6.90 (m, 2H); 7.12 (m, 1H); 7.30 (s, 1H); 10.10 (bs, 1H); 14.60 (bs, 1H).

EXAMPLE 78

Preparation of AS73

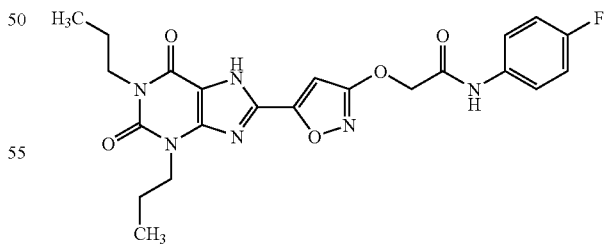

Using 4-fluoroaniline and 2-[5-(1,3-dipropyl-xanthin-8-yl)-isoxazol-3-yloxy]acetic acid (Example 76), according to the method described in Example 76.

Yield: 28%; MP: 287° C.; $^1$H NMR (DMSO-d$_6$): δ 0.88 (m, 6H); 1.55 (m, 2H); 1.70 (m, 2H); 3.85 (m, 2H); 3.97 (m, 2H); 4.93 (s, 2H); 6.90 (s, 1H); 7.18 (m, 2H); 7.62 (m, 2H); 10.29 (bs, 1H); 14.60 (bs, 1H).

EXAMPLE 79

Preparation of AS75

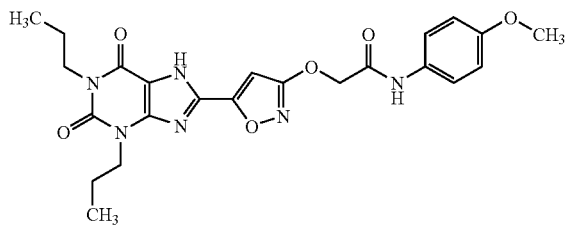

Using 4-methoxyaniline and 2-[5-(1,3-dipropyl-xanthin-8-yl)-isoxazol-3-yloxy]acetic acid (Example 76), according to the method described in Example 76.

Yield: 38%; MP: 285-287° C.; $^1$H NMR (DMSO-d$_6$): δ 0.88 (m, 6H); 1.59 (m, 2H); 1.68 (m, 2H); 3.71 (s, 3H); 3.85 (m, 2H); 3.97 (m, 2H); 4.90 (s, 2H); 6.91 (m, 3H); 7.50 (m, 2H); 10.09 (s, 1H); 14.56 (bs, 1H).

EXAMPLE 80

Preparation of 2-bromo-N-(4-iodophenyl)acetamide

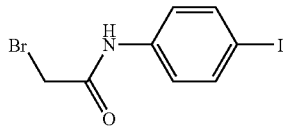

To a solution of 4-iodoaniline (14.5 mmol) in anhydrous dichloromethane at 0° C. was added a-bromo-acetylbromide (1.4 mL) and triethylamine (15 mmol). The mixture was warmed to room temperature, stirred for 1 h, the solvent removed, and residue dissolved in 5% hydrochloric acid. The aqueous solution was extracted with ethyl acetate, the organic layer washed with brine, dried (Na2SO4), filtered, and evaporated. The solid residue was purified by recrystallization form ethyl acetate to afford the desired intermediate.

Yield: 60%; MP: 185° C.; $^1$H NMR (CDCl$_3$): δ 4.93 (s, 2H); 8.24 (d, 2H, J=8.00); 8.58 (d, 2H, J=8.00); 9.02 (bs,1H).

EXAMPLE 81

Preparation of 1,3-dipropyl-8-(6-hydroxy-pyridazin-3-yl)-xanthine

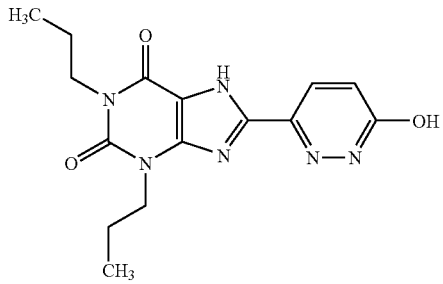

To a solution of 1,3-dipropyl-5,6-diaminouracil (2.2 mmol) in methanol was added an equimolar amount of 6-hydroxy-pyridazine-3-carboxylic acid, followed by a slight excess of DCl ((N-(3-(dimethylamino)propyl)-N'ethylcarbodiimide hydrochloride). The mixture was stirred at room temperature for 4-5 hours until complete by TLC. Water was then added and the precipitate removed by filtration. The solid was dissolved in 10% aqueous NaOH (20 mL), then heated at 70° C. for 30 minutes. After cooling to room temperature, the reaction mixture was acidified to pH=5 with 10% hydrochloric acid and the precipitated product collected by filtration.

Yield: 30%; MP: 216° C.; $^1$H NMR (DMSO-d$_6$): δ 0.87 (m, 6H); 1.65 (m, 4H); 3.5 (bs, 1H); 3.84 (m, 2H); 3.97 (m, 2H); 6.99 (d, 1H); 8.04 (d, 1H); 13.32 (bs, 1H).

EXAMPLE 82

Preparation of AS85

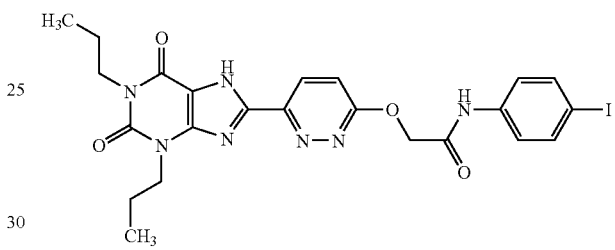

To a solution of 1,3-dipropyl-8-(6-hydroxy-pyridazin-3-yl)-xanthine (0.20 mmol, Example 81) in anhydrous dimethylformamide (10 mL) was added an equimolar amount of triethylamine. The reaction mixture was stirred at room temperature for 10 minutes, followed by the addition of 2-bromo-N-(4-iodophenyl)acetamide (0.20 mmol, Example 80). After stirring at room temperature overnight, the solvent was distilled off, the residue was taken up in cold water, and the precipitated product collected by filtration. The product was further purified by column chromatography on silica gel, eluting with a mixture of dichloromethane and metha- Yield: 28%; MP: 310° C.; $^1$H NMR (DMSO-d$_6$): δ 0.86 (m, 6H); 1.55 (m, 2H); 1.76 (m, 2H); 3.80 (m, 2H); 4.03 (m, 2H); 5.58 (s, 2H); 7.04 (d, 1H, J=9.92); 7.37 (d, 2H, J=8.64); 7.65 (d, 2H, J=8.55); 8.09 (d, 1H, J=10.01); 10.45 (s,1H); 13.30 (bs,1H). nol.

EXAMPLE 83

Preparation of AS103

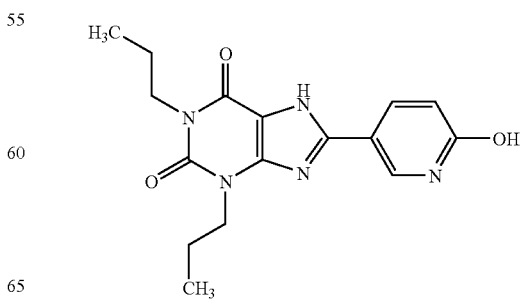

To a solution of 1,3-dipropyl-5,6-diaminouracil (2.2 mmol) in methanol was added an equimolar amount of 2-hydroxy-pyridine-5-carboxylic acid, followed by a slight excess of DCl ((N-(3-(dimethylamino)propyl)-N'-ethylcarbodiimide hydrochloride). The mixture was stirred at room temperature for 4-5 hours until complete by TLC. Water was then added and the precipitate removed by filtration. The solid was dissolved in 10% aqueous NaOH (20 mL), then heated at 70° C. for 30 minutes. After cooling to room temperature, the reaction mixture was acidified to pH=5 with 10% hydrochloric acid and the precipitated product collected by filtration.

Yield: 25%; MP: >300° C.; $^1$H NMR (DMSO-d$_6$): δ 0.88 (m, 6H); 1.60 (m, 4H);3.84 (bs,1H); 3.84 (m, 2H); 3.97 (m, 2H); 6.47 (d, 1H); 8.08 (m,1H); 8.20 (m, 1H); 13.30 (bs, 1H).

EXAMPLE 84

Preparation of AS81

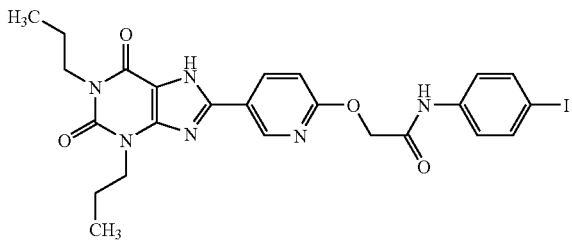

To a solution of 1,3-dipropyl-8-(2-hydroxy-pyridin-5-yl)-xanthine (0.20 mmol, Example 81) in anhydrous dimethylformamide (10 mL) was added an equimolar amount of triethylamine. The reaction mixture was stirred at room temperature for 10 minutes, followed by the addition of 2-bromo-N-(4-iodophenyl)acetamide (0.20 mmol, Example 80). After stirring at room temperature overnight, the solvent was distilled off, the residue was taken up in cold water, and the precipitated product collected by filtration. The product was further purified by column chromatography on silica gel, eluting with a mixture of dichloromethane and methanol.

Yield: 25%; MP: 293° C.; $^1$H NMR (DMSO-d$_6$): δ 0.86 (m, 6H); 1.55 (m, 2H); 1.76 (m, 2H); 3.80 (m, 2H); 3.89 (m, 2H); 5.21 (s, 2H); 6.37 (d, 1H, J=9.46); 7.45)d,

EXAMPLE 85

Preparation of Compound AS68a

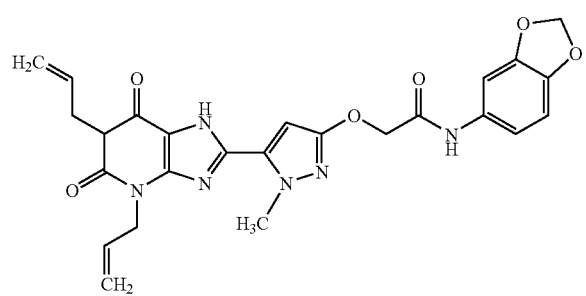

To a solution of ethyl (5-carboxy-1-methylpyrazol-3-yl) oxyacetate (0.5 mmol) and EDCI (0.5 mmol) in methanol (20 mL) was added a solution of 1,3-diallyl-5,6-diaminouracil (0.5 mmol), dissolved in methanol (20 mL). The mixture was stirred at room temperature for two hours, the solvent was then removed in vacuo, water added, and the solid that formed was collected by filtration and washed with additional cold water. The intermediate amide was heated in 20 mL of 2.5 N NaOH at 70° C. for 30 minutes to afford the desired 2-[5-(1,3-diallyl-xanthin-8-yl)-1-methylpyrazol-3-yloxy]acetic acid.

Condensation of 2-[5-(1,3-diallyl-xanthin-8-yl)-1-methylpyrazol-3-yloxy]acetic acid (0.5 mmol) and 3,4-methylenedioxyaniline (1.3 mmol) in the presence of EDCI (1.12 minoR) and HOBt (1.14 mmol) in anhydrous dimethylformamide afforded the desired product.

MP: 288-289° C.; 1H-NMR (DMSO-d$_6$): δ 2.50 (s, 3H), 4.51 (d, 2H), 4.62 (d, 2H), 4.72 (s, 2H), 5.07 (d, 1H), 5.10 (d, 1H), 5.15 (s, 1H), 5.18 (d, 1H), 5.90 (m, 2H), 5.98 (s, 2H), 6.51 (s, 1H), 6.87 (d, 1H, J=8.44Hz), 7.01 (d, 1H), 7.32 (s, 1H), 10.01 (s, 1H); 14.01 (bs, 1H).

Preparation of Radioligand Compounds

The compounds can be labeled with any suitable radiolabel. Examples of suitable radiolabels include tritium ($^3$H) and carbon radioisotopes (e.g. $^{14}$C), but any substantially non-toxic radiolabel commonly used in pharmacokinetic studies can be used. Means for incorporating radiolabels onto organic compounds are well known to those of skill in the art.

When the compounds are synthesized from a starting 1,3-dialkyl-5,6-diaminouracil, incorporation of a radiolabel is fairly straightforward. For example, the diaminouracil can be obtained containing a suitable radiolabel. As an alternate, the diaminouracil can be obtained with one or more sites of unsaturation in an attached substituent (e.g. iso-propylene in place of isopropyl). The unsaturated double bond can then be reacted with tritium in the presence a suitable catalyst, for example, palladium on charcoal or other known hydrogenation catalysts. Using the radiolabelled diaminouracil and following the methods of synthesis herein described will result in the corresponding radiolabelled compound.

It has been established by the inventors, as well as known by those skilled in the art, that $^3$H and $^{14}$C labeled compounds have binding affinity to the adenosine $A_1$, $A_{2A}$, $A_{2B}$, and $A_3$ $A_{2B}$, and $A_3$ receptor subtypes comparable to that of corresponding non-labeled forms.

EXAMPLE 86

Preparation of Radioligand of Compound AS16

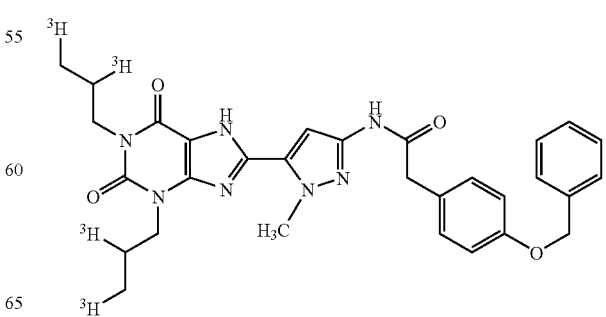

A solution of 1,3-diallyl-5,6-diaminouracil (0.7 g, 0.003 mol), 1-methyl-3-(benzyloxycarbonylamino)-pyrazole-5-carboxylic acid (0.8 g, 0.003 mol), and EDCl (0.6 g, 0.003 mol) in 50 mL of $CH_3OH$ is stirred at room temperature for two hours. Excess $CH_3OH$ is evaporated in vacuo to give a yellow solid that is collected by filtration and washed with $H_2O$ to give the amide intermediate.

A mixture of the amide intermediate and 30 mL of 2.5 N NaOH is warmed to 70-80° C. for three hours. The clear aqueous solution is cooled and acidified to pH 5 with concentrated HCl. The white precipitate that forms is collected by filtration and washed with $H_2O$ to afford the desired 1,3-diallyl-8-(3-amino-1-methylpyrazol-5-yl)xanthine, which is recrystallized from $CH_3OH$. A solution of 4-(benzyloxy)phenylacetic acid (0.196 mmol) in 3 mL of thionyl chloride is stirred at 70° C. for four hours, then excess thionyl chloride removed in a nitrogen stream.

A solution of 1,3-diallyl-8-(3-amino-1-methylpyrazol-5-yl)xanthine (0.151 mmol, Example 1) and 0.04 mL of anhydrous triethyl amine in 10 mL of $CH_2Cl_2$: $CH_3OH$ (1:1) is added and the mixture is stirred at room temperature for 24 hours, monitoring by TLC. At completion, the solvent is evaporated, the residue is dissolved in ethyl acetate, and the solution washed with saturated aqueous $NaHCO_3$ and brine. The organic layer is dried ($Na_2SO_4$), filtered, and evaporated in vacuo. The desired intermediate is purified by column chromatography on silica gel.

To a suspension of 10% Pd/C (5 mg) in $CH_3CH_2OH$ (10 mL) is added a solution of 1,3-diallyl-8-(3-(2-(4-(benzyloxy)phenyl)acetylamino-)-1-methylpyrazol-5-yl)xanthine in $CH_3CH_2OH$ (3 mL). The mixture is evacuated and charged with tritium gas to 50 psi, then shaken at room temperature for 16 hours. The mixture is evacuated, the solution filtered to remove catalyst, and the solution evaporated in vacuo. The residue is purified by column chromatography to provide the desired tritiated analogue, identical chromatographically to Example 7.

EXAMPLE 87

Preparation of Radioligand of Compound AS68

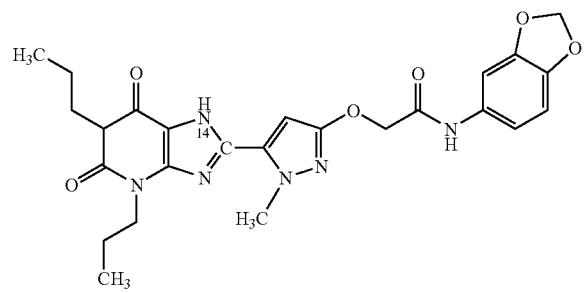

To a solution of ethyl (5-[$^{14}$C]-carboxy-1-methylpyrazol-3-yl)oxyacetate (0.5 mmol) and EDCI (0.5 mmol) in methanol (20 mL) is added a solution of 1,3-dipropyl-5,6-diaminouracil (0.5 mmol), dissolved in methanol (20 mL). The mixture is stirred at room temperature for two hours, the solvent is then removed in vacuo, water is added, and the solid that forms is collected by filtration and washed with additional cold water. The intermediate amide is heated in 20 mL of 2.5 N NaOH at 70° C. for 30 minutes to afford the desired 2-[5-(1,3-dipropyl-8-[$^{14}$C]-xanthin-8-yl)-1-methylpyrazol-3-yloxy]acetic acid.

Condensation of 2-[5-(1,3-dipropyl-[$^{14}$C]-8-[xanthin-8-yl]-1-methylpyrazol-3-yloxy]acetic acid (0.5 mmol) and 3,4-methylenedioxyaniline (1.3 mmol) in the presence of EDCI (1.12 mmol) and HOBt (1.14 mmol) in anhydrous dimethylformamide affords the desired [$^{14}$C]-labeled product, identical chromatographically with Example 39.

Preparation of Fluorescently Labeled Compounds

As with the radiolabelled compounds, the synthesis of fluorescently labeled compounds is relatively straightforward. Chemical bonding of fluorescent labels, with or without a linking or tethering group, to oligomeric compounds, is well known in the art (see for example: Hill, J. J. and Royer, C. A., Methods Enzymol., 1997, 278, 390-416; and Amann et al., Microbiol. Rev., 1997, 20, 191-200). Typically, the fluorescent label is attached via a covalent bond using a tethering moiety. Additional techniques and uses of fluorescently labeled compounds are disclosed in U.S. Pat. No. 6,127,124 to Leeds et al., incorporated herein by reference.

Utility

The compounds of the present invention can be used in vitro for scientific studies requiring highly selective $A_{2B}$ radioligands. For example, the present inventive 8-heteroaryl xanthine derivatives may be used to probe adenosine receptors in order to isolate or characterize the receptors.

Additionally, the compounds of the present invention can be used in vivo for treating diseases induced by activation of the adenosine $A_{2B}$ receptor and inflammatory diseases involving degranulation of mast cells including asthma, chronic obstructive pulmonary disease, rheumatoid arthritis, allergic rhinitis, allergic dermatitis and bee sting; impaired sensitivity to insulin including Type 2 diabetes or non-insulin dependent diabetes, pre-diabetic state, and impaired glucose tolerance; diseases in which angiogenesis is a key component of pathogenesis including solid tumors and angiogenic retinopathies; and apnea of preterm infants.

Furthermore, following the teachings of Belardinelli, the compounds of the present invention may be used for inhibiting cell proliferation in cells that express the $A_{2B}$ adenosine receptor including human retinal endothelial cells (HREC). Such uses include treatment for chronic and acute inflammatory diseases involving degranulation of mast cells including asthma, chronic obstructive pulmonary disease, rheumatoid arthritis, allergic rhinitis, allergic dermatitis and bee sting; impaired sensitivity to insulin including Type 2 diabetes or non-insulin dependent diabetes, pre-diabetic state, and impaired glucose tolerance; diseases in which angiogenesis is a key component of pathogenesis including solid tumors and angiogenic retinopathies; and apnea of preterm infants; myocardial reperfusion injury, inflammatory bowel disease, and autoimmune diseases such as rheumatoid arthritis, multiple sclerosis (MS) and lupus erythematosis.

Similarly, the compounds can be used in a method for the treatment of diseases involving microvascular abnormalities of the retina that are mediated by adenosine $A_{2B}$ receptors. Such diseases include, but are not limited to, retinopathy, prematurity, macular degeneration, and diabetic retinopathy.

The compounds of the present invention can be formulated as pharmaceutical compositions and administered to a mammalian host, such as a human patient in a variety of forms adapted to the chosen route of administration, i.e., orally or parenterally, by intravenous, intramuscular, topical, inhalation or subcutaneous routes. Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets or may be incorporated directly with the food of the patient's diet.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen or cherry flavoring may be added. When the unit dosage form is a capsule, it may contain, in addition to materials of the above type, a liquid carrier, such as a vegetable oil or a polyethylene glycol.

Various other materials may be present as coatings or to otherwise modify the physical form of the solid unit dosage form. For instance, tablets, pills or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor.

It is desirable that any material used in preparing any unit dosage form should be pharmaceutically acceptable and substantially non-toxic in the amounts employed. In addition, the active compound may be incorporated into sustained release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active compound of the present invention that is further adapted for the extemporaneous preparation of sterile injectable or infusible solutions or dispersions, optionally encapsulated in liposomes. In all cases, the ultimate dosage form is preferably sterile, fluid and stable under the conditions of manufacture and storage. The liquid carrier or vehicle can be a solvent or liquid dispersion medium such as, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and celatin.

Sterile injectable solutions are prepared by incorporating the active compound in the required amount of the appropriate solvent with various other ingredients enumerated above, as required, followed by filter sterilization. In the case of sterile powders for the preparation of sterile injectable solutions, the preferred methods of preparation are vacuum drying and freeze drying techniques, which yield a powder of the active compound plus any additional desired ingredient.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which, can be used to deliver the compounds of present invention to the skin are known in the art, for example, as described in U.S. Pat. Nos. 4,608,392, 4,992,478, 4,559,157 and 4,820,508.

Useful dosages of the compounds of the present invention can be determined by comparing their in vitro activity, and in vivo activity in animal models. Methods for the: extrapolation of effective dosages in mice, and other animals, to humans are known to the art; for example, see U.S. Pat. No. 4,938,949.

Generally, the concentration of the compound(s) of the present invention in a liquid composition, such as a lotion, will be from about 0.01-25 wt-%, preferably from about 0.1-10 wt-%. The concentration in a semi-solid or solid composition such as a gel or a powder will be about 0. 1-5 wt-%, preferably about 0.5-2.5 wt %.

The amount of the compound or an active salt or derivative required for use in treatment will vary not only with the particular salt selected but also with the route of administration, the nature of the condition being treated and the age and condition of the patient and will be ultimately at the discretion of the administering physician or clinician. In general, a suitable dose will be in the range of from about 0.001 mg/kg/day to about 20 mg/kg/day. For example, a dosage may be from 0.002 mg/kg/day to about 10 mg/kg of body weight per day, preferably in the range of 0.01 mg/kg/day to 1 mg/kg/day, and most preferably in the range of 0.1 mg/kg/day to 5 mg/kg/day.

The compound is conveniently administered in unit dosage form; for example, containing 5 to 1000 µg, conveniently 10 to 750 µg, most conveniently, 50 to 500 µg of active ingredient per unit dosage form.

The compounds of the invention can be administered by inhalation from an inhaler, insufflator, atomizer or pressurized pack or other means of delivering an aerosol spray. Pressurized packs may use a suitable propellant such as carbon dioxide or other suitable gas. In the case of a pressurized aerosol, the dosage unit may be determined by providing a value to deliver a metered amount. The inhalers, insufflators, and atomizers are fully described in pharmaceutical reference books such as Remington's Pharmaceutical Sciences 18th edition (1990) Mack Publishing Co., Easton, Pa.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye. Dosages above or below the range cited above are within the scope of the present invention and may be administered to the individual patient if desired and necessary.

When used in the treatment of treatment for ischemic injury to retinal vessels the compounds of the present invention are preferably formulated in eyedrops suitable for topical application.

Biological Assays

All synthesized compounds have been tested for their affinity to human A1, $A_{2A}$, $A_{2B}$ and $A_3$ adenosine receptors expressed in Chinese Hamster Ovary cells (CHO) ($A_1$, $A_{2A}$ and $A_3$) and HEK 293 cells ($A_{2B}$) using cell binding assay techniques known in the art.

The cells were grown adherently and maintained in Dulbecco's modified Eagle's medium with nutrient mixture F12 without nucleosides at 37° C. in 5% $CO_2$/95% air. The cells were washed with phosphate-buffered saline and scraped off flasks in ice cold hypotonic buffer (5 nM Tris HCl, 2 mM EDTA, pH 7.4). The cell suspension was homogenized with a Polytron and the homogenate was centrifuged for 30 minutes at 48,000 g. The resultant membrane pellet was re-suspended in 50 mM Tris HCl buffer at pH 7.4 for $A_1$ adenosine receptors; in 50 mM Tris HCl 10 mM MgCl, at pH 7.4 for $A_{2A}$ adenosine receptors; in 50 mM Tris HCl, 10 mM $MgCl_2$, 1 mM EDTA, at pH 7.4 for $A_3$ adenosine receptors and were utilized for binding assays.

HEK 293 cells transfected with the human recombinant $A_{2B}$ adenosine receptor were obtained from Receptor Biology, Inc. (Beltsville, Md. USA).

Binding of [$^3$H]-DPCPX to CHO cells transfected with the human recombinant $A_1$ adenosine receptor was performed according to the method previously described by Klotz et al. 1985. Displacement experiments were performed for 120 minutes at 25° C. in 200 µl of buffer containing 1 nM $^3$H]-DPCPX 20 µl of diluted membranes (50 µg of protein/assay) and at least 6 to 8 different concentrations of examined compounds. Non-specific binding was determined in the presence of 10 µM of CHA and this is always less than 10% of the total binding.

Binding of [$^3$H]ZM-241385 to CHO cells transfected with the human recombinant $A_{2A}$ adenosine receptors (50 µg of protein/assay) was performed according to Varani et al., 2000. In competition studies, at least 6-8 different concentrations of compounds were used and non-specific binding was determined in the presence of 1 µM ZM-241385 with an incubation time of 60 minutes at 25° C.

Binding of 1 [$^3$H]-DPCPX to HEK 293 cells transfected with the human recombinant $A_{2B}$ adenosine receptors was performed according to the method described by Varani et al., 2000. In particular, assays were carried out for 60 minutes at 25° C. in 100 µl of 50 nM Tris HCl buffer, 10 nM $MgCl_2$, 1 mM EDTA, 0.1 mM benzamidine pH 7.4, 2 IU/ml adenosine deaminase containing 40 nM [$^3$H]-DPCPX, diluted membranes (20 µg of protein/assay) and at least 6-8 different concentration of tested compounds. Non-specific binding was determined in the presence of 100 µM of NECA and was always less than 30% of the total binding.

Binding of [$^3$H]-MRE3008-F20 to CHO cells transfected with the human recombinant $A_3$ adenosine receptors was performed according to Varani et al., 2000. Competition experiments were carried out in duplicate in a final volume of 250 µl in test tubes containing 1 nM [$^3$H]-MRE3008-F20, 50 mM Tris HCl buffer, 10 nM $MgCl_2$, pH 7.4 and 100 µl of diluted membranes (50 µg of protein/assay) and at least 6-8 different concentrations of examined ligands for 120 minutes at 4° C. Non-specific binding was defined as binding in the presence of 1 µM [$^3$H]-MRE3008-F20 and was about 25% of total binding.

Bound and free radioactivity portions were separated by filtering the assay mixture through Whatman GF/B glass-fiber filters using a Micro-Mate 196 cell harvester (Packard Instrument Company). The filter bound radioactivity was counted on Top Count (efficiency 57%) with Micro-Scint 20. The protein concentration was determined according to a Bio-Rad method (Bradford, 1976) with bovine albumin as reference standard.

Measurement of cyclic AMP (CAMP) levels in CHO cells transfected with human $A_{2B}$ adenosine receptors was performed in the following manner. CHO cells transfected with human $A_2B$ adenosine receptors were washed with phosphate-buffered saline, diluted tripsine and centrifuged for 10 minutes at 200 g. The pellet containing the CHO cells (1.times.10$^6$ cells/assay) was suspended in 0.5 ml of incubation mixture (mM): 15 mM NaCl, 0.27 mM KCl, 0.037 mM $NaH_2PO_4$, 0.1 mM $MgSO_4$, 0.1 $CaCl_2$, 0.01 mM Hepes, 1 mM MgCl, 0.5 mM glucose, pH 7.4 at 37° C., 2 IU/ml adenosine deaminase and 4-(3-butoxy-4methoxybenzyl)-2-imidazolidinone (Ro 20-1724) as phosphodiesterase inhibitor and preincubated for 10 minutes in a shaking bath at 37° C.

The potencies of antagonists studied were determined by antagonism of NECA (100 nM)-induced stimulation of cAMP levels. The reaction was terminated by the addition of cold 6% thrichloroacetic acid (TCA). The TCA suspension was centrifuged at 2000 g for 10 minutes at 4° C. and the supernatant was extracted four times with water saturated diethyl ether. The final aqueous, solution was tested for cAMP levels by a competition protein binding assay. Samples of cAMP standard (0-10 pmoles) were added to each test tube containing the incubation buffer (trizma base 0.1 M, aminophylline 8.0 mM, 2-mercaptoethanol 6.0 mM, pH 7.4) and [H$^3$]-cAMP in a total volume of 0.5 ml. The binding protein previously prepared from beef adrenals, was added to the samples previously incubated at 4° C. for 150 minutes, and after the addition of charcoal were centrifuged at 2000 g for 10 minutes. The clear supernatant was counted in a Beckman scintillation counter.

Data Analysis

The filter bound radioactivity was counted on a Top Count brand Microplate Scintillation Counter (efficiency 57%)

with Micro-Scint 20. The protein concentration was determined according to a Bio-Rad method (Bradford. 1976) with bovine albumin as a standard reference. Inhibitory binding constant $K_i$ values were calculated from those of $IC_{50}$ according to the Cheng and Prusoff equation (Cheng and Prusoff, 1973):

$$K_i = IC_{50}/(1+[C^*]/K_D^*),$$

where [C*] is the concentration of the radioligand and $K_D^*$ is its dissociation constant. The weighted non-linear least-squares curve fitting program LIGAND (Munson & Rodboard, 1980) was used for computer analysis of saturation and inhibition experiments. All data ($K_i$ and $IC_{50}$) are expressed as geometric means with 95% confidence intervals.

Results and Discussion

Binding results, expressed as $K_i$ for the synthesized compounds AS3 to AS69 are reported in Table 1. A binding of greater than 1,000 nM (1.0 µM) is indicated when no appreciable binding was measured. As is seen in Table 1, the compounds of the present invention present a wide range of binding affinities hence making selection of antagonism for various adenosine receptor subtypes possible. For example, a compound such as AS68 is a highly potent $A_{2B}$ antagonist and retains significant $A_1$ antagonism. Compounds such as AS28 provide less $A_{2B}$ affinity but are totally selective with no appreciable binding to the other adenosine receptor subtypes.

The Compound AS68 has the highest measured affinity for the human $A_{2B}$ receptors ($K_1$=5.5 nM), binding to adenosine $A_1$ receptors ($K_i$=200 nM) but appears to show little or no affinity to human $A^{2A}$ and $A_3$ adenosine receptors subtypes. The compounds AS29, AS39, AS57, AS64 and AS65 have good affinity for the human $A_{2B}$ receptors with an affinity value in the nanomolar range ($K_i$=9-20 nM). Other compounds such as AS11, AS27, AS28, AS35 and AS54 showed a $K_i$ value in the nanomolar range ($K_i$=28-39 nM) for $A_{2B}$ receptors. Compounds AS13, AS15, AS16 and AS17 show affinity in nanomolar range ($K_i$=56-103 nM) to the human $A_{2B}$ receptor, with no appreciable affinity for the other adenosine receptor subtypes.

TABLE 1

Binding Affinites to Adenosine Receptors

| | Ki (nM) | | | |
|---|---|---|---|---|
| Compound Number | [³H]DPCPX binding to human $A_1$ receptors expressed in CHO cells | [³H]ZM241385 binding to human $A_{2A}$ receptors expensed in CHO cells | [³H]DPCPX binding to human $A_{2B}$ receptors expressed in HEK293 cells | [³H]MRE3008F20 binding to human $A_3$ receptors expressed in CHO cells |
| AS3 | 201(172-236) | >1000 | 235(209-264) | >1000 |
| AS11 | 900(811-996) | >1000 | 35(27-45) | >1000 |
| AS12 | >1000 | >1000 | >1000 | >1000 |
| AS13 | >1000 | >1000 | 96(80-114) | >1000 |
| AS14 | >1000 | >1000 | >1000 | >1000 |
| AS15 | >1000 | >1000 | 78(63-96) | >1000 |
| AS16 | >1000 | >1000 | 56(42-77) | >1000 |
| AS17 | >1000 | >1000 | 103(79-136) | >1000 |
| AS18 | >1000 | >1000 | >1000 | >1000 |
| AS19 | >1000 | >1000 | >1000 | >1000 |
| AS21 | >1000 | >1000 | >1000 | >1000 |
| AS22 | 200(166-240) | >1000 | 88(84-92) | >1000 |
| AS23 | 850(762-946) | >1000 | 100(83-120) | >1000 |
| AS24 | 4481(3650-5501) | >1000 | 160(142-179) | >1000 |
| AS25 | 3227(2799-3720) | >1000 | 50(41-60) | >1000 |
| AS26 | >1000 | >1000 | 1628(1374-1930) | >1000 |
| AS27 | 520(484-558) | >1000 | 28(23-33) | >1000 |
| AS28 | >1000 | >1000 | 38(33-43) | >1000 |
| AS29 | 56(47-67) | >1000 | 13(11-16) | >1000 |
| AS30 | 100(83-120) | >1000 | 90(73-110) | >1000 |
| AS31 | 163(137-193) | >1000 | 111(100-124) | >1000 |
| AS32 | 746(659-843) | >1000 | 190(172-209) | >1000 |
| AS43 | 1898(1723-2091) | >1000 | 130(113-150) | >1000 |
| AS44 | >1000 | >1000 | >1000 | >1000 |
| AS56 | 1793(1460-2201) | 2433(1675-3533) | 100(83-120) | >1000 |
| AS57 | 566(516-621) | 1249(856-1822) | 18(12-27) | >1000 |
| AS58 | >1000 | 1755(1343-2292) | 342(274-426) | >1000 |
| AS8 | >1000 | >1000 | >1000 | >1000 |
| AS9 | >1000 | >1000 | >1000 | >1000 |
| AS10 | 548(464-648) | >1000 | 2065(1866-2284) | >1000 |
| AS38 | >1000 | >1000 | 175(134-229) | >1000 |
| AS40 | >1000 | >1000 | 569(506-640) | >1000 |
| AS7 | 122(84-177) | >1000 | 342(274-426) | >1000 |
| AS36 | >1000 | >1000 | >1000 | >1000 |
| AS33 | >1000 | >1000 | >1000 | >1000 |
| AS59 | >1000 | >1000 | 1012(819-1250) | >1000 |
| AS64 | 65(48-86) | >1000 | 12(7-21) | >1000 |
| AS65 | 150(132-170) | >1000 | 20(16-25) | >1000 |
| AS68 | 200(180-226) | >1000 | 5.5(4.6-6.5) | >1000 |
| AS69 | >1000 | >1000 | 86(77-96) | >1000 |
| AS66 | 467(400-546) | >1000 | 303(260-352) | >1000 |

TABLE 1-continued

Binding Affinites to Adenosine Receptors

Ki (nM)

| Compound Number | [$^3$H]DPCPX binding to human $A_1$ receptors expressed in CHO cells | [$^3$H]ZM241385 binding to human $A_{2A}$ receptors expensed in CHO cells | [$^3$H]DPCPX binding to human $A_{2B}$ receptors expressed in HEK293 cells | [$^3$H]MRE3008F20 binding to human $A_3$ receptors expressed in CHO cells |
|---|---|---|---|---|
| AS67 | 2427(2067-2850) | >1000 | 132(98-178) | >1000 |
| AS37 | 140(123-159) | >1000 | 58(45-74) | >1000 |
| AS35 | 55(46-65) | >1000 | 34(26-46) | >1000 |
| AS60 | 168(140-201) | >1000 | 93(82-105) | >1000 |
| AS61 | 181(127-258) | >1000 | 185(163-210) | >1000 |
| AS62 | 72(45-114) | >1000 | 207(162-265) | >1000 |
| AS63 | 49(34-72) | >1000 | 66(38-116) | >1000 |
| AS4 | >1000 | >1000 | >1000 | >1000 |
| AS20 | >1000 | >1000 | >1000 | >1000 |
| AS53 | 2410(1760-3301) | >1000 | 59(44-81) | >1000 |
| AS54 | 448(365-550) | >1000 | 39(33-46) | >1000 |
| AS55 | 1993(1658-2397) | >1000 | 90(73-110) | >1000 |
| AS1 | >1000 | >1000 | >1000 | >1000 |
| AS49 | 1440(1250-2211) | >1000 | 81(70-110) | >1000 |
| AS91 | 1005(916-1103) | >1000 | 74(67-81) | >1000 |
| AS92 | 79(72-86) | >1000 | 19(12-29) | >1000 |
| AS93 | >1000 | >1000 | 86(78-93) | >1000 |
| AS95 | >1000 | >1000 | 36(27-47) | >1000 |
| AS99 | 700(650-760) | >1000 | 10(8-13) | >1000 |
| AS100 | 300(240-380) | >1000 | 16(12-20) | >1000 |
| AS101 | >1000 | >1000 | 12(8-17) | >1000 |
| AS89 | 955(896-1017) | >1000 | 41(35-48) | >1000 |
| AS70 | 250(181-348) | >1000 | 15(10-21) | >1000 |
| AS72 | >1000 | >1000 | 55(46-65) | >1000 |
| AS87 | >1000 | >1000 | 122(108-136) | >1000 |
| AS90 | 810(763-859) | >1000 | 85(66-95) | >1000 |
| AS96 | >1000 | >1000 | 24(18-32) | >1000 |
| AS74 | >1000 | >1000 | 47(43-52) | >1000 |
| AS76 | >1000 | >1000 | 51(44-58) | >1000 |
| AS73 | >1000 | >1000 | 70(61-80) | >1000 |
| AS75 | >1000 | >1000 | 53(40-69) | >1000 |
| AS81 | >1000 | >1000 | 108(75-155) | >1000 |
| AS85 | >1000 | >1000 | >1000 | >1000 |
| AS94 | >1000 | >1000 | 32(22-45) | >1000 |
| AS103 | 81 | 606 | 4.9 | 116 |

For use as a pharmaceutical preparation, Compound AS68 is particularly preferred due to its excellent affinity towards the $A_{2B}$ receptor ($K_i$=5.5 nM) despite some significant $A_1$ adenosine receptor binding ($K_i$=200 nM). Due to strong cardiovascular effects compounds with significant $A_{2A}$ binding are less preferred.

For use as a radioligand and where near total $A_{2B}$ receptor selectivity is desired compounds such as AS13, AS15, AS16, AS17, AS28 and AS69 are preferred. All have relatively strong $A_{2B}$ receptor binding ($K_i$=38-103 nM) but without significant binding for any of the other receptor subtypes.

FIGS. 1 through 4 show typical competition curves of compounds AS29, AS57, AS64 and AS68 at $A_1$, $A_{2A}$, $A_{2B}$, and $A_3$ $A_{2B}$ and $A_3$ adenosine receptors.

Finally, to evaluate the regulation of adenylyl cyclase activity and to test whether the binding parameters correlated with the functional response, the $IC_{50}$ values were obtained for inhibition of cAMP production by antagonists. In particular, we evaluated the capability of the several compounds to inhibit NECA (100 nM)-stimulated cyclic AMP accumulation.

Table 2 summarizes the $K_i$ values obtained in [$^3$H]-DPCPX binding to $A_{2B}$ adenosine receptors and the $IC_{50}$ values for the inhibition of cAMP levels. Of the selected compounds, the most potent adenosine $A_{2B}$ receptor antagonists were AS64 and AS68 ($IC_{50}$=38 and 88 nM, respectively). Compounds AS29 and AS57 show an $IC_{50}$ value of 93 and 95 nM, respectively (see also FIG. 7). Other tested compounds show an $IC_{50}$ value in the lower nanomolar range ($IC_{50}$=100-152 nM).

TABLE 2

Comparison of [$^3$H]-DPCPX Binding to cAMP Levels

| | [$^3$H]-DPCPX binding to human $A_{2B}$ receptors in HEK 293 cells Ki (nM) | Cyclic AMP assay-human $A_{2b}$ receptors in CHO cells $IC_{50}$ (nM) |
|---|---|---|
| AS 11 | 35(27-45) | 103(92-115) |
| AS 27 | 28(23-33) | 128(114-144) |
| AS 28 | 38(33-43) | 120(103-140) |
| AS 29 | 13(11-16) | 93(84-102) |
| AS 35 | 34(26-46) | 152(136-170) |
| AS 54 | 39(33-46) | 136(115-161) |
| AS 57 | 28(12-27) | 95(90-101) |
| AS 64 | 12(7-21) | 88(82-95) |
| AS 65 | 20(16-25) | 108(91-129) |
| AS 68 | 5.5(4.6-6.5) | 38(29-51) |

Each value of Table 2 is the geometric mean (with 95% confidence limits in parentheses) of at least three separate experiments performed in duplicate.

Figure 5:
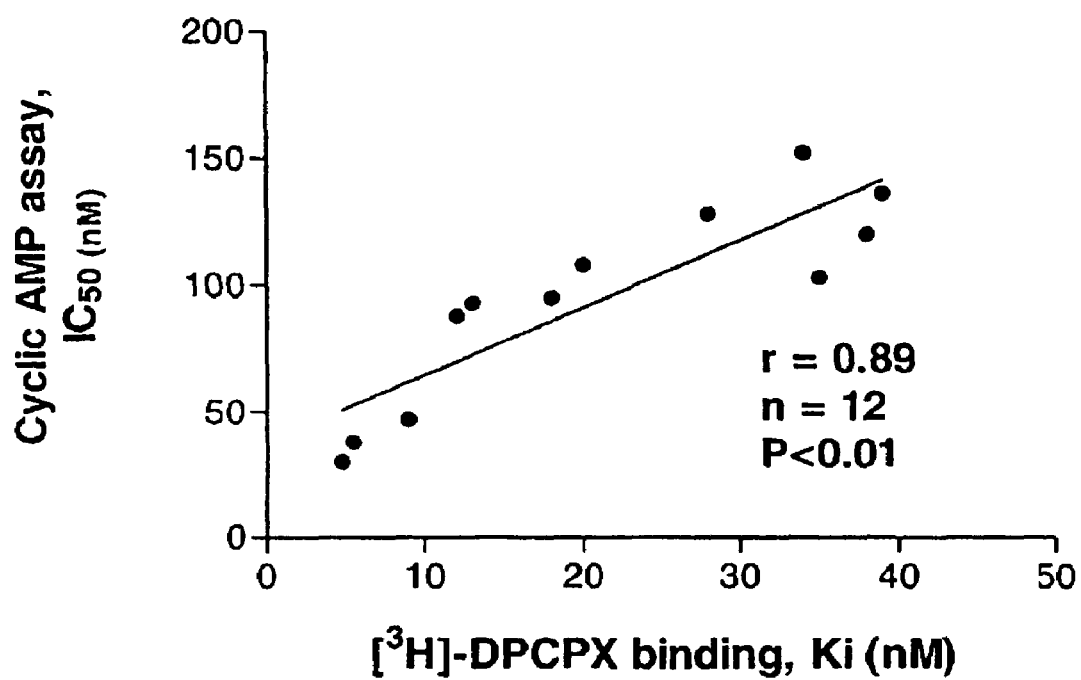
FIG. 5 illustrates a Comparison between binding and functional data.

The Spearman's rank correlation coefficient between affinity values of [$^3$H]-DPCPX binding to $A_{2B}$ adenosine receptor by selected compounds and the $IC_{50}$ values in the cAMP assay was 0.89 (P<0.01). A comparison of the $K_i$ and $IC_{50}$ values indicated that high correlation exists between data obtained from binding and cAMP assays (FIG. 5).

Formulations

Formulations of the present invention for medical use comprise an active compound, i.e., a compound of formula (IA) or (IB) together with an acceptable carrier thereof and optionally other therapeutically active ingredients. The carrier must be pharmaceutically acceptable in the sense of being compatible with the other ingredients of the formulation and not deleterious to the recipient thereof.

The present invention, therefore, further provides a pharmaceutical formulation comprising a compound of formula (IA) or (IB) together with a pharmaceutically acceptable carrier thereof.

The formulations include, but are not limited to, those suitable for oral, rectal, topical or parenteral (including subcutaneous, intramuscular and intravenous) administration. Preferred are those suitable for oral, parenteral or topical administration.

The formulations may conveniently be presented in unit dosage form and may be prepared by any of the methods well known in the art of pharmacy. All methods include the step of bringing the active compound into association with a carrier that constitutes one or more accessory ingredients. In general, the formulations are prepared by uniformly and intimately bringing the active compound into association with a liquid carrier or a finely divided solid carrier and then, if necessary, shaping the product into desired unit dosage form.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients) may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Formulations suitable for parenteral administration conveniently comprise sterile aqueous preparation of the active compound that is preferably isotonic with the blood of the recipient. Thus, such formulations may conveniently contain distilled water, 5% dextrose in distilled water or saline. Useful formulations also comprise concentrated solutions or solids containing the compound of formula (I) that upon dilution with an appropriate solvent give a solution suitable for parental administration above.

Topical formulations include ointments, creams, gels and lotions that may be prepared by conventional methods known in the art of pharmacy. In addition to the ointment, cream gel, or lotion base and the active ingredient, such topical formulation may also contain preservatives, perfumes, and additional active pharmaceutical agents.

Solutions for use as eyedrops are preferentially prepared by first aseptically mixing of all the necessary ingredients i.e. the active substance, salts and lubricant. If necessary the pH is adjusted to 5-7 using solutions of NaOH, KOH, HCl or boric acid. The solution is then sterilized by autoclaving or sterile filtration and filled on one dose packages.

Solutions can also be prepared by first preparing solutions of each of the ingredients and then sterilizing these solutions in the same manner as above before finally mixing and filling the solutions on one dose packages under aseptic conditions.

In addition to the aforementioned ingredients, the formulations of this invention may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

EXAMPLES-PHARMACEUTICAL FORMULATIONS

| (A) Transdermal System - for 1000 patches | |
|---|---|
| Ingredients | Amount |
| Active compound | 100 g |
| Silicone fluid | 450 g |
| Colloidal silicon dioxide | 2 g |

The silicone fluid and active compound are mixed together and the colloidal silicone dioxide is added to increase viscosity. The material is then dosed into a subsequent heat sealed polymeric laminate comprised of the following: polyester release liner, skin contact adhesive composed of silicone or acrylic polymers, a control membrane which is a polyolefin, and an impermeable backing membrane made of a polyester multi-laminate material. The resulting laminated sheet is than cut into 10 sq. cm patches

| (B) Oral Tablet - For 1000 Tablets | |
|---|---|
| Ingredients | Amount |
| Active compound | 50 g |
| Starch | 50 g |
| Magnesium Stearate | 5 g |

The active compound and the starch are granulated with water and dried. Magnesium stearate is added to the dried granules and the mixture is thoroughly blended. The blended mixture is compressed into tablets.

| (C) Injection - for 1000, 1 mL Ampules | |
|---|---|
| Ingredients | Amount |
| Active compound | 10 g |
| Buffering Agents | q.s. |
| Propylene glycol | 400 mg |
| Water for injection | q.s. |
| | 1000 mL |

The active compound and buffering agents are dissolved in the propylene glycol at about 50° C. The water for injection is then added with stirring and the resulting solution is filtered, filled into ampules, sealed and sterilized by autoclaving.

| (D) Continuous Injection - for 1000 mL | |
|---|---|
| Ingredients | Amount |
| Active compound | 10 g |
| Buffering agents | q.s. |
| Water for injection | q.s. |
| | 1000 mL |

| (E) Eye Drops - for 100 mL | |
|---|---|
| Ingredients | Amount |
| Active compound | 0.01-1.0 g |
| Sodium chloride | 0.5-0.09 g |
| Carbachol chloride | 0.01-1.0 g |
| Boric acid | 1.15-3.0 g |
| Water for injection | q.s. 100 mL |

The eyedrops according to the formulations suggested can be applied directly to the eye either upon need or 3-4 times daily.

An aerosol propellant suitable for use in an inhaler can be prepared similar to that described in U.S. Pat. No. 6,509,005 to Peart et al., which is incorporated by reference.

| (F) Aerosol propellant | |
|---|---|
| Ingredients | Amount |
| Active compound | 0.13% |
| Ethanol | ~5% |
| Hydrofluoroalkane propellant | 95% |

Those skilled in the art will recognize, or be able to ascertain using no more than routine experimentation, many equivalents, modifications and variations to the specific embodiments of the invention described herein. For example, other excipients may be utilized in preparing the pharmaceutical formulations. In addition, some of the compounds described herein contain one or more asymmetric centers and may therefore give rise to enantiomers and diastereomers as well as their racemic and resolved, enantiomerically pure or diastereomerically pure forms, and pharmaceutically acceptable salts thereof. Moreover, it will be appreciated that the general representation of such paired variables as $R^3$ and $R^4$, in compounds of formula (I), is not to be construed as to represent a particular orientation of the paired members. Accordingly, it is not intended that the present invention be limited to the specifics of the foregoing description of the preferred embodiments and example compounds, but rather as being limited only by the scope of the invention as defined in the claims appended hereto, including enantiomeric, diastereomeric and pharmaceutical salt forms.

REFERENCES

Baraldi P G, Cacciari B, Spalluto G, Pineda de las Infantas y Villatoro M J, Zocchi C, Dionisotti S. Ongini E. (1996). Pyrazolo[4,3-e]-1,2,4-triazolo[1,5-c]-pyrimidine derivatives: potent and selective $A_{2A}$ adenosine antagonists. J Med Chem. 39: 1164-1171.

Baraldi P G, Cacciarl B, Spalluto G, Bergonzoni M, Dionisotti S, Ongini E, Varani K, Borea P A. (1998). Design, synthesis and biological evaluation of a second generation of pyrazolo[4,3-e]1,2,4-triazolo[1,5-c]-pyrimidines as potent and selective $A_{2A}$ adenosine receptor antagonists. J Med Chem 41: 2126-2133.

Baraldi P G, Cacciari B, Romagnoli R, Spalluto G, Klotz K-N, Leung E, Varani K, Gessi S, Merighl S, Borea P A. (1999). Pyrazolo[4,3-e]1,2,4-triazolo[1,5c]pyrimidine derivatives as highly potent and selective human A3 adenosme receptor antagonists. J Med Chem 42: 4473-4478.

Baraldi P G, Cacciari B, Romagnoli R, Merighi S, Varani K, Borea P A, Spalluto G. (2000). A3 Adenosine receptor ligands; history and perspectives. Med Res Rev 20: 103-128.

Baraldi P G, Cacciari B, Romagnoli R, Klotz, K-N, Spalluto G., Varani K, Gessi S., Merighl S, Borea P A (2001). Pyrazolo[4,3-e]1,2,4-triazolo[1,5-c]pyrimidine derivatives as adenosine receptor ligands: a search for A213 adenosine receptor. Drug Dev Res., 53, 225-235.

Boyle D L, Sajjadi F G, Firestein G S. (1996). Inhibition of synoviocyte collagenase gene expression by adenosine receptor stimulation. Arthritis Rheum 39: 923-930.

Bradford M M. (1976). A rapid and sensitive method for the quantification of microgram quantities of protein utilizing the principle of protein dye-binding. Anal Biochem 72: 248-254.

Cheng Y. C., Prusoff W. H. (1973). Relationships between the inhibition constant ($K_i$) and the concentration of inhibitor which causes 50 per cent inhibition ($IC_50$) of an enzymatic reaction. Biochem. Pharmacol., 22: 3099-3 108.

Daly J W, Butts-Lamb P, Padgett W. (1983). Subclasses of adenosine receptors in the central nervous system: interaction with caffeine and related methylxanthines. Cell Mol Neurobiol 3: 69-80.

De Zwart M, Vellinga R C, Beukers. M W, Sleegers D F, von Frijtag Drabbe Kunzel J K, de Groote M, Ijzerman A P. (1999). Potent antagonist for the human adenosine $A_{2B}$ receptor. Derivatives of the triazolotriazine adenosine receptor antagonist ZM241385 with high affinity, Drug Dev Res 48: 95-103.

Dubey R K, Gillasple D G, Osaka K, Suzuki F, Jackson E K. (1996). Adenosine inhibits growth of rat aortic smooth muscle cells: possible role of $A_{2B}$ receptors. Hypertension 27:786-793.

Feoktistov I, Biaggioni I. 1995. Adenosine $A_{2B}$ receptors evoke interleukin-S secretion in human mast cells: an enprofylline-sensitive mechanism with implication for asthma. J. Clin Invest 96: 1979-1986.

Feoktistov I, Bilaggioni I. (1997). Adenosine $A_{2B}$ receptors. Pharmacol Rev49: 381-402.

Feoktistov I, Bilaggioni I. (1998). Pharmacological characterization of adenosine $A_{2B}$ receptors. Biochem Pharmacol 55: 627-633.

Feoktistov I, Wells J, Biaggioni I. (1998), Adenosine $A_{2B}$ receptors as therapeutic targets. Drug Dev. Res 45: 198-206.

Haynes J J, Obikao B, Thompson V,"J, Downey J. (1995). Adenosine-induced vasodilation receptor characterization in pulmonary circulation. Am J Physiol 26S: H1862-H1868.

Jacobson K A, Ijzerman A P, Linden J. (1999). 1,3,-Dialkylxanthine derivatives having high potency as antagonists at human $A_{2B}$ adenosine receptors. Drug. Dev. Res 47: 45-53.

Ji X-D. Jacobson K A. (1999). Use of triazolotriazine [3H]-ZM241385 as a radioligand at recombinant human $A_{2B}$ adenosine receptors. Drug Des Discov 16: 217-226.

Ji X-D. Kim Y-C, Ahem D. G., Linden J., Jacobson K A. (2001). [3H]-MRS-1754, a selective antagonist radioligand for $A_{2B}$ adenosine receptors. Biochem Pharmacol, 61: 657-663.

Kim Y-C. de Zwart M., Chang L, Moro S, von Frijtag Drabbe Kunzel J K, de Groote M, Melman N, Ijzerman A P, Jacobson K A. (1998). Derivatives of the triazoloquinazoline adenosine antagonist (CGS 15943) having high potency at the human $A_{2B}$ and A3 receptor subtypes. J Med Chem 41: 2835-2845.

Kim Y-C, Karton Y, Ji X-D, Melman N, Linden J, Jacobson K A. (1999). Acyl-hydrazide derivatives of a xanthine carboxylic congener (XCC) as selective antagonists at human $A_{2B}$ adenosine receptors. Drug Dev Res 47: 178-188.

Kim Y-C, Ji X-D, Melman N. Linden J, Jacobson K A. (2000). Aniide derivatives of an 8-phenylxanthine carboxylic congener are highly potent and selective antagonists at human $A_{2B}$ adenosine receptors. J Med Chem 43: 1165-1172.

Klotz K N, Hessling J, Hegler J, Owman C, Kull B, Fredholm B B, Lohse M J. (1998). Comparative pharmacology of human adenosine receptor subtypes characterization of stably transfected receptors in CHO cells. Naunyn-Schmied. Arch Pharm. 357:1-9.

Londos C, Cooper D M F, Wolff J. (1980). Subclasses of external adenosine receptors. Proc Natl Acad Sci USA 77: 2551-2554.

Marquardt D L, Walker L L, Heinemann S. (1994). Cloning of two adenosine receptor subtypes from mouse bone marrow derived mast cells. J Immunol 152: 4508-4515.

Mateo J, Castro E, Zwiller J, Aunis D, Miras-Portugal M T. (1995). 5-(N-ethylcarboxamido)-adenosine inhibits Ca2+, influx and activares a protein phosphatase in bovine adrenal chromaffin cells. J Neurochem 64: 77-84.

Murthy K S, McHenry L, Grider J R, Makhlouf G M. (1995). Adenosine $A_1$, and $A_{2B}$ receptors coupled to distinct interactive signaling pathways in intestinal muscle cells. J Pharmacol Exp Ther 274: 243-2-46.

Munson P J, Rodbard D. (1980). Ligand: a versatile computerized approach for the characterization of ligand binding systems. Anal. Biochem., 107: 220-239.

Varani K, Gessi S, Dionisotti S, Ongini E, Borea P A. (1998). [3H]-SCH58261 labelling of functional $A_{2A}$ adenosine receptors in human neutrophil membranes. Br. J. Pharmacol., 123: 1723-1731.

Varani K, Merighi S, Gessi S, Klotz K-N, Leung E, Baraldi P G, Cacciari B, Romagnoli R, Spallato P, Borea P A. (2000). [3H]-MRE3008F20: a novel antagonist radioligand for the pharmacological and biochemical characterization of human A3 adenosine receptors. Mol. Pharmacol., 57: 968-975.

Zocchi C, Ongini E, Ferrara S, Baraldi P G, Dionisotti S. (1996). Binding of the radioligand [3H]-SCH58261, a new non-xanthine $A_{2A}$ adenosine receptor antagonist, to rat striatal membranes. Br J Pharmacol. 117: 1381-1386.

What is claimed is:

1. A method of treating asthma, which method comprises administering to a patient in need of treatment thereof an effective amount of a compound of formula (I):

(I)

wherein
$R^1$ and $R^2$ are independently hydrogen, ($C_1$ to $C_8$)alkyl, ($C_2$ to $C_8$)alkenyl, ($C_2$ to $C_8$)alkynyl, ($C_7$ to $C_{14}$)aralkyl, ($C_8$ to $C_{14}$)aralkenyl, or ($C_8$ to $C_{14}$)aralkynyl;

$R^3$ is hydrogen, ($C_1$ to $C_4$)alkyl, ($C_2$ to $C_5$)alkenyl, or ($C_2$ to $C_5$)alkynyl;

A is a carbon-carbon bond, alkyl chain of one to four carbons, alkenyl chain of two to four carbons, or alkynyl chain of two to four carbons;

X is an optionally substituted five or six-membered heteroaromatic ring, containing one to four heteroatoms, selected from nitrogen, oxygen, or sulfur, provided that at least one heteroatom is nitrogen;

M is a ($C_1$ to $C_8$)alkylene, ($C_2$ to $C_8$)alkenylene, or ($C_2$ to $C_8$)alkynylene, wherein at least one of the carbon atoms of the alkylene, alkenylene, or alkynylene group is present as a carbonyl, and one or more of the remaining carbon atoms of the alkylene, alkenylene, or alkynylene group may be replaced by —O—, —N($R^7$)—, —S—, —S(O)—, or —S(O)$_2$—;

$G^1$ and $G^2$ are independently CH or N;

$R^4$, $R^5$ and $R^6$ are independently hydrogen, ($C_1$ to $C_4$)alkyl, ($C_2$ to $C_5$)alkenyl, ($C_2$ to $C_5$)alkynyl, optionally substituted ($C_6$ to $C_{10}$)aryl, ($C_7$ to $C_{14}$)aralkyl, ($C_8$ to $C_{14}$)aralkenyl, or ($C_8$ to $C_{14}$)aralkynyl, acyl, optionally substituted alkoxy, aralkoxyalkylthio, amino, substituted amino, disubstituted amino, fluoro, chloro, bromo, iodo, nitro, cyano, azido, hydroxy, sulflhydryl, S(O)alkyl, S(O)$_2$alkyl, CO$_2$H, SO$_3$H; or taken together with the carbon atoms to which they are attached either $R^4$ and $R^5$ or $R^5$ and $R^6$ form a five or six-membered heterocyclic or heteroaromatic ring containing one to four hetereoatoms selected from nitrogen, oxygen, or sulfur; or taken together with the carbon atoms to which they are attached either $R^4$ and $R^5$ or $R^5$ and $R^6$ form a carbocyclic or heterocyclic fused ring selected from the group of fused rings comprising —OCH$_2$O—, —OCH($R^7$)O—, —OC($R^7$)$_2$O—, —OCH$_2$CH$_2$O—, —OCH$_2$CH$_2$—, —CH$_2$CH$_2$O—, —OCH$_2$CH$_2$CH$_2$—, —CH$_2$CH$_2$CH$_2$O—, —OCH=CH—, —CH=CH—O—, —O—CH=CH—O—, —CH=CH—CH=CH—, —CH$_2$CH$_2$CH$_2$— and —CH$_2$CH$_2$CH$_2$CH$_2$—;

R$^7$ is hydrogen, (C$_1$ to C$_4$)alkyl, (C$_2$ to C$_5$)alkenyl, or (C$_2$ to C$_5$)alkynyl;

or a pharmaceutically acceptable salt thereof.

2. A method of treating asthma, which method comprises administering to a patient in need of treatment thereof an effective amount of a compound selected from the group consisting of:

8-(3-amino-1-methyl-1H-pyrazol-5-yl)-1,3-dipropyl-3,7-dihydro-1H-purine-2,6-dione;

[3-(2,6-dioxo-1,3-dipropyl-2,3,6,7-tetrahydro-1H-purin-8-yl)isoxazol-5-yl]methyl-benzoate;

8-(1-methyl-4-nitro-1H-pyrrol-2-yl)-1,3-dipropyl-3,7-dihydro-1H-purine-2,6-dione;

4-{[5-(1,3-dipropyl-2,6-dioxo-2,3,6,7-tetrahydro-1H-purin-8-yl)-1-methyl-1H-pyrazol-3-yl]amino}-4-oxobutanoic acid;

tert-butyl 4-{[5-(2,6-dioxo-1,3-dipropyl-2,3,6,7-tetrahydro-1H-purin-8-yl)-1-methyl-1H-pyrazol-3-yl]amino}-4-oxobutylcarbamate;

4-{[5-(2,6-dioxo-1,3-dipropyl-2,3,6,7-tetrahydro-1H-purin-8-yl)-1-methyl-1H-pyrazol-3-yl]amino}-4-oxobutan-1-aminium chloride;

N-[5-(2,6-dioxo-1,3-dipropyl-2,3,6,9-tetrahydro-1H-purin-8-yl)-1-methyl-1H-pyrazol-3-yl]-2-phenylacetamide;

2-(2,4-dichlorophenoxy)-N-[5-(2,6-dioxo-1,3-dipropyl-2,3,6,7-tetrahydro-1H-purin-8-yl)-1-methyl-1H-pyrazol-3-yl]acetamide;

2-(3-methoxyphenyl)-N-[5-(2,6-dioxo-1,3-dipropyl-2,3,6,9-tetrahydro-1H-purin-8-yl)-1-methyl-1H-pyrazol-3-yl]acetamide;

N-[5-(2,6-dioxo-1,3-dipropyl-2,3,6,9-tetrahydro-1H-purin-8-yl)-1-methyl-1H-pyrazol-3-yl]-2-(4-isobutylphenyl)acetamide;

N-[5-(2,6-dioxo-1,3-dipropyl-2,3,6,9-tetrahydro-1H-purin-8-yl)-1-methyl-1H-pyrazol-3-yl]-2-(4-nitrophenyl)acetamide;

2-[4-benzyloxyphenyl]-N-[5-(2,6-dioxo-1,3-dipropyl-2,3,6,9-tetrahydro-1H-purin-8-yl)-1-methyl-1H-pyrazol-3-yl]acetamide;

2-[4-hydroxyphenyl]-N-[5-(2,6-dioxo-1,3-dipropyl-2,3,6,9-tetrahydro-1H-purin-8-yl)-1-methyl-1H-pyrazol-3-yl]acetamide;

(2S)-N-[5-(2,6-dioxo-1,3-dipropyl-2,3,6,7-tetrahydro-1H-purin-8-yl)-1-methyl-1H-pyrazol-3-yl]-2-phenylpropanamide;

(2R)-N-[5-(2,6-dioxo-1,3-dipropyl-2,3,6,7-tetrahydro-1H-purin-8-yl)-1-methyl-1H-pyrazol-3-yl]-2-phenylpropanamide;

{3-[(E)-2-(1,3-dipropyl-7-methyl-2,6-dioxo-2,3,6,7-tetrahydro-1H-purin-8-yl)vinyl]isoxazol-5-yl}methyl benzoate;

2-(4-chlorophenoxy)-N-[5-(1,3-dipropyl-2,6-dioxo-2,3,6,7-tetrahydro-1H-purin-8-yl)-1-methyl-1H-pyrazol-3-yl]acetamide;

N-[5-(2,6-dioxo-1,3-dipropyl-2,3,6,9-tetrahydro-1H-purin-8-yl)-1-methyl-1H-pyrazol-3-yl]-2-(4-fluorophenyl)acetamide;

2-(4-methoxyphenyl)-N-[5-(2,6-dioxo-1,3-dipropyl-2,3,6,9-tetrahydro-1H-purin-8-yl)-1-methyl-1H-pyrazol-3-yl]acetamide;

N-[5-(2,6-dioxo-1,3-dipropyl-2,3,6,9-tetrahydro-1H-purin-8-yl)-1-methyl-1H-pyrazol-3-yl]-2-(3-chlorophenyl)acetamide;

N-[5-(2,6-dioxo-1,3-dipropyl-2,3,6,9-tetrahydro-1H-purin-8-yl)-1-methyl-1H-pyrazol-3-yl]-2-(3-fluorophenyl)acetamide;

N-[5-(2,6-dioxo-1,3-dipropyl-2,3,6,9-tetrahydro-1H-purin-8-yl)-1-methyl-1H-pyrazol-3-yl]-2-[4-(N,N-dimethylamino)phenyl]acetamide;

N-[5-(2,6-dioxo-1,3-dipropyl-2,3,6,9-tetrahydro-1H-purin-8-yl)-1-methyl-1H-pyrazol-3-yl]-2-(4-chlorophenyl)acetamide;

2-(3,4-dimethoxyphenyl)-N-[5-(2,6-dioxo-1,3-dipropyl-2,3,6,9-tetrahydro-1H-purin-8-yl)-1-methyl-1H-pyrazol-3-yl]acetamide;

N-[5-(2,6-dioxo-1,3-dipropyl-2,3,6,9-tetrahydro-1H-purin-8-yl)-1-methyl-1H-pyrazol-3-yl]-2-(4-{[2-(trifluoromethyl)benzyl]oxy}phenyl)acetamide;

N-[5-(2,6-dioxo-1,3-dipropyl-2,3,6,9-tetrahydro-1H-purin-8-yl)-1-methyl-1H-pyrazol-3-yl]-2-(4-{[3-(trifluoromethyl)benzyl]oxy}phenyl)acetamide;

N-[5-(2,6-dioxo-1,3-dipropyl-2,3,6,9-tetrahydro-1H-purin-8-yl)-1-methyl-1H-pyrazol-3-yl]-2-(4-{4-nitrobenzyloxy}phenyl)acetamide;

N-[5-(2,6-dioxo-1,3-dipropyl-2,3,6,9-tetrahydro-1H-purin-8-yl)-1-methyl-1H-pyrazol-3-yl]-2-[4-(trifluoromethyl)phenyl]acetamide;

phenyl 4-[(E)-2-(7-methyl-1,3-dipropyl-2,6-dioxo-2,3,6,7-tetrahydro-1H-purin-8-yl)vinyl]-1-methyl-1H-pyrrole-2-carboxylate;

N-[5-(2,6-dioxo-1,3-dipropyl-2,3,6,9-tetrahydro-1H-purin-8-yl)-1-methyl-1H-pyrazol-5-yl]-2-phenylacetamide;

8-(5-amino-1-methyl-1H-pyrazol-5-yl)-1,3-dipropyl-3,7-dihydro-1H-purine-2,6-dione;

8-(3-amino-1-methyl-1H-pyrazol-5-yl)-1,3-dimethyl-3,7-dihydro-1H-purine-2,6-dione;

N-[5-(2,6-dioxo-1,3-dimethyl-2,3,6,9-tetrahydro-1H-purin-8-yl)-1-methyl-1H-pyrazol-3-yl]-2-phenylacetamide;

N-[5-(2,6-dioxo-1,3-dipropyl-2,3,6,9-tetrahydro-1H-purin-8-yl)-1-methyl-1H-pyrazol-3-yl]-2-(3,4-difluorophenyl)acetamide;

2-(2,3,4-trimethoxyphenyl)-N-[5-(2,6-dioxo-1,3-dipropyl-2,3,6,9-tetrahydro-1H-purin-8-yl)-1-methyl-1H-pyrazol-3-yl]acetamide;

N-[4-(dimethylamino)phenyl]-N'-[5-(2,6-dioxo-1,3-dipropyl-2,3,6,7-tetrahydro-1H-purin-8-yl)-1-methyl-1H-pyrazol-3-yl]urea;

N-(3-chlorophenyl)-N'-[5-(2,6-dioxo-1,3-dipropyl-2,3,6,7-tetrahydro-1H-purin-8-yl)-1-methyl-1H-pyrazol-3-yl]urea;

N-[5-(2,6-dioxo-1,3-dipropyl-2,3,6,7-tetrahydro-1H-purin-8-yl)-1-methyl-1H-pyrazol-3-yl]-N'-(3-methoxyphenyl)urea;

2-[4-(benzyloxy)-3-methoxyphenyl]-N-[5-(2,6-dioxo-1,3-dipropyl-2,3,6,9-tetrahydro-1H-purin-8-yl)-1-methyl-1H-pyrazol-3-yl]acetamide;

2-(1,3-benzodioxol-5-yl)-N-[5-(2,6-dioxo-1,3-dipropyl-2,3,6,9-tetrahydro-1H-purin-8-yl)-1-methyl-1H-pyrazol-3-yl]acetamide;

N-[5-(2,6-dioxo-1,3-dipropyl-2,3,6,9-tetrahydro-1H-purin-8-yl)-1-methyl-1H-pyrazol-3-yl]-2-(4-hydroxy-3-methoxyphenyl)acetamide;

N-(4-methylphenyl)-2-{[5-(1,3-dipropyl-2,6-dioxo-2,3,6,7-tetrahydro-1H-purin-8-yl)-1-methyl-1H-pyrazol-3-yl]oxy}acetamide;

N-(4-bromophenyl)-2-{[3-(2,6-dioxo-1,3-dipropyl-2,3,6,9-tetrahydro-1H-purin-8-yl)-1-methyl-1H-pyrazol-5-yl]oxy}acetamide;

N-(4-fluorophenyl)-2-{[3-(2,6-dioxo-1,3-dipropyl-2,3,6,9-tetrahydro-1H-purin-8-yl)-1-methyl-1H-pyrazol-5-yl]oxy}acetamide;

2-{[3-(1,3-diisobutyl-2,6-dioxo-2,3,6,9-tetrahydro-1H-purin-8-yl)-1-methyl-1H-pyrazol-5-yl]oxy}-N-(4-fluorophenyl)acetamide;

2-{[3-(1,3-diisobutyl-2,6-dioxo-2,3,6,9-tetrahydro-1H-purin-8-yl)-1-methyl-1H-pyrazol-5-yl]oxy}-N-(4-bromophenyl)acetamide;

2-{[5-(2,6-dioxo-1,3-dipropyl-2,3,6,9-tetrahydro-1H-purin-8-yl)-1-methyl-1H-pyrazol-3-yl]oxy}-N-(4-fluorophenyl)acetamide;

2-{[5-(2,6-dioxo-1,3-dipropyl-2,3,6,9-tetrahydro-1H-purin-8-yl)-1-methyl-1H-pyrazol-3-yl]oxy}-N-(4-bromophenyl)acetamide;

2-{[5-(1,3-diisobutyl-2,6-dioxo-2,3,6,9-tetrahydro-1H-purin-8-yl)-1-methyl-1H-pyrazol-3-yl]oxy}-N-(4-fluorophenyl)acetamide;

2-{[5-(1,3-diisobutyl-2,6-dioxo-2,3,6,9-tetrahydro-1H-purin-8-yl)-1-methyl-1H-pyrazol-3-yl]oxy}-N-(4-bromophenyl)acetamide;

N-1,3-benzodioxol-5-yl-2-{[5-(2,6-dioxo-1,3-dipropyl-2,3,6,9-tetrahydro-1H-purin-8-yl)-1-methyl-1H-pyrazol-3-yl]oxy}acetamide;

2-{[5-(2,6-dioxo-1,3-dipropyl-2,3,6,9-tetrahydro-1H-purin-8-yl)-1-methyl-1H-pyrazol-3-yl]oxy}-N-(4-methoxyphenyl)acetamide;

1-[5-(2,6-dioxo-1,3-dipropyl-2,3,6,7-tetrahydro-1H-purin-8-yl)-1-methyl-1H-pyrazol-3-yl]-3-(4-methoxyphenyl)-urea;

1,3-di-n-propyl-8-{5-[(4-sec-butyl-phenylcarbamoyl)-methoxy]-2-methyl-2H-pyrazole-3-yl}-xanthine;

1,3-di-n-propyl-8-{5-[(4-methyl-phenylcarbamoyl)-methoxy]-2-methyl-2H-pyrazole-3-yl}-xanthine;

1,3-di-n-propyl-8-{5-[(4-(morpholine-4-yl)-phenylcarbamoyl)-methoxy]-2-methyl-2H-pyrazole-3-yl}-xanthine;

1,3-di-n-propyl-8-{5-[(4-carboxy-phenylcarbamoyl)-methoxy]-2-methyl-2H-pyrazole-3-yl}-xanthine;

1,3-di-n-propyl-8-{5-[(3,4-dimethyl-phenylcarbamoyl)-methoxy]-2-methyl-2H-pyrazole-3-yl}-xanthine;

1,3-di-n-propyl-8-{5-[(3,4-dimethoxy-phenylcarbamoyl)-methoxy]-2-methyl-2H-pyrazole-3-yl}-xanthine;

1,3-di-n-propyl-8-{5-[(pyridin-4-yl)-methoxyl-2-methyl-2H-pyrazole-3-yl}-xanthine;

1,3-di-n-propyl-8-{5-[2-oxo-2-(4-phenyl-piperazin-1-yl)-ethoxyl-2-methyl-2H-pyrazole-3-yl}-xanthine;

8-(5-{2-[4-(4-fluorophenyl)-piperazin-1-yl]-2-oxo-ethoxy}-2-methyl-2H-pyrazol-3-yl)-1,3-dipropyl-3,7-dihydro-purine-2,6-dione;

1,3-di-n-propyl-8-{5-[2-oxo-2-(4-methyl-piperazin-1-yl)-ethoxy]-2-methyl-2H-pyrazole-3-yl}-xanthine;

8-(5-{2-[4-(4-benzyl-phenyl)-piperazin-1-yl]-2-oxo-ethoxy}-2-methyl-2H-pyrazol-3-yl)-1,3-dipropyl-3,7-dihydro-purine-2,6-dione;

1,3-di-allyl-8-{5-[2-oxo-2-(4-phenyl-piperazin-1-yl)-ethoxy]-2-methyl-2H-pyrazole-3-yl}-xanthine;

1,3-di-n-propyl-8-{3-[(3,4-methylendioxy-phenylcarbamoyl)-methoxy]-isoxazol-5-yl}-xanthine;

1,3-di-n-propyl-8-{3-[(3,4-dimethoxy-phenylcarbamoyl)-methoxy]-isoxazol-5-yl}-xanthine;

1,3-di-n-propyl-8-{3-[(4-fluoro-phenylcarbamoyl)-methoxy]-isoxazol-5-yl}-xanthine;

1,3-di-n-propyl-8-{3-[(4-methoxy-phenylcarbamoyl)-methoxy]-isoxazol-5-yl}-xanthine;

1,3-di-n-propyl-8-{6-[(4-iodo-phenylcarbamoyl)-methoxy]-pyridin-3-yl}-xanthine;

1,3-di-n-propyl-8-{6-[(4-iodo-phenylcarbamoyl)-methoxy]-pyridazin-3-yl}-xanthine;

N-1,3-benzodioxol-5-yl-2-{[5-(2,6-dioxo-1,3-diallyl-2,3,6,9-tetrahydro-1H-purin-8-yl)-1-methyl-1H-pyrazol-3-yl]oxy}acetamide;

1,3-di-n-propyl-8-{5-[(4-(ethoxycarbonyl)-methoxy]-2-methyl-2H-pyrazole-3-yl}-xanthine;

1,3-di-n-propyl-8-(2-hydroxypyridin-5-yl)-xanthine; and 1,3-di-n-propyl-8-{5-[(4-(aminosulfonyl)phenylcarbamoyl)-methoxy]-2-methyl-2H-pyrazole-3-yl}-xanthine;

or a pharmaceutically acceptable salt thereof.

3. A method of treating asthma, which method comprises administering to a patient in need of treatment thereof an effective amount of a compound selected from the group consisting of:

N-[5-(2,6-dioxo-1,3-dipropyl-2,3,6,9-tetrahydro-1H-purin-8-yl)-1-methyl-1H-pyrazol-3-yl]-2-phenylacetamide;

2-(3-methoxyphenyl)-N-[5-(2,6-dioxo-1,3-dipropyl-2,3,6,9-tetrahydro-1H-purin-8-yl)-1-methyl-1H-pyrazol-3-yl]acetamide;

N-[5-(2,6-dioxo-1,3-dipropyl-2,3,6,9-tetrahydro-1H-purin-8-yl)-1-methyl-1H-pyrazol-3-yl]-2-(4-nitrophenyl)acetamide;

2-[4-benzyloxyphenyl]-N-[5-(2,6-dioxo-1,3-dipropyl-2,3,6,9-tetrahydro-1H-purin-8-yl)-1-methyl-1H-pyrazol-3-yl]acetamide;

2-[4-hydroxyphenyl]-N-[5-(2,6-dioxo-1,3-dipropyl-2,3,6,9-tetrahydro-1H-purin-8-yl)-1-methyl-1H-pyrazol-3-yl]acetamide;

N-[5-(2,6-dioxo-1,3-dipropyl-2,3,6,9-tetrahydro-1H-purin-8-yl)-1-methyl-1H-pyrazol-3-yl]-2-(4-fluorophenyl)acetamide;

2-(4-methoxyphenyl)-N-[5-(2,6-dioxo-1,3-dipropyl-2,3,6,9-tetrahydro-1H-purin-8-yl)-1-methyl-1H-pyrazol-3-yl]acetamide;

N-[5-(2,6-dioxo-1,3-dipropyl-2,3,6,9-tetrahydro-1H-purin-8-yl)-1-methyl-1H-pyrazol-3-yl]-2-(3-chlorophenyl)acetamide;

N-[5-(2,6-dioxo-1,3-dipropyl-2,3,6,9-tetrahydro-1H-purin-8-yl)-1-methyl-1H-pyrazol-3-yl]-2-(3-fluorophenyl)acetamide;

N-[5-(2,6-dioxo-1,3-dipropyl-2,3,6,9-tetrahydro-1H-purin-8-yl)-1-methyl-1H-pyrazol-3-yl]-2-[4-(N,N-dimethylamino)phenyl]acetamide;

N-[5-(2,6-dioxo-1,3-dipropyl-2,3,6,9-tetrahydro-1H-purin-8-yl)-1-methyl-1H-pyrazol-3-yl]-2-(4-chlorophenyl)acetamide;

2-(3,4-dimethoxyphenyl)-N-[5-(2,6-dioxo-1,3-dipropyl-2,3,6,9-tetrahydro-1H-purin-8-yl)-1-methyl-1H-pyrazol-3-yl]acetamide;

N-[5-(2,6-dioxo-1,3-dipropyl-2,3,6,9-tetrahydro-1H-purin-8-yl)-1-methyl-1H-pyrazol-3-yl]-2-(4-{[2-(trifluoromethyl)benzyl]oxy}phenyl)acetamide;

N-[5-(2,6-dioxo-1,3-dipropyl-2,3,6,9-tetrahydro-1H-purin-8-yl)-1-methyl-1H-pyrazol-3-yl]-2-(4-{[3-(trifluoromethyl)benzyl]oxy}phenyl)acetamide;

N-[5-(2,6-dioxo-1,3-dipropyl-2,3,6,9-tetrahydro-1H-purin-8-yl)-1-methyl-1H-pyrazol-3-yl]-2-(4-{4-nitrobenzyloxy}phenyl)acetamide;

N-[5-(2,6-dioxo-1,3-dipropyl-2,3,6,9-tetrahydro-1H-purin-8-yl)-1-methyl-1H-pyrazol-5-yl]-2-phenylacetamide;

8-(5-amino-1-methyl-1H-pyrazol-3-yl)-1,3-dipropyl-3,7-dihydro-1H-purine-2,6-dione;
N-[5-(2,6-dioxo-1,3-dipropyl-2,3,6,9-tetrahydro-1H-purin-8-yl)-1-methyl-1H-pyrazol-3-yl]-2-(3,4-difluorophenyl)acetamide;
N-[4-(dimethylamino)phenyl]-N'-[5-(2,6-dioxo-1,3-dipropyl-2,3,6,7-tetrahydro-1H-purin-8-yl)-1-methyl-1H-pyrazol-3-yl]urea;
N-(3-chlorophenyl)-N'-[5-(2,6-dioxo-1,3-dipropyl-2,3,6,7-tetrahydro-1H-purin-8-yl)-1-methyl-1H-pyrazol-3-yl]urea;
N-[5-(2,6-dioxo-1,3-dipropyl-2 3,6,7-tetrahydro-1H-purin-8-yl)-1-methyl-1H-pyrazol-3-yl]-N'-(3-methoxyphenyl)urea;
2-[4-(benzyloxy)-3-methoxyphenyl]-N-[5-(2,6-dioxo-1,3-dipropyl-2,3,6,9-tetrahydro-1H-purin-8-yl)-1-methyl-1H-pyrazol-3-yl]acetamide;
2-(1,3-benzodioxol-5-yl)-N-[5-(2,6-dioxo-1,3-dipropyl-2,3,6,9-tetrahydro-1H-purin-8-yl)-1-methyl-1H-pyrazol-3-yl]acetamide;
N-(4-bromophenyl)-2-{[3-(2,6-dioxo-1,3-dipropyl-2,3,6,9-tetrahydro-1H-purin-8-yl)-1-methyl-1H-pyrazol-5-yl]oxy}acetamide;
2-{[3-(1,3-diisobutyl-2,6-dioxo-2,3,6,9-tetrahydro-1H-purin-8-yl)-1-methyl-1H-pyrazol-5-yl]oxy}-N-(4-bromophenyl)acetamide;
2-{[5-(2,6-dioxo-1,3-dipropyl-2,3,6,9-tetrahydro-1H-purin-8-yl)-1-methyl-1H-pyrazol-3-yl]oxy}-N-(4-fluorophenyl)acetamide;
2-{[5-(2,6-dioxo-1,3-dipropyl-2,3,6,9-tetrahydro-1H-purin-8-yl)-1-methyl-1H-pyrazol-3-yl]oxy}-N-(4-bromophenyl)acetamide;
2-{[5-(1,3-diisobutyl-2,6-dioxo-2,3,6,9-tetrahydro-1H-purin-8-yl)-1-methyl-1H-pyrazol-3-yl]oxy}-N-(4-bromophenyl)acetamide;
N-1,3-benzodioxol-5-yl-2-{[5-(2,6-dioxo-1,3-dipropyl-2,3,6,9-tetrahydro-1H-purin-8-yl)-1-methyl-1H-pyrazol-3-yl]oxy}acetamide; and
2-{[5-(2,6-dioxo-1,3-dipropyl-2,3,6,9-tetrahydro-1H-purin-8-yl)-1-methyl-1H-pyrazol-3-yl]oxy}-N-(4-methoxyphenyl)acetamide;
or a pharmaceutically acceptable salt thereof.

4. A method of treating asthma, which method comprises administering to a patient in need of treatment thereof an effective amount of a compound selected from the group consisting of:
2-(3-methoxyphenyl)-N-[5-(2,6-dioxo-1,3-dipropyl-2,3,6,9-tetrahydro-1H-purin-8-yl)-1-methyl-1H-pyrazol-3-yl]acetamide;
N-[5-(2,6-dioxo-1,3-dipropyl-2,3,6,9-tetrahydro-1H-purin-8-yl)-1-methyl-1H-pyrazol-3-yl]-2-(4-nitrophenyl)acetamide;
2-[4-benzyloxyphenyl]-N-[5-(2,6-dioxo-1,3-dipropyl-2,3,6,9-tetrahydro-1H-purin-8-yl)-1-methyl-1H-pyrazol-3-yl]acetamide;
2-[4-hydroxyphenyl]-N-[5-(2,6-dioxo-1,3-dipropyl-2,3,6,9-tetrahydro-1H-purin-8-yl)-1-methyl-1H-pyrazol-3-yl]acetamide;
N-[5-(2,6-dioxo-1,3-dipropyl-2,3,6,9-tetrahydro-1H-purin-8-yl)-1-methyl-1H-pyrazol-3-yl]-2-[4-(N,N-dimethylamino)phenyl]acetamide;
2-(3,4-dimethoxyphenyl)-N-[5-(2,6-dioxo-1,3-dipropyl-2,3,6,9-tetrahydro-1H-purin-8-yl)-1-methyl-1H-pyrazol-3-yl]acetamide;
8-(3-amino-1-methyl-1H-pyrazol-5-yl)-1,3-dimethyl-3,7-dihydro-1H-purine-2,6-dione;
N-[5-(2,6-dioxo-1,3-dimethyl-2,3,6,9-tetrahydro-1H-purin-8-yl)-1-methyl-1H-pyrazol-3-yl]-2-phenylacetamide;
N-(4-methylphenyl)-2-{[5-(1,3-dipropyl-2,6-dioxo-2,3,6,7-tetrahydro-1H-purin-8-yl)-1-methyl-1H-pyrazol-3-yl]oxy}acetamide; and
2-{[5-(2,6-dioxo-1,3-dipropyl-2,3,6,9-tetrahydro-1H-purin-8-yl)-1-methyl-1H-pyrazol-3-yl]oxy}-N-(4-methoxyphenyl)acetamide;
or a pharmaceutically acceptable salt thereof.

5. A method of treating asthma, which method comprises administering to a patient in need of treatment thereof an effective amount of a compound of formula (IA):

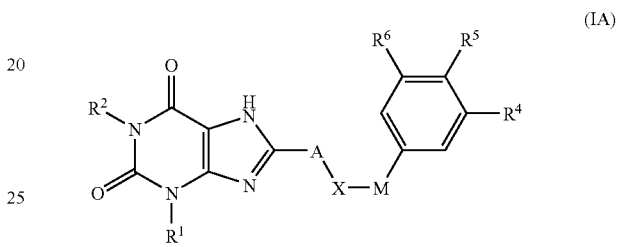

(IA)

wherein
$R^1$ and $R^2$ are independently ($C_1$ to $C_3$)alkyl or allyl;
A is a carbon-carbon bond;
X is selected from the group consisting of

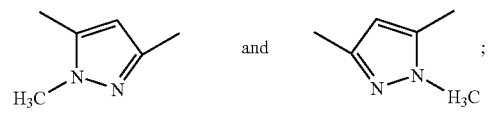

M is selected from the group consisting of —NHC(O)CH$_2$—, —NHC(O)CH$_2$O—, —NHC(O)CH(CH$_3$)—, and —NHC(O)NH—;
$R^4$, $R^5$ and $R^6$ are independently hydrogen, ($C_1$ to $C_4$)alkyl, ($C_2$ to $C_5$)alkenyl, ($C_2$ to $C_5$)alkynyl, optionally substituted ($C_6$ to $C_{10}$)aryl, ($C_7$ to $C_{14}$)aralkyl, ($C_8$ to $C_{14}$)aralkenyl, or ($C_8$ to $C_{14}$)aralkynyl, acyl, optionally substituted alkoxy, aralkoxy, amino, substituted amino, disubstituted amino, fluoro, chloro, bromo, nitro, hydroxy, CO$_2$H; or
taken together with the carbon atoms to which they are attached either $R^4$ and $R^5$ or $R^5$ and $R^6$ form a five or six-membered heterocyclic or heteroaromatic ring containing one to four hetereoatoms selected from nitrogen, oxygen, or sulfur; or
taken together with the carbon atoms to which they are attached either $R^4$ and $R^5$ or $R^5$ and $R^6$ form a heterocyclic fused ring in which either $R^4$ and $R^5$ or $R^5$ and $R^6$ combined are —OCH$_2$O—;
or a pharmaceutically acceptable salt thereof.

6. A method of treating asthma, which method comprises administering to a patient in need of treatment thereof an effective amount of a compound of formula (IB):

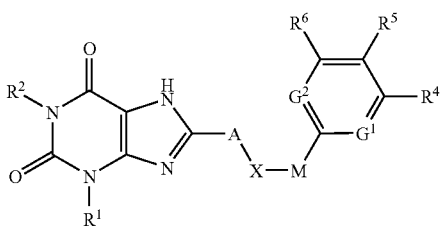

wherein
R¹ and R² are independently ($C_1$ to $C_4$)alkyl;
A is a carbon-carbon bond;
X is selected from the group consisting of

M is —OCH₂C(O)NH—;
G¹ and G² are independently CH or N;
R⁴, R⁵ and R⁶ are independently hydrogen, ($C_1$ to $C_4$)alkyl, ($C_2$ to $C_5$)alkenyl, ($C_2$ to $C_5$)alkynyl, optionally substituted ($C_6$ to $C_{10}$)aryl, ($C_7$ to $C_{14}$)aralkyl, ($C_8$ to $C_{14}$)aralkenyl, or ($C_8$ to $C_{14}$)aralkynyl, acyl, optionally substituted alkoxy, aralkoxy, amino, substituted amino, disubstituted amino, fluoro, chloro, bromo, nitro, hydroxy, CO₂H; or
taken together with the carbon atoms to which they are attached either R⁴ and R⁵ or R⁵ and R⁶ form a five or six-membered heterocyclic or heteroaromatic ring containing one to four hetereoatoms selected from nitrogen, oxygen, or sulfur; or
taken together with the carbon atoms to which they are attached either R⁴ and R⁵ or R⁵ and R⁶ form a heterocyclic fused ring comprising —OCH₂O—;
or a pharmaceutically acceptable salt thereof.

7. A method of treating asthma, which method comprises administering to a patient in need of treatment thereof an effective amount of a compound of formula (IC):

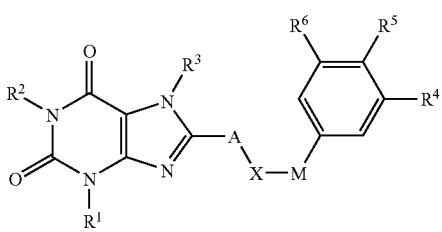

wherein
R¹ and R² are independently ($C_1$ to $C_3$)alkyl;
R³ is hydrogen or methyl;

A is selected from the group consisting of a carbon-carbon bond and —CH=CH—;
X is

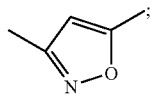

M is —CH₂OC(O)—;
R⁴, R⁵ and R⁶ are independently hydrogen, ($C_1$ to $C_4$)alkyl, ($C_2$ to $C_5$)alkenyl, ($C_2$ to $C_5$)alkynyl, optionally substituted ($C_6$ to $C_{10}$)aryl, ($C_7$ to $C_{14}$)aralkyl, ($C_8$ to $C_{14}$)aralkenyl, or ($C_8$ to $C_{14}$)aralkynyl, acyl, optionally substituted alkoxy, aralkoxy, amino, substituted amino, disubstituted amino, fluoro, chloro, bromo, nitro, hydroxy, CO₂H; or
taken together with the carbon atoms to which they are attached either R⁴ and R⁵ or R⁵ and R⁶ form a five or six-membered heterocyclic or heteroaromatic ring containing one to four hetereoatoms selected from nitrogen, oxygen, or sulfur;
or a pharmaceutically acceptable salt thereof.

8. A method of treating asthma, which method comprises administering to a patient in need of treatment thereof an effective amount of a compound of formula (I):

(I)

wherein
R¹ and R² are independently hydrogen, ($C_1$ to $C_8$)alkyl, ($C_2$ to $C_8$)alkenyl, ($C_2$ to $C_8$)alkynyl, ($C_7$ to $C_{14}$)aralkyl, ($C_8$ to $C_{14}$)aralkenyl, or ($C_8$ to $C_{14}$)aralkynyl;
R³ is hydrogen, ($C_1$ to $C_4$) alkyl, ($C_2$ to $C_5$)alkenyl, or ($C_2$ to $C_5$)alkynyl;
A is a carbon-carbon bond, alkyl chain of one to four carbons, alkenyl chain of two to four carbons, or alkynyl chain of two to four carbons;
X is a five or six-membered heteroaromatic ring, containing one to four heteroatoms, selected from nitrogen, oxygen, or sulfur, provided that at least one heteroatom is nitrogen, wherein the heteroaromatic ring may be optionally substituted by one or two substituents selected from the group consisting of lower alkyl, amino, hydroxy, alkyloxy, acyloxy and acylamino;
M is a ($C_1$ to $C_8$)alkylene, ($C_2$ to $C_8$)alkenylene, or ($C_2$ to $C_8$)alkynylene, wherein at least one of the carbon atoms of the alkylene, alkenylene, or alkynylene group is present as a carbonyl, and one or more of the remaining carbon atoms of the alkylene, alkenylene, or alkynylene group may be replaced by —O—, —N(R⁷)—, —S—, —S(O)—, or —S(O)₂—; or a carbon substituted with a lower alkyl group;
G¹ and G² are independently CH or N;
R⁴, R⁵ and R⁶ are independently hydrogen, ($C_1$ to $C_4$)alkyl, ($C_2$ to $C_5$)alkenyl, ($C_2$ to $C_5$)alkynyl, optionally substituted ($C_6$ to $C_{10}$)aryl, ($C_7$ to $C_{14}$)aralkyl, ($C_8$ to $C_{14}$)aralkenyl, or ($C_8$ to $C_{14}$)aralkynyl, acyl, optionally substituted alkoxy, aralkoxyalkylthio, amino, substituted amino, disubstituted amino, fluoro, chloro, bromo, iodo, nitro, cyano, azido, hydroxy, sulflhydryl, S(O)alkyl, S(O)$_2$alkyl, $CO_2H$, $SO_3H$; or taken together with the carbon atoms to which they are attached either $R^4$ and $R^5$ or $R^5$ and $R^6$ form a five or six-membered heterocyclic or heteroaromatic ring containing one to four hetereoatoms selected from nitrogen, oxygen, or sulfur; or taken together with the carbon atoms to which they are attached either $R^4$ and $R^5$ or $R^5$ and $R^6$ form a carbocyclic or heterocyclic fused ring selected from the group of fused rings comprising —$OCH_2O$—, —$OCH(R^7)$O—, —$OC(R^7)_2O$—, —$OCH_2CH_2O$—, —$OCH_2CH_2$—, —$CH_2CH_2O$—, —$OCH_2CH_2CH_2$—, —$CH_2CH_2CH_2O$—, —$OCH=CH$—, —$CH=CH$—O—, —O—$CH=CH$—O—, —$CH=CH$—$CH=CH$—, —$CH_2CH_2CH_2$— and —$CH_2CH_2CH_2CH_2$—;

$R^7$ is hydrogen, ($C_1$ to $C_4$)alkyl, ($C_2$ to $C_5$)alkenyl, or ($C_2$ to $C_5$)alkynyl;

or a pharmaceutically acceptable salt thereof.

9. A method of treating asthma, which method comprises administering to a patient in need of treatment thereof an effective amount of a compound of formula (I):

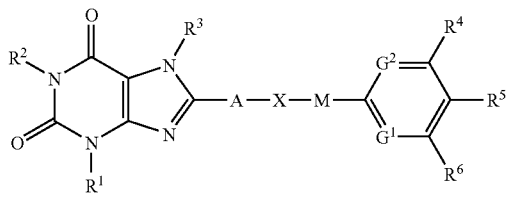

(I)

wherein
$R^1$ and $R^2$ are each n-propyl; $R^3$ is hydrogen; A is a carbon-carbon bond;
X is

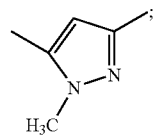

M is —$NHC(O)CH_2$—; $G^1$ and $G^2$ are each CH; $R^4$ and $R^6$ are hydrogen; $R^5$ is benzyloxy:
or a pharmaceutically acceptable salt thereof.

10. A method of treating asthma, which method comprises administering to a patient in need of treatment thereof an effective amount of a compound of formula (III):

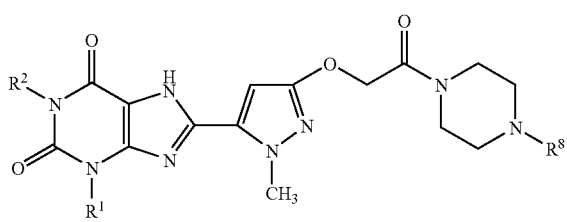

(III)

wherein
$R^1$ and $R^2$ are independently hydrogen, ($C_1$ to $C_8$)alkyl, ($C_2$ to $C_8$)alkenyl, ($C_2$ to $C_8$)alkynyl, ($C_7$ to $C_{14}$)aralkyl, ($C_8$ to $C_{14}$)aralkenyl, or ($C_8$ to $C_{14}$)aralkynyl;
$R^8$ is phenyl, halogen substituted phenyl, ($C_1$ to $C_8$)alkyl, or benzyl;
or a pharmaceutically acceptable salt thereof.

* * * * *

UNITED STATES PATENT AND TRADEMARK OFFICE
CERTIFICATE OF CORRECTION

PATENT NO.        : 7,335,655 B2
APPLICATION NO.   : 11/359661
DATED             : February 26, 2008
INVENTOR(S)       : Pier Giovanni Baraldi and Pier A. Borea Page 1 of 1

It is certified that error appears in the above-identified patent and that said Letters Patent is hereby corrected as shown below:

Column 10, lines 10 to 14, the structure should appear as follows:

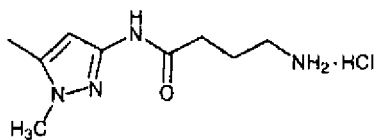

Column 52, lines 28 to 36, the structure should appear as follows:

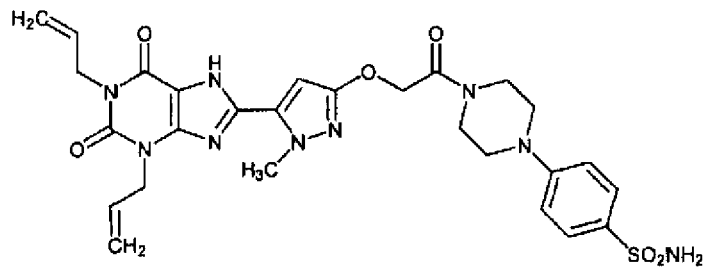

Signed and Sealed this

Twenty-third Day of September, 2008

JON W. DUDAS
*Director of the United States Patent and Trademark Office*